(12) United States Patent
Anderskewitz et al.

(10) Patent No.: US 8,173,699 B2
(45) Date of Patent: May 8, 2012

(54) COMPOUNDS FOR THE TREATMENT OF INFLAMMATORY DISEASES

(75) Inventors: Ralf Anderskewitz, Laupheim (DE); Horst Dollinger, Schemmerhofen (DE); Rolf Goeggel, Ulm (DE); Birgit Jung, Laupheim (DE); Joerg Kley, Mittelbiberach (DE); Jurgen Mack, Biberach an der Riss (DE); Peter Nickolaus, Warthausen (DE); Rainer Walter, Biberach an der Riss (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 12/753,365

(22) Filed: Apr. 2, 2010

(65) Prior Publication Data

US 2010/0190767 A1    Jul. 29, 2010

Related U.S. Application Data

(62) Division of application No. 11/409,482, filed on Apr. 21, 2006, now Pat. No. 7,723,381.

(30) Foreign Application Priority Data

Apr. 28, 2005 (DE) .................. 10 2005 019 718
May 20, 2005 (DE) .................. 10 2005 023 207
Jul. 29, 2005 (DE) .................. 10 2005 035 575

(51) Int. Cl.
*A61K 31/343* (2006.01)
*C07D 307/78* (2006.01)

(52) U.S. Cl. ...................... 514/470; 549/302

(58) Field of Classification Search ................. 549/302; 514/470
See application file for complete search history.

(56) References Cited

U.S. PATENT DOCUMENTS 5,502,072 A    3/1996   Masamune
6,872,839 B1 *  3/2005   Feiler et al. ................. 549/302

FOREIGN PATENT DOCUMENTS

| WO | WO 99/51590   | 10/1999 |
| WO | WO 00/18734   | 4/2000  |
| WO | WO 01/16130   | 3/2001  |
| WO | WO-2004/009547 | 1/2004 |

OTHER PUBLICATIONS

Hilfiker, R. et al. "Polymorphism-Integrated Approach from High-Throughput Screening to Crystallization of . . . ", J. of Thermal Analysis and Calorimetry, 73:429-440 (2003).
Guillory, J. K. et al. "Generation of Polymorphs, Hydrates, Solvates, and Amorphous Solids", pp. 183-226, The University of Iowa, Iowa City, Iowa.
Guillory, J. Keith, "Generation of Polymorphs, Hydrates, Solvates and Amorphous Solids" The University of Iowa, Iowa City Iowa, pp. 183-226.
Hilfiker, R. et al., "Polymorphism-Integrated Approach from High-Throughput Screening to Crystallization Optimization" Journal of Thermal Analysis and Calorimetry V 73:429-440 (2003).

* cited by examiner

*Primary Examiner* — Kamal Saeed
*Assistant Examiner* — Janet L Coppins
(74) *Attorney, Agent, or Firm* — Michael P. Morris; Usha R. Patel

(57) ABSTRACT

Compounds of formula 1 and hetero derivatives thereof

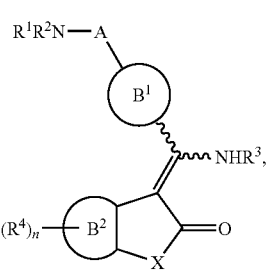

and the pharmacologically acceptable salts, enantiomers, racemates, hydrates, or solvates thereof, which are suitable for the treatment of respiratory or gastrointestinal complaints or diseases, inflammatory diseases of the joints, skin, or eyes, diseases of the peripheral or central nervous system or cancers, as well as pharmaceutical compositions which contain these compounds.

20 Claims, No Drawings

COMPOUNDS FOR THE TREATMENT OF INFLAMMATORY DISEASES

This application is a divisional of U.S. Ser. No. 11/409,482, filed Apr. 21, 2006.

RELATED APPLICATIONS

This application claims priority to German Application No. DE 10 2005 019 718.3, filed Apr. 28, 2005, German Application No. DE 10 2005 023 207.8, filed May 20, 2005, and German Application No. DE 10 2005 035 575.7, filed Jul. 29, 2005, each of which are hereby incorporated by reference in its entirety.

FIELD OF THE INVENTION

The invention relates to new compounds of formula of formula 1 and hetero derivatives thereof, as well as pharmacologically acceptable salts, diastereomers, enantiomers, racemates, hydrates, or solvates thereof

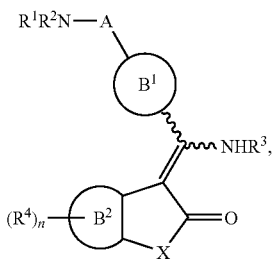

which are suitable for the treatment of respiratory or gastrointestinal complaints or diseases, inflammatory diseases of the joints, skin, or eyes, diseases of the peripheral or central nervous system or cancers, as well as pharmaceutical compositions which contain these compounds.

BRIEF DESCRIPTION OF THE INVENTION

Surprisingly it has now been found that the compounds of formula 1 are suitable for the treatment of inflammatory diseases. The present invention therefore relates to compounds of formula 1

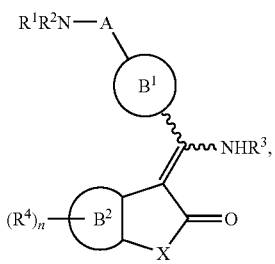

wherein:
A denotes CO, C=NH, $C_{1-6}$-alkylene, or $C_{3-8}$-cycloalkylene;
$B^1$ denotes phenyl or an aromatic or non-aromatic ring which may optionally contain one, two, or three heteroatoms, selected from among oxygen, sulfur, and nitrogen and which may optionally be mono- or polysubstituted by one or more groups selected from among OH, O—$C_{1-6}$-alkyl, O—$C_{1-6}$-haloalkyl, halogen, $C_{1-6}$-alkyl, and $C_{1-6}$-haloalkyl;
$B^2$ denotes phenyl or a heteroaryl, which may contain one, two, or three heteroatoms selected from among oxygen, sulfur, and nitrogen;
X denotes O, S, $NR^5$, or $CR^6R^7$;
n denotes 0, 1, 2, or 3;
$R^1$ denotes H, $C_{1-6}$-alkyl, $C_{1-6}$-haloalkyl, $COR^{1.1}$, $COOR^{1.1}$, or $CH_2COOR^{1.1}$; preferably H, $C_{1-6}$-alkyl, or $C_{1-6}$-haloalkyl, wherein $R^{1.1}$ denotes H or $C_{1-6}$-alkyl;
$R^2$ denotes H, $C_{1-6}$-alkyl, or $C_{1-6}$-haloalkyl; or
$R^1$ and $R^2$ together with the nitrogen form a non-aromatic heterocycle, which may contain one, two, or three heteroatoms selected from among oxygen and nitrogen; or
$R^2$, N, A, and $B^1$ together form a bicyclic group of formula (i)

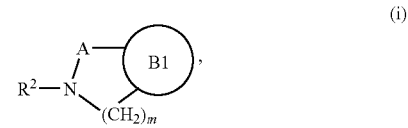

wherein:
A denotes CO, C=NH, or $C_{1-3}$-alkyl,
m denotes 1, 2, or 3, and
$R^3$ denotes H or a group selected from among OH, $C_{1-6}$-haloalkyl, a $C_{6-10}$-aryl, a $C_{5-10}$-heteroaryl, and a $C_{3-10}$-heterocycle, while the $C_{3-10}$-heterocycle and the $C_{5-10}$-heteroaryl may contain one, two, or three heteroatoms selected from among oxygen, sulfur, and nitrogen, which may optionally be substituted by one or more groups selected from among $C_{1-6}$-alkyl, $C_{6-10}$-aryl, optionally bridged $C_{3-8}$-cycloalkyl, and $C_{1-6}$-haloalkyl, which may optionally be substituted by a group selected from $C_{1-6}$-alkyl, $C_{1-6}$-haloalkyl, OH, halogen, and $C_{6-10}$-aryl; or
$R^3$ denotes $C_{1-6}$-alkyl, which may optionally be substituted by one or more groups selected from among halogen, OH, CN, $CONH_2$, CONH—$C_{1-6}$-alkyl, $CON(C_{1-6}$-alkyl$)_2$, COOH, COO—$C_{1-6}$-alkyl, COH, CO—$C_{1-6}$-alkyl, CO—$C_{6-10}$-aryl, OH, O—$C_{1-6}$-alkyl, O—$C_{1-6}$-haloalkyl, halogen, SH, S—$C_{1-6}$-alkyl, S—$C_{1-6}$-haloalkyl, $SO_2$—$C_{1-6}$-alkanol; $SO_2$—$C_{1-6}$-alkyl, $SO_2$—$C_{1-6}$-haloalkyl, $SO_2$—$NH_2$, $SO_2$—NH—$C_{1-6}$-alkyl, $SO_2$—$N(C_{1-6}$-alkyl$)_2$, $NO_2$, $NH_2$, NH—$C_{1-6}$-alkyl, and $N(C_{1-6}$-alkyl$)_2$, or
$R^3$ denotes a group selected from among $C_{3-8}$-cycloalkyl, $C_{5-8}$-cycloalkenyl, $C_{1-6}$-alkyl, and $C_{1-6}$-alkanol, which may optionally be substituted by one or more groups selected from among $C_{6-10}$-aryl, $C_{3-8}$-cycloalkyl, a $C_{5-10}$-heteroaryl, and a $C_{3-10}$-heterocycle, which may optionally be substituted by one or more groups selected from among $C_{1-6}$-alkyl, $C_{2-6}$-alkenyl, $C_{2-6}$-alkynyl, $C_{1-6}$-haloalkyl, CN, $CONH_2$, CONH—$C_{1-6}$-alkyl, $CON(C_{1-6}$-alkyl$)_2$, COOH, COO—$C_{1-6}$-alkyl, COH, CO—$C_{1-6}$-alkyl, $COC_{6-10}$-aryl, OH, O—$C_{1-6}$-alkyl, O—$C_{1-6}$-haloalkyl, halogen, SH, S—$C_{1-6}$-alkyl, S—$C_{1-6}$-haloalkyl, $SO_2$—$C_{1-6}$-alkanol, $SO_2$—$C_{1-6}$-alkyl, $SO_2$—$C_{1-6}$-haloalkyl, $SO_2$—$NH_2$, $SO_2$—NH—$C_{1-6}$-alkyl, $SO_2$—$N(C_{1-6}$-alkyl$)_2$, $NO_2$, $NH_2$, NH—$C_{1-6}$-alkyl, $N(C_{1-6}$-alkyl$)_2$, a $C_{5-10}$-heteroaryl, and a $C_{3-10}$-heterocycle, while the $C_{5-10}$-heteroaryl and the $C_{3-10}$-heterocycle may optionally be substituted by a group selected from oxo, hydroxyl, halogen, $C_{1-6}$-alkyl, and $C_{1-6}$-haloalkyl; or $R^3$ denotes a group selected from among $C_{6-10}$-aryl, a $C_{6-10}$-heteroaryl, and a $C_{3-10}$-heterocycle, which may optionally be substituted by one or more groups selected from among $C_{6-10}$-aryl, $C_{1-6}$-alkyl, $C_{2-6}$-alkenyl, $C_{2-6}$-alkynyl, $C_{1-6}$-haloalkyl, $CONH_2$, $CONH$—$C_{1-6}$-alkyl, $CON(C_{1-6}$-alkyl$)_2$, COOH, COO—$C_{1-6}$-alkyl, COH, CO—$C_{1-6}$-alkyl, CO—$C_{6-10}$-aryl, OH, O—$C_{1-6}$-alkyl, O—$C_{1-6}$-haloalkyl, halogen, SH, S—$C_{1-6}$-alkyl, S—$C_{1-6}$-haloalkyl, $SO_2$—$C_{1-6}$-alkyl, $SO_2$—$C_{1-6}$-alkanol, $SO_2$—$C_{1-6}$-haloalkyl, $SO_2$—$NH_2$, $SO_2$—NH—$C_{1-6}$-alkyl, $SO_2$—$N(C_{1-6}$-alkyl$)_2$, $NO_2$, $NH_2$, NH—$C_{1-6}$-alkyl, $N(C_{1-6}$-alkyl$)_2$, and N—$(SO_2$—$C_{1-4}$-alkyl$)(R^{3.4})$; or $R^3$ denotes a group selected from among $C_{1-6}$-alkyl, $C_{6-10}$-aryl-$C_{1-6}$-alkylene, $C_{5-10}$-heteroaryl-$C_{1-6}$-alkylene, $C_{3-7}$-cycloalkyl, $C_{6-10}$-aryl, a $C_{5-10}$-heteroaryl, and a $C_{3-10}$-heterocycle, which may optionally be substituted by one or more groups selected from among B, halogen, OH, $C_{1-6}$-alkyl, and oxo, while B is a compound of formula 2

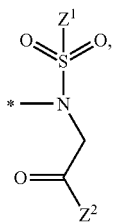

wherein $Z^1$ denotes H, OH, halogen, $C_{1-6}$-alkyl, $C_{1-6}$-alkanol, $O(C_{1-6}$-alkyl), $C_{6-10}$-aryl, O—$C_{6-10}$-aryl, $NH_2$, $NH(C_{1-6}$-alkyl), $N(C_{1-6}$-alkyl$)_2$, or $C_{3-7}$-cycloalkyl; and $Z^2$ denotes OH, $NH_2$, $NH(C_{1-6}$-alkyl), $N(C_{1-6}$-alkyl$)_2$, $O(C_{1-6}$-alkyl), mono- or bicyclic $C_{3-7}$-cycloalkyl, to mono- or bicyclic $C_{3-10}$-heterocycle, mono- or bicyclic $C_{5-10}$-heteroaryl, or $C_{6-10}$-aryl; or $R^3$ denotes a group selected from among $C_{6-10}$-aryl and a $C_{5-10}$-heteroaryl, which may optionally be substituted by $C_{1-6}$-alkyl, which may optionally be substituted by a group selected from among $COOR^{3.3}$, $NR^{3.3}R^{3.4}$, $NHCOR^{3.3}$, $NHCOOR^{3.3}$, phenyl, while phenyl may optionally be substituted by a group selected from among $C_{1-6}$-alkyl, $C_{2-6}$-alkenyl, $C_{2-6}$-alkynyl, CN, $C_{1-6}$-haloalkyl, $CONH_2$, $CONH$—$C_{1-6}$-alkyl, $CON(C_{1-6}$-alkyl$)_2$, COOH, COO—$C_{1-6}$-alkyl, COH, CO—$C_{1-6}$-alkyl, OH, O—$C_{1-6}$-alkyl, O—$C_{1-6}$-haloalkyl, halogen, SH, S—$C_{1-6}$-alkyl, S—$C_{1-6}$-haloalkyl, $SO_2$—$C_{1-6}$-alkyl, $SO_2$—$C_{1-6}$-haloalkyl, $SO_2$—$NH_2$, $SO_2$—NH—$C_{1-6}$-alkyl, $SO_2$—$N(C_{1-6}$-alkyl$)_2$, $NO_2$, $NH_2$, NH—$C_{1-6}$-alkyl, and $N(C_{1-6}$-alkyl$)_2$, a $C_{3-10}$-heterocycle, and a $C_{5-10}$-heteroaryl, while the $C_{3-10}$-heterocycle and the $C_{5-10}$-heteroaryl may optionally be substituted by an oxo group or a methyl group, wherein:

$R^{3.3}$ denotes H or $C_{1-6}$-alkyl, and $R^{3.4}$ denotes H, $C_{1-6}$-alkyl, $C_{6-10}$-aryl-$C_{1-6}$-alkylene, or $C_{5-10}$-heteroaryl-$C_{1-6}$-alkylene, or $R^3$ denotes a group selected from among $C_{6-10}$-aryl and a $C_{5-10}$-heteroaryl, which may optionally be substituted by $NR^{3.1}R^{3.2}$, wherein:

$R^{3.1}$ denotes H, $C_{1-6}$-alkyl, $C_{3-6}$-cycloalkyl, $C_{1-6}$-haloalkyl, $COR^{3.1.1}$, $COOR^{3.1.1}$, $CONR^{3.1.1}R^{3.1.2}$, or $SO_2$—$R^{3.1.1}$, wherein: $R^{3.1.1}$ denotes H, $C_{1-6}$-haloalkyl, $C_{3-6}$-cycloalkyl, or $C_{6-10}$-aryl; and $R^{3.1.2}$ denotes H, $C_{1-6}$-alkyl, $C_{1-6}$-haloalkyl, $C_{3-6}$-cycloalkyl, or $C_{6-10}$-aryl; and $R^{3.2}$ denotes H or a group selected from among $C_{1-6}$-alkyl, $C_{3-7}$-cycloalkyl, and $C_{1-6}$-haloalkyl, which may optionally be substituted by one or more groups selected from among $NH_2$, $NH(C_{1-6}$-alkyl), $N(C_{1-6}$-alkyl$)_2$, oxo, and a non-aromatic $C_{3-10}$-heterocycle, which may contain one or two heteroatoms selected from among nitrogen, oxygen, and sulfur, while the non-aromatic $C_{3-10}$-heterocycle may optionally be substituted by $C_{1-4}$-alkyl; or $R^3$ denotes a group selected from among $C_{6-10}$-aryl and a $C_{5-10}$-heteroaryl, which may optionally be substituted by a $C_{3-10}$-heterocycle, which may optionally be substituted by one or more groups selected from among $C_{6-10}$-aryl, $C_{1-6}$-alkyl, $C_{3-6}$-cycloalkyl, CN, $C_{1-6}$-haloalkyl, $CONH_2$, $CONH$—$C_{1-6}$-alkyl, $CON(C_{1-6}$-alkyl$)_2$, COOH, COO—$C_{1-6}$-alkyl, COH, CO—$C_{1-6}$-alkyl, oxo, OH, O—$C_{1-6}$-alkyl, halogen, SH, S—$C_{1-6}$-alkyl, $NH_2$, NH—$C_{1-6}$-alkyl, and $N(C_{1-6}$-alkyl$)_2$; or $R^3$ denotes benzimidazolyl, which may optionally be substituted by a group selected from among $C_{1-6}$-alkyl, $C_{1-6}$-haloalkyl, and $C_{3-6}$-cycloalkyl;

$R^4$ denotes $C_{1-6}$-alkyl, $C_{3-8}$-cycloalkyl, $C_{1-6}$-haloalkyl, $OR^{4.1}$, $NR^{4.1}R^{4.2}$, CN, or halogen, wherein: $R^{4.1}$ denotes H, $C_{1-6}$-alkyl, $C_{3-8}$-cycloalkyl, or $C_{1-6}$-haloalkyl; and $R^{4.2}$ denotes H, $C_{1-6}$-alkyl, $C_{3-8}$-cycloalkyl, or $C_{1-6}$-haloalkyl;

$R^5$ denotes $C_{1-6}$-alkyl, $C_{3-8}$-cycloalkyl, $C_{1-6}$-haloalkyl, $COR^{5.1}$, $CONHR^{5.1}CON(R^{5.1})_2$, $SO_2$—$C_{1-6}$-alkyl, $SO_2$—$C_{1-6}$-haloalkyl, $SO_2$—$C_{6-10}$-aryl, or a group selected from among $R^{5.2}$, $SO_2$—$C_{1-6}$-alkyl-$R^{5.2}$, and $C_{1-6}$-alkyl-$R^{5.2}$, which may optionally be substituted by one or more groups selected from among $C_{1-6}$-alkyl, $C_{2-6}$-alkenyl, $C_{2-6}$-alkynyl, CN, $C_{1-6}$-haloalkyl, $CONH_2$, $CONH$—$C_{1-6}$-alkyl, $CON(C_{1-6}$-alkyl$)_2$, COOH, COO—$C_{1-6}$-alkyl, COH, CO—$C_{1-6}$-alkyl, O—$C_{3-6}$-cycloalkyl, O—$C_{1-6}$-haloalkyl, O—$C_{1-6}$-alkyl, halogen, $SO_2$—$C_{1-6}$-alkyl, $SO_2$—$NH_2$, $SO_2$—NH—$C_{1-6}$-alkyl, $SO_2$—$N(C_{1-6}$-alkyl$)_2$, $NO_2$, $NH_2$, NH—$C_{1-6}$-alkyl, and $N(C_{1-6}$-alkyl$)_2$, wherein: $R^{5.1}$ denotes $C_{1-6}$-alkyl, $C_{5-10}$-heteroaryl-$C_{1-6}$-alkylene, or $C_{6-10}$-aryl-$C_{1-6}$-alkylene, and $R^{5.2}$ denotes $C_{6-10}$-aryl or a $C_{5-10}$-heteroaryl; and $R^6$ denotes H, $C_{1-6}$-alkyl, or $C_{1-6}$-haloalkyl; and $R^7$ denotes H, $C_{1-6}$-alkyl, or $C_{1-6}$-haloalkyl; or $R^6$ and $R^7$ together form a 3-6 membered carbocycle, optionally in the form of the racemates, enantiomers, diastereomers, and optionally in the form of the pharmacologically acceptable acid addition salts, solvates, or hydrates thereof, as well as deuterated forms thereof.

Preferred compounds of formula 1 above are those wherein:

A denotes CO, C=NH, $C_{1-4}$-alkylene, or $C_{3-6}$-cycloalkylene;

$B^1$ denotes phenyl or a $C_{5-10}$-heteroaryl, which may contain one, two, or three heteroatoms, selected from among oxygen, sulfur, and nitrogen;

$B^2$ denotes phenyl or pyridinyl;

X denotes O, S, $NR^5$, or $CR^6R^7$;

n denotes 0, 1, 2, or 3;

$R^1$ denotes H, $C_{1-4}$-alkyl, $C_{1-4}$-haloalkyl;

$R^2$ denotes H, $C_{1-4}$-alkyl, or $C_{1-4}$-haloalkyl; or $R^1$ and $R^2$ together with the nitrogen form a non-aromatic heterocycle, which may contain one or two nitrogen atoms;

$R^3$ denotes H, OH, $C_{1-4}$-haloalkyl, $C_{6-10}$-aryl, a $C_{5-10}$-heteroaryl, which may contain one, two, or three heteroatoms selected from among oxygen, sulfur, and nitrogen, while the $C_{6-10}$-aryl and the $C_{5-10}$-heteroaryl may optionally be substituted by one or more groups selected from among $C_{1-4}$-alkyl, $C_{3-6}$-cycloalkyl, and $C_{1-4}$-haloalkyl; or $R^3$ denotes a group selected from among $C_{3-8}$-cycloalkyl, $C_{5-8}$-cycloalkenyl, and $C_{1-6}$-alkyl, which may optionally be substituted by one or more groups selected from among $C_{6-10}$-aryl or a $C_{5-10}$-heteroaryl, which may optionally be substituted by one or more 1c) groups selected from among $C_{1-6}$-alkyl, $C_{1-6}$-haloalkyl, CN, OH, O—$C_{1-6}$-alkyl, O—$C_{1-6}$-haloalkyl, halogen, S—$C_{1-6}$-alkyl, S—$C_{1-6}$-haloalkyl, $NO_2$, $NH_2$, NH—$C_{1-6}$-alkyl, and $N(C_{1-6}$-alkyl$)_2$;

a group selected from among $C_{6-10}$-aryl and a heterocyclic, aromatic ring, substituted by is one or more groups selected from among $C_{6-10}$-aryl, $C_{2-4}$-alkenyl, $C_{2-4}$-alkynyl, $C_{1-4}$-haloalkyl, $CONH_2$, CONH—$C_{1-4}$-alkyl, $CON(C_{1-4}$-alkyl$)_2$, COOH, COO—$C_{1-4}$-alkyl, COH, CO—$C_{1-4}$-alkyl, CO—$C_{6-10}$-aryl, OH, O—$C_{1-4}$-alkyl, O—$C_{1-4}$-haloalkyl, halogen, SH, S—$C_{1-4}$-alkyl, S—$C_{1-4}$-haloalkyl, $SO_2$—$C_{1-4}$-alkyl, $SO_2$—$C_{1-4}$-haloalkyl, $SO_2$—$NH_2$, $SO_2$—NH—$C_{1-4}$-alkyl, $SO_2$—$N(C_{1-4}$-alkyl$)_2$, $NO_2$, $NH_2$, NH—$C_{1-4}$-alkyl, and $N(C_{1-4}$-alkyl$)_2$;

a group selected from among $C_{6-10}$-aryl, a $C_{5-10}$-heteroaryl, $C_{6-10}$-aryl-$C_{1-4}$-alkylene, and $C_{5-10}$-heteroaryl-$C_{1-4}$-alkylene, which may optionally be substituted by one or more groups selected from among $COOR^{3.3}$, $NR^{3.3}R^{3.4}$, $NHCOR^{3.3}$, $NHCOOR^{3.3}$, and phenyl, which may optionally be substituted by one or more groups selected from among $C_{1-4}$-alkyl, $C_{2-4}$-alkenyl, $C_{2-4}$-alkynyl, CN, $C_{1-4}$-haloalkyl, $CONH_2$, CONH—$C_{1-4}$-alkyl, $CON(C_{1-4}$-alkyl$)_2$, COOH, COO—$C_{1-4}$-alkyl, COH, CO—$C_{1-4}$-alkyl, OH, O—$C_{1-4}$-alkyl, O—$C_{1-4}$-haloalkyl, halogen, SH, S—$C_{1-4}$-alkyl, S—$C_{1-4}$-halo alkyl, $O_2$—$C_{1-4}$-alkyl, $SO_2$—$C_{1-4}$-haloalkyl, $SO_2$—$NH_2$, $SO_2$—NH—$C_{1-4}$-alkyl, $SO_2$—$N(C_{1-4}$-alkyl$)_2$, $NO_2$, $NH_2$, NH—$C_{1-4}$-alkyl, and $N(C_{1-4}$-alkyl$)_2$, and a $C_{5-10}$-heterocycle, which may contain one, two, or three heteroatoms selected from among oxygen, nitrogen, and sulfur and which may optionally be substituted by an oxo group, wherein: $R^{3.3}$ denotes H or $C_{1-4}$-alkyl, and $R^{3.4}$ denotes H, $C_{1-4}$-alkyl, $C_{6-10}$-aryl-$C_{1-6}$-alkylene, or $C_{5-10}$-heteroaryl-$C_{1-6}$-alkylene; or $R^3$ denotes a group selected from among $C_{6-10}$-aryl and a $C_{5-10}$-heterocycle, which may be substituted by $NR^{3.1}R^{3.2}$, wherein:

$R^{3.1}$ denotes H, $C_{1-4}$-alkyl, $C_{3-6}$-cycloalkyl, $C_{1-4}$-haloalkyl, $COR^{3.1.1}$, $COOR^{3.1.1}$, $CONR^{3.1.1}R^{3.1.2}$, or $SO_2$—$R^{3.1.1}$, wherein: $R^{3.1.1}$ denotes H, $C_{1-4}$-alkyl, $C_{1-4}$-haloalkyl, $C_{3-6}$-cycloalkyl, or $C_{6-10}$-aryl; and $R^{3.1.2}$ denotes H, $C_{1-4}$-alkyl, $C_{1-4}$-haloalkyl, $C_{3-6}$-cycloalkyl, or $C_{6-10}$-aryl; and $R^{3.2}$ denotes H or a group selected from among $C_{1-4}$-alkyl, $C_{3-6}$-cycloalkyl, and $C_{1-4}$-haloalkyl, which may optionally be substituted by one or more groups selected from among $NH_2$, $NH(C_{1-4}$-alkyl), $N(C_{1-4}$-alkyl$)_2$, oxo, and a $C_{3-10}$-heterocycle, which may contain one or two heteroatoms selected from among nitrogen, oxygen, and sulfur and which may optionally be substituted by $C_{1-4}$-alkyl; or $R^3$ denotes $C_{6-10}$-aryl, which may be substituted by a $C_{5-10}$-heteroaryl which may contain one, is two, or three heteroatoms selected from among oxygen, sulfur, and nitrogen and which may optionally be substituted by one or more groups selected from among $C_{6-10}$-aryl, $C_{1-4}$-alkyl, $C_{3-6}$-cycloalkyl, CN, $C_{1-4}$-haloalkyl, $CONH_2$, CONH—$C_{1-4}$-alkyl, $CON(C_{1-4}$-alkyl$)_2$, COOH, COO—$C_{1-4}$-alkyl, COH, CO—$C_{1-4}$-alkyl, OH, O—$C_{1-4}$-alkyl, halogen, SH, S—$C_{1-4}$-alkyl, $NH_2$, NH—$C_{1-4}$-alkyl, and $N(C_{1-4}$-alkyl$)_2$; or $R^3$ denotes $C_{6-10}$-aryl, which may be substituted by a $C_{3-10}$-heterocycle which may contain one or two heteroatoms, selected from among oxygen, sulfur, and nitrogen and which may optionally be substituted by one or more groups selected from among $C_{1-4}$-alkyl and oxo; or $R^3$ denotes benzimidazolyl, which may optionally be substituted by a group selected from among $C_{1-4}$-alkyl, $C_{1-4}$-haloalkyl, and $C_{3-6}$-cycloalkyl;

$R^4$ denotes $C_{1-4}$-alkyl, $C_{3-6}$-cycloalkyl, $C_{1-4}$-haloalkyl, $OR^{4.1}$, $NR^{4.1}R^{4.2}$, CN, or halogen; and $R^{4.1}$ denotes H, $C_{1-4}$-alkyl, $C_{3-6}$-cycloalkyl, or $C_{1-4}$-haloalkyl, and $R^{4.2}$ denotes H, $C_{1-4}$-alkyl, $C_{3-6}$-cycloalkyl, or $C_{1-4}$-haloalkyl;

$R^5$ denotes $C_{1-4}$-alkyl, $C_{3-8}$-cycloalkyl, $C_{1-4}$-haloalkyl, $COR^{5.1}$, $CONHR^{5.1}$, $CON(R^{5.1})_2$, $SO_2$—$C_{1-4}$-alkyl, $SO_2$—$C_{1-4}$-haloalkyl, $SO_2$—$C_{6-10}$-aryl, or a group selected from among $R^{5.2}$, $SO_2$—$C_{1-4}$-alkyl-$R^{5.2}$, and $C_{1-4}$-alkyl-$R^{5.2}$, while this group may optionally be substituted by one or more groups selected from among $C_{1-4}$-alkyl, $C_{2-4}$-alkenyl, $C_{2-4}$-alkynyl, CN, $C_{1-4}$-haloalkyl, $CONH_2$, CONH—$C_{1-4}$-alkyl, $CON(C_{1-4}$-alkyl$)_2$, COOH, COO—$C_{1-4}$-alkyl, COH, CO—$C_{1-4}$-alkyl, O—$C_{1-4}$-cycloalkyl, O—$C_{1-4}$-haloalkyl, O—$C_{1-4}$-alkyl, halogen, $SO_2$—$C_{1-4}$-alkyl, $SO_2$—$NH_2$, $SO_2$—NH—$C_{1-4}$-alkyl, $SO_2$—$N(C_{1-4}$-alkyl$)_2$, $NO_2$, $NH_2$, NH—$C_{1-4}$-alkyl, and $N(C_{1-4}$-alkyl$)_2$, wherein: $R^{5.1}$ denotes $C_{1-4}$-alkyl, $C_{6-10}$-aryl-$C_{1-6}$-alkylene, or $C_{5-10}$-heteroaryl-$C_{1-6}$-alkylene, and $R^{5.2}$ denotes $C_{6-10}$-aryl or a $C_{5-10}$-heteroaryl;

$R^6$ denotes H, $C_{1-4}$-alkyl, or $C_{1-4}$-haloalkyl; and $R^7$ denotes H, $C_{1-4}$-alkyl, or $C_{1-4}$-haloalkyl; or $R^6$ and $R^7$ together form a 3-6 membered carbocycle, optionally in the form of the racemates, enantiomers, diastereomers thereof, and optionally in the form of the pharmacologically acceptable acid addition salts, solvates, or hydrates thereof, as well as deuterated forms thereof.

Preferred compounds of formula 1 above are those wherein:

A denotes CO, C=NH, $C_{1-6}$-alkylene, or $C_{3-8}$-cycloalkylene, $B^1$ denotes phenyl or an aromatic or non-aromatic ring, which may optionally contain one, two, or three heteroatoms selected from among oxygen, sulfur, and nitrogen and which may optionally be mono- or polysubstituted by one or more groups selected from among OH, O—$C_{1-6}$-alkyl, O—$C_{1-6}$-haloalkyl, halogen, $C_{1-6}$-alkyl, and $C_{1-6}$-haloalkyl;

$B^2$ denotes phenyl or pyridinyl;

X denotes O, S, $NR^5$, or $CR^6R^7$;

n denotes 0, 1, 2, or 3;

$R^1$ denotes H, $C_{1-4}$-alkyl, or $C_{1-4}$-haloalkyl;

$R^2$ denotes H, $C_{1-4}$-alkyl, or $C_{1-4}$-haloalkyl; or $R^1$ and $R^2$ together with the nitrogen form a non-aromatic heterocycle, which may contain one or two nitrogen atoms;

$R^3$ denotes H, OH, $C_{1-6}$-haloalkyl, or a group selected from among $C_{6-10}$-aryl, a $C_{5-10}$-heteroaryl, and a $C_{3-10}$-heterocycle, which may optionally be substituted by a methyl group, oxo, or OH; or $R^3$ denotes $C_{1-6}$-alkyl, which may optionally be substituted by one or more groups selected from among halogen, OH, CN, $CONH_2$, CONH—$C_{1-6}$-alkyl, $CON(C_{1-6}$-alkyl$)_2$, COOH, COO—$C_{1-6}$-alkyl, COH, CO—$C_{1-6}$-alkyl, COaryl, OH, O—$C_{1-6}$-alkyl, O—$C_{1-6}$-haloalkyl, halogen, SH, S—$C_{1-6}$-alkyl, S—$C_{1-6}$-haloalkyl, $SO_2$—$C_{1-6}$-alkanol; $SO_2$—$C_{1-6}$-alkyl, $SO_2$—$C_{1-6}$-haloalkyl, $SO_2$—$NH_2$, $SO_2$—NH—$C_{1-6}$-alkyl, $SO_2$—$N(C_{1-6}$-alkyl$)_2$, $NO_2$, $NH_2$, NH—$C_{1-6}$-alkyl, and $N(C_{1-6}$-alkyl$)_2$; or $R^3$ denotes a group selected from among $C_{3-8}$-cycloalkyl, a $C_{3-8}$-cycloalkyl bridged with $C_{1-3}$-alkylene, a $C_{5-8}$-cycloalkenyl, $C_{1-6}$-alkyl, and $C_{1-6}$-alkanol, which may optionally be substituted by one or more groups selected from among $C_{6-10}$-aryl, $C_{3-8}$-cycloalkyl, $C_{5-10}$-heteroaryl, and a $C_{3-10}$-heterocycle, which may optionally be substituted by one or more groups selected from among $C_{1-6}$-alkyl, $C_{1-6}$-haloalkyl, CN, OH, O—$C_{1-6}$-alkyl, O—$C_{1-6}$-haloalkyl, halogen, S—$C_{1-6}$-alkyl, S—$C_{1-6}$-haloalkyl, NO$_2$, NH$_2$, NH—$C_{1-6}$-alkyl, N($C_{1-6}$-alkyl)$_2$, a $C_{5-10}$-heteroaryl, and a $C_{3-10}$-heterocycle, while the $C_{5-10}$-heteroaryl and the $C_{3-10}$-heterocycle may optionally be substituted by a group selected from oxo, hydroxyl, halogen, $C_{1-6}$-alkyl, and $C_{1-6}$-haloalkyl; or $R^3$ denotes a group selected from among $C_{1-6}$-alkyl, $C_{6-10}$-aryl-$C_{1-6}$-alkylene, $C_{5-10}$-heteroaryl-$C_{1-6}$-alkylene, $C_{3-7}$-cycloalkyl, $C_{6-10}$-aryl, $C_{5-10}$-heteroaryl, and a $C_{3-10}$-heterocycle, which is substituted by one or more groups selected from among B, halogen, OH, $C_{1-6}$-alkyl, oxo, where B is a compound of formula 2

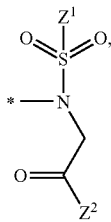

2 wherein:
$Z^1$ denotes H, OH, halogen, $C_{1-6}$-alkyl, $C_{1-6}$-alkanol, O($C_{1-6}$-alkyl), $C_{6-10}$-aryl, O—$C_{6-10}$-aryl, NH$_2$, NH($C_{1-6}$-alkyl), N($C_{1-6}$-alkyl)$_2$, or $C_{3-7}$-cycloalkyl; and $Z^2$ denotes OH, NH$_2$, NH($C_{1-6}$-alkyl), N($C_{1-6}$-alkyl)$_2$, O($C_{1-6}$-alkyl), mono- or bicyclic $C_{3-7}$-cycloalkyl, a mono- or bicyclic $C_{3-10}$-heterocycle, a mono- or bicyclic $C_{5-10}$-heteroaryl, or $C_{6-10}$-aryl; or $R^3$ denotes phenyl, which is substituted by one or more groups selected from among $C_{6-10}$-aryl, $C_{2-6}$-alkenyl, $C_{2-6}$-alkynyl, $C_{1-6}$-haloalkyl, CONH$_2$, CONH—$C_{1-6}$-alkyl, CON($C_{1-6}$-alkyl)$_2$, COOH, COO—$C_{1-6}$-alkyl, COH, CO—$C_{1-6}$-alkyl, COaryl, OH, O—$C_{1-6}$-alkyl, O—$C_{1-4}$-haloalkyl, halogen, SH, S—$C_{1-6}$-alkyl, S—$C_{1-4}$-haloalkyl, SO$_2$—$C_{1-6}$-alkyl, SO$_2$—$C_{1-4}$-haloalkyl, SO$_2$—NH$_2$, SO$_2$—NH—$C_{1-6}$-alkyl, SO$_2$—N($C_{1-6}$-alkyl)$_2$, NO$_2$, NO$_2$, NH$_2$, NH—$C_{1-6}$-alkyl, and N($C_{1-6}$-alkyl)$_2$; or $R^3$ denotes phenyl, which is substituted by $C_{1-4}$-alkyl, which may optionally be substituted by a group selected from among COOR$^{3.3}$, NR$^{3.3}$R$^{3.4}$ NHCOR$^{3.3}$, NHCOOR$^{3.3}$, and phenyl, which may optionally be substituted by one or more groups selected from among methyl, t-butyl, F, Cl, Br, CN, OH, and a heterocycle, which may contain one, two, or three heteroatoms selected from among oxygen and nitrogen, while the heterocycle may optionally be substituted by an oxo group or a methyl group, wherein: $R^{3.3}$ denotes H or $C_{1-6}$-alkyl; $R^{3.4}$ denotes H, $C_{1-6}$-alkyl, or $C_{6-10}$-aryl-$C_{1-6}$-alkylene, $C_{5-10}$-heteroaryl-$C_{1-6}$-alkylene; or $R^3$ denotes phenyl, substituted by NR$^{3.1}$R$^{3.2}$, wherein:
$R^{3.1}$ denotes H, $C_{1-4}$-alkyl, $C_{1-4}$-haloalkyl, COR$^{3.1.1}$, COOR$^{3.1.1}$, CONR$^{3.1.1}$R$^{3.1.2}$, or SO$_2$—R$^{3.1.1}$, wherein R$^{3.1.1}$ denotes H, $C_{1-4}$-alkyl, $C_{1-4}$-haloalkyl, $C_{3-6}$-cycloalkyl, or $C_{6-10}$-aryl; R$^{3.1.2}$ denotes H, $C_{1-4}$-alkyl, $C_{1-4}$-haloalkyl, $C_{3-6}$-cycloalkyl, or $C_{6-10}$-aryl; and
$R^{3.2}$ denotes H, $C_{1-4}$-alkyl, which may optionally be substituted by one or more groups selected from NH$_2$, NH($C_{1-4}$-alkyl), N($C_{1-4}$-alkyl)$_2$, oxo, or a non-aromatic $C_{3-10}$-heterocycle, which may contain one or two nitrogen atoms and may optionally be substituted by a methyl group; or $R^3$ denotes $C_{6-10}$-aryl, which may be substituted by a $C_{5-10}$-heteroaryl containing one, two, or three heteroatoms selected from among oxygen, sulfur, and nitrogen which may optionally be substituted by one or more groups selected from among $C_{6-10}$-aryl, $C_{1-4}$-alkyl, $C_{3-6}$-cycloalkyl, CN, $C_{1-4}$-haloalkyl, CONH$_2$, CONH—$C_{1-4}$-alkyl, CON($C_{1-4}$-alkyl)$_2$, COOH, COO—$C_{1-4}$-alkyl, COH, CO—$C_{1-4}$-alkyl, OH, O—$C_{1-4}$-alkyl, halogen, SH, S—$C_{1-4}$-alkyl, NH$_2$, NH—$C_{1-4}$-alkyl, and N($C_{1-4}$-alkyl)$_2$; or $R^3$ denotes $C_{6-10}$-aryl, which may be substituted by a non-aromatic $C_{3-10}$-heterocycle, which may contain one or two heteroatoms, selected from among oxygen, sulfur, and nitrogen, while the $C_{3-10}$-heterocycle may optionally be substituted by one or more groups selected from among $C_{1-4}$-alkyl and oxo; or $R^3$ denotes benzimidazolyl, which may optionally be substituted by one group or several groups selected from among $C_{1-4}$-alkyl, $C_{1-4}$-haloalkyl, and $C_{3-6}$-cycloalkyl;

$R^4$ denotes $C_{1-4}$-alkyl, $C_{3-6}$-cycloalkyl, $C_{1-4}$-haloalkyl, OR$^{4.1}$, NR$^{4.1}$R$^{4.2}$, CN, or halogen, wherein R$^{4.1}$ denotes H, $C_{1-4}$-alkyl, $C_{3-6}$-cycloalkyl, or $C_{1-4}$-haloalkyl; R$^{4.2}$ denotes H, $C_{1-4}$-alkyl, $C_{3-6}$-cycloalkyl, or $C_{1-4}$-haloalkyl;

$R^5$ denotes $C_{1-4}$-alkyl, $C_{3-8}$-cycloalkyl, $C_{1-4}$-haloalkyl, COR$^{5.1}$, CONHR$^{5.1}$, CON(R$^{5.1}$)$_2$, SO$_2$—$C_{1-4}$-alkyl, SO$_2$—$C_{1-4}$-haloalkyl, SO$_2$-aryl, or a group selected from among R$^{5.2}$, SO$_2$—$C_{1-4}$-alkyl-R$^{5.2}$, and $C_{1-4}$-alkyl-R$^{5.2}$, which may optionally be substituted by $C_{1-4}$-alkyl, $C_{2-4}$-alkenyl, $C_{2-4}$-alkynyl, CN, $C_{1-4}$-haloalkyl, CONH$_2$, CONH—$C_{1-4}$-alkyl, CON($C_{1-4}$-alkyl)$_2$, COOH, COO—$C_{1-4}$-alkyl, COH, CO—$C_{1-4}$-alkyl, O—$C_{1-4}$-cycloalkyl, O—$C_{1-4}$-halo alkyl, O—$C_{1-4}$-alkyl, halogen, SO$_2$—$C_{1-4}$-alkyl, SO$_2$—NH$_2$, SO$_2$—NH—$C_{1-4}$-alkyl, SO$_2$—N($C_{1-4}$-alkyl)$_2$, NO$_2$, NH$_2$, NH—$C_{1-4}$-alkyl, and N($C_{1-4}$-alkyl)$_2$, wherein R$^{5.1}$ denotes $C_{1-6}$-alkyl, $C_{5-10}$-heteroaryl-$C_{1-6}$-alkylene, or $C_{6-10}$-aryl-$C_{1-6}$-alkylene, and R$^{5.2}$ denotes $C_{6-10}$-aryl, or a $C_{5-10}$-heteroaryl;

$R^6$ denotes H, $C_{1-6}$-alkyl, or $C_{1-6}$-haloalkyl; and
$R^7$ denotes H, $C_{1-6}$-alkyl, or $C_{1-6}$-haloalkyl; or
$R^6$ and $R^7$ together form 3-6 membered carbocycle,
optionally in the form of the racemates, enantiomers, diastereomers, and optionally in the form of the pharmacologically acceptable acid addition salts, solvates, or hydrates thereof, as well as deuterated forms thereof.

Preferred compounds of formula 1 above are those wherein $R^1$, $R^2$, $R^4$, $R^5$, $R^6$, $R^7$, and A, B$^1$, B$^2$, X, and n have the meanings given above, and wherein:

$R^3$ denotes $C_{1-6}$-alkyl, which may optionally be substituted by one or more groups selected from among halogen, OH, CN, CONH$_2$, CONH—$C_{1-6}$-alkyl, CON($C_{1-6}$-alkyl)$_2$, COOH, COO—$C_{1-6}$-alkyl, COH, CO—$C_{1-6}$-alkyl, CO—$C_{6-10}$-aryl, OH, O—$C_{1-6}$-alkyl, O—$C_{1-6}$-haloalkyl, halogen, SH, S—$C_{1-6}$-alkyl, S—$C_{1-6}$-halo alkyl, SO$_2$—$C_{1-6}$-alkanol; SO$_2$—$C_{1-6}$-alkyl, SO$_2$—$C_{1-6}$-haloalkyl, SO$_2$—NH$_2$, SO$_2$—NH—$C_{1-6}$-alkyl, SO$_2$—N($C_{1-6}$-alkyl)$_2$, NO$_2$, NH$_2$, NH—$C_{1-6}$-alkyl, and N($C_{1-6}$-alkyl)$_2$, or $R^3$ denotes a group selected from among $C_{3-8}$-cycloalkyl, a $C_{3-8}$-cycloalkyl bridged with $C_{1-3}$-alkylene, a $C_{5-8}$-cycloalkenyl, $C_{1-6}$-alkyl, and $C_{1-6}$-alkanol, which may optionally be substituted by one or more groups selected from among $C_{6-10}$-aryl, $C_{3-8}$-cycloalkyl, a $C_{5-10}$-heteroaryl, and a $C_{3-10}$-heterocycle, which in turn may optionally be substituted by one or more groups selected from among $C_{1-6}$-alkyl, $C_{2-6}$-alkenyl, $C_{2-6}$-alkynyl, $C_{1-6}$-haloalkyl, CN, $CONH_2$, CONH—$C_{1-6}$-alkyl, CON($C_{1-6}$-alkyl)$_2$, COOH, COO—$C_{1-6}$-alkyl, COH, CO—$C_{1-6}$-alkyl, CO—$C_{6-10}$-aryl, OH, O—$C_{1-6}$-alkyl, O—$C_{1-6}$-haloalkyl, halogen, SH, S—$C_{1-6}$-alkyl, S—$C_{1-6}$-haloalkyl, $SO_2$—$C_{1-6}$-alkanol, $SO_2$—$C_{1-6}$-alkyl, $SO_2$—$C_{1-6}$-haloalkyl, $SO_2$—$NH_2$, $SO_2$—NH—$C_{1-6}$-alkyl, $SO_2$—N($C_{1-6}$-alkyl)$_2$, $NO_2$, $NH_2$, NH—$C_{1-6}$-alkyl, N($C_{1-6}$-alkyl)$_2$, $C_{5-10}$-heteroaryl, and a $C_{3-10}$-heterocycle, which may optionally be substituted by one or more groups selected from oxo, hydroxyl, halogen, or $C_{1-6}$-alkyl, and $C_{1-6}$-haloalkyl; or $R^3$ denotes a group selected from among $C_{6-10}$-aryl, $C_{5-10}$-heteroaryl, and a $C_{3-10}$-heterocycle, which may be substituted by one or more groups selected from among $C_{6-10}$-aryl, $C_{1-6}$-alkyl, $C_{2-6}$-alkenyl, $C_{2-6}$-alkynyl, $C_{1-6}$-haloalkyl, $CONH_2$, CONH—$C_{1-6}$-alkyl, CON($C_{1-6}$-alkyl)$_2$, COOH, COO—$C_{1-6}$-alkyl, COH, CO—$C_{1-6}$-alkyl, CO—$C_{6-10}$-aryl, OH, O—$C_{1-6}$-alkyl, O—$C_{1-6}$-haloalkyl, halogen, SH, S—$C_{1-6}$-alkyl, S—$C_{1-6}$-haloalkyl, $SO_2$—$C_{1-6}$-alkyl, $SO_2$—$C_{1-6}$-haloalkyl, $SO_2$—$NH_2$, $SO_2$—NH—$C_{1-6}$-alkyl, $SO_2$—N($C_{1-6}$-alkyl)$_2$, $NO_2$, $NH_2$, NH—$C_{1-6}$-alkyl, N($C_{1-6}$-alkyl)$_2$, and N—($SO_2$—$C_{1-4}$-alkyl)($R^{3.4}$); or $R^3$ denotes a group selected from among $C_{1-6}$-alkyl, $C_{6-10}$-aryl-$C_{1-6}$-alkylene, $C_{5-10}$-heteroaryl-$C_{1-6}$-alkylene, $C_{3-7}$-cycloalkyl, $C_{6-10}$-aryl, $C_{5-10}$-heteroaryl, and a $C_{3-10}$-heterocycle, which may optionally be substituted by one or more groups selected from among B, halogen, OH, $C_{1-6}$-alkyl, and oxo, while B is a compound of formula 2

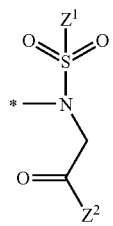

2 wherein:

$Z^1$ denotes H, OH, halogen, $C_{1-6}$-alkyl, $C_{1-6}$-alkanol, O($C_{1-6}$-alkyl), $C_{6-10}$-aryl, O—$C_{6-10}$-aryl, $NH_2$, NH($C_{1-6}$-alkyl), N($C_{1-6}$-alkyl)$_2$, or $C_{3-7}$-cycloalkyl, and $Z^2$ denotes OH, $NH_2$, NH($C_{1-6}$-alkyl), N($C_{1-6}$-alkyl)$_2$, O($C_{1-6}$-alkyl), mono- or bicyclic $C_{3-7}$-cycloalkyl, mono- or bicyclic $C_{5-10}$-heteroaryl, mono- or bicyclic $C_{3-10}$-heterocycle, or $C_{6-10}$-aryl, optionally in the form of the racemates, enantiomers, diastereomers thereof, and optionally in the form of the pharmacologically acceptable acid addition salts, solvates, or hydrates thereof, as well as deuterated forms thereof.

Preferred compounds of formula 1 above are those wherein $R^3$ and $R^4$ have the above-mentioned meanings and wherein A denotes $CH_2$, $CD_2$, C=NH, CHMe, $CMe_2$, 1,1'-cyclopropylene, or 1,1'-cyclobutylidene;

$B^1$ denotes phenyl;

$B^2$ denotes phenyl;

X denotes O or $NR^5$; wherein $R^5$ denotes methyl, ethyl, cyclopropyl, cyclobutyl, $CONHCH_2$-phenyl, $CH_2CF_3$, or benzyl, which may optionally be substituted by F; and wherein n denotes 0 or 1;

$R^1$ denotes H; and $R^2$ denotes H, optionally in the form of the racemates, enantiomers, diastereomers thereof, and optionally in the form of the pharmacologically acceptable acid addition salts, solvates, or hydrates thereof, as well as deuterated forms thereof.

Preferred are the above compounds of formula 1, wherein $R^1$, $R^2$, $R^5$, $R^6$, $R^7$, and A, $B^1$, $B^2$, X, and n have the meanings given above and wherein:

$R^3$ denotes $C_{1-6}$-alkyl, which may optionally be substituted by one or more groups selected from among halogen, OH, CN, $CONH_2$, CONH—$C_{1-6}$-alkyl, CON($C_{1-6}$-alkyl)$_2$, COOH, COO—$C_{1-6}$-alkyl, COH, CO—$C_{1-6}$-alkyl, CO—$C_{6-10}$-aryl, OH, O—$C_{1-6}$-alkyl, $SO_2$—$C_{1-6}$-alkanol; $SO_2$—$C_{1-6}$-haloalkyl, $SO_2$—$NH_2$, $SO_2$—NH—$C_{1-6}$-alkyl, $SO_2$—N($C_{1-6}$-alkyl)$_2$, $NO_2$, $NH_2$, NH—$C_{1-6}$-alkyl, and N($C_{1-6}$-alkyl)$_2$, or $R^3$ denotes a group selected from among $C_{3-8}$-cycloalkyl, a $C_{3-8}$-cycloalkyl bridged by $C_{1-3}$-alkylene and $C_{1-6}$-alkyl, which may optionally be substituted by one or more groups selected from among $C_{6-10}$-aryl, $C_{3-8}$-cycloalkyl, a $C_{5-10}$-heteroaryl, and a $C_{3-10}$-heterocycle, which may in turn optionally be substituted by one or more groups selected from among $C_{1-6}$-alkyl, $C_{2-6}$-alkenyl, $C_{2-6}$-alkynyl, $C_{1-6}$-haloalkyl, CN, $CONH_2$, CONH—$C_{1-6}$-alkyl, CON($C_{1-6}$-alkyl)$_2$, COOH, COO—$C_{1-6}$-alkyl, COH, CO—$C_{1-6}$-alkyl, CO—$C_{6-10}$-aryl, OH, O—$C_{1-6}$-alkyl, O—$C_{1-6}$-haloalkyl, halogen, SH, S—$C_{1-6}$-alkyl, $SO_2$—$C_{1-6}$-alkanol, $SO_2$—$C_{1-6}$-alkyl, $SO_2$—$C_{1-6}$-haloalkyl, $SO_2$—$NH_2$, $SO_2$—NH—$C_{1-6}$-alkyl, $SO_2$—N($C_{1-6}$-alkyl)$_2$, $NO_2$, $NH_2$, NH—$C_{1-6}$-alkyl, N($C_{1-6}$-alkyl)$_2$, $C_{5-10}$-heteroaryl, and a $C_{3-10}$-heterocycle, which may optionally be substituted by one or more groups selected from oxo, hydroxyl, halogen, or $C_{1-6}$-alkyl, and $C_{1-6}$-haloalkyl; or $R^3$ denotes a group selected from among $C_{6-10}$-aryl, a $C_{3-8}$-heterocycle with 1 to 4 heteroatoms selected from N, O, S, and a $C_{5-10}$-heteroaryl with 1 to 2 heteroatoms selected from N, O, S, which may optionally be substituted by one or more groups selected from among $C_{6-10}$-aryl, $C_{1-6}$-alkyl, $C_{1-6}$-haloalkyl, $CONH_2$, CONH—$C_{1-6}$-alkyl, CON($C_{1-6}$-alkyl)$_2$, COOH, COO—$C_{1-6}$-alkyl, COH, CO—$C_{1-6}$-alkyl, CO—$C_{6-10}$-aryl, OH, O—$C_{1-6}$-alkyl, O—$C_{1-6}$-haloalkyl, halogen, $SO_2$—$C_{1-6}$-alkyl, $SO_2$—$C_{1-6}$-alkanol, $SO_2$—$C_{1-6}$-haloalkyl, $SO_2$—$NH_2$, $SO_2$—NH—$C_{1-6}$-alkyl, $SO_2$—N($C_{1-6}$-alkyl)$_2$, $NO_2$, $NH_2$, NH—$C_{1-6}$-alkyl, N($C_{1-6}$-alkyl)$_2$, and N—($SO_2$—$C_{1-4}$-alkyl)($R^{3.4}$), wherein $R^{3.4}$ is a $C_{5-10}$-heteroaryl-$C_{1-6}$-alkylene; or $R^3$ denotes a group selected from among $C_{1-6}$-alkyl, $C_{6-10}$-aryl-$C_{1-6}$-alkylene, $C_{5-10}$-heteroaryl-$C_{1-6}$-alkylene, $C_{3-7}$-cycloalkyl, $C_{6-10}$-aryl, $C_{3-8}$-heterocycle with 1 to 4 heteroatoms selected from N, O, S, and a $C_{5-10}$-heteroaryl with 1 to 2 heteroatoms selected from N, O, S, which may optionally be substituted in each case by one or more groups selected from among B, halogen, OH, $C_{1-6}$-alkyl, oxo, wherein B is a compound of formula 2

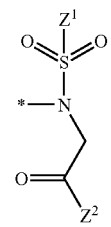

2 wherein:

$Z^1$ is H, OH, halogen, $C_{1-6}$-alkyl, $C_{1-6}$-alkanol, or O($C_{1-6}$-alkyl) and $Z^2$ is OH, $NH_2$, $NH(C_{1-6}$-alkyl), $N(C_{1-6}$-alkyl)$_2$, $O(C_{1-6}$-alkyl), mono- or bicyclic $C_{3-7}$-cycloalkyl, mono- or bicyclic $C_{5-10}$-heteroaryl, mono- or bicyclic $C_{3-10}$-heterocycle, or $C_{6-10}$-aryl; and $R^4$ denotes H, F, or Cl, optionally in the form of the racemates, enantiomers, diastereomers, and optionally in the form of the pharmacologically acceptable acid addition salts, solvates, or hydrates thereof, as well as deuterated forms thereof.

Preferred are the above compounds of formula 1, wherein
A denotes CO, C=NH, $C_{1-6}$-alkylene, or $C_{3-8}$-cycloalkylene,
$B^1$ denotes phenyl or pyridinyl;
$B^2$ denotes phenyl or pyridinyl;
X denotes O or $NR^5$;
n denotes 0, 1, 2, or 3;
$R^1$ denotes H, methyl, ethyl, or propyl;
$R^2$ denotes H, methyl, ethyl, or propyl;
$R^3$ denotes H, OH, $C_{1-6}$-haloalkyl, or $C_{6-10}$-aryl, or a group selected from among a $C_{5-10}$-heteroaryl and a $C_{3-10}$-cycloalkyl, which may contain one, two, or three nitrogen atoms and which may optionally be substituted by a methyl group; or $R^3$ denotes a group selected from among cyclopentyl, cyclohexyl, cyclopentenyl, cyclohexenyl, methyl, ethyl, propyl, and butyl, which may optionally be substituted by one or more groups selected from among $C_{6-10}$-aryl and a $C_{5-10}$-heterocycle, which may in turn optionally be substituted by one or more groups selected from among $C_{1-6}$-alkyl, $C_{1-6}$-haloalkyl, CN, OH, O—$C_{1-6}$-alkyl, O—$C_{1-6}$-haloalkyl, halogen, S—$C_{1-6}$-alkyl, S—$C_{1-6}$-haloalkyl, $NO_2$, $NH_2$, NH—$C_{1-6}$-alkyl, and $N(C_{1-6}$-alkyl)$_2$; or $R^3$ denotes phenyl, which may optionally be substituted by one or more groups selected from among $C_{6-10}$-aryl, $C_{2-4}$-alkenyl, $C_{2-4}$-alkynyl, $C_{1-4}$-haloalkyl, $CONH_2$, CONH—$C_{1-4}$-alkyl, CON($C_{1-4}$-alkyl)$_2$, COOH, COO—$C_{1-4}$-alkyl, COH, CO—$C_{1-4}$-alkyl, CO—$C_{6-10}$-aryl, OH, O—$C_{1-4}$-alkyl, O—$C_{1-4}$-haloalkyl, halogen, SH, S—$C_{1-4}$-alkyl, S—$C_{1-4}$-haloalkyl, $SO_2$—$C_{1-4}$-alkyl, $SO_2$—$C_{1-4}$-haloalkyl, $SO_2$—$NH_2$, $SO_2$—NH—$C_{1-4}$-alkyl, $SO_2$—N($C_{1-4}$-alkyl)$_2$, $NO_2$, $NO_2$, $NH_2$, NH—$C_{1-4}$-alkyl, and $N(C_{1-4}$-alkyl)$_2$; or $R^3$ denotes phenyl, which may optionally be substituted by $C_{1-4}$-alkyl, which may in turn optionally be substituted by a group selected from among $COOR^{3.3}$, $NR^{3.3}R^{3.4}$, $NHCOR^{3.3}$, $NHCOOR^{3.3}$, p-fluorophenyl, and a heterocycle, which may contain one, two, or three heteroatoms selected from among oxygen and nitrogen and which may optionally be substituted by an oxo group, wherein $R^{3.3}$ denotes H or $C_{1-4}$-alkyl; and $R^{3.4}$ denotes H, $C_{1-4}$-alkyl, $C_{6-10}$-aryl-$C_{1-6}$-alkylene, or $C_{5-10}$-heteroaryl-$C_{1-6}$-alkylene; or $R^3$ denotes phenyl, which may be substituted by $NR^{3.1}R^{3.2}$, wherein:

$R^{3.1}$ denotes H, $C_{1-4}$-alkyl, $COR^{3.1.1}$, $COOR^{3.1.1}$, $CONR^{3.1.1}R^{3.1.2}$ or $SO_2$—$R^{3.1.1}$, wherein $R^{3.1.1}$ denotes H, $C_{1-4}$-alkyl, or $C_{6-10}$-aryl, and $R^{3.1.2}$ denotes H, $C_{1-4}$-alkyl, or $C_{6-10}$-aryl, and $R^{3.2}$ denotes H, $C_{1-4}$-alkyl, which may optionally be substituted by one or more groups selected from among $NH_2$, $NH(C_{1-4}$-alkyl), $N(C_{1-4}$-alkyl)$_2$, oxo, or a $C_{3-10}$-heterocycle, which may contain one or two nitrogen atoms and which may optionally be substituted by a methyl group; or $R^3$ denotes phenyl, which may be substituted by a $C_{5-10}$-heteroaryl, which may contain one, two, or three heteroatoms selected from among oxygen, sulfur, and nitrogen, while the $C_{5-10}$-heteroaryl may optionally be substituted by one or more groups selected from among $C_{6-10}$-aryl, $C_{1-4}$-alkyl, $C_{1-4}$-haloalkyl, $C_{3-6}$-cycloalkyl, CN, $CONH_2$, to CONH—$C_{1-4}$-alkyl, CON($C_{1-4}$-alkyl)$_2$, COOH, COO—$C_{1-4}$-alkyl, COH, CO—$C_{1-4}$-alkyl, OH, O—$C_{1-4}$-alkyl, halogen, $NH_2$, and $N(C_{1-4}$-alkyl)$_2$; or $R^3$ denotes phenyl, which may be substituted by a $C_{5-10}$-heteroaryl, which may contain one, two, or three heteroatoms selected from among oxygen, sulfur, and nitrogen, while the $C_{5-10}$-heteroaryl may optionally be substituted by one or more groups selected from among $C_{1-4}$-alkyl and oxo; or $R^3$ denotes benzimidazolyl, which may optionally be substituted by one or more groups selected from among methyl, ethyl, propyl, $CF_3$, $CH_2CF_3$, cyclopropyl, cyclopentyl, and cyclohexyl;

$R^4$ denotes $C_{1-4}$-alkyl, $C_{1-4}$-haloalkyl, or halogen; and $R^5$ denotes a group selected from among $C_{1-4}$-alkyl, $C_{3-6}$-cycloalkyl, $COR^{5.1}$, $CONHR^{5.1}$, $C_{6-10}$-aryl, $SO_2$—$C_{6-10}$-aryl-$C_{1-6}$-alkylene, $SO_2$—$C_{6-10}$-aryl, or $C_{6-10}$-aryl-$C_{1-6}$-alkylene, and $C_{5-10}$-heteroaryl-$C_{1-6}$-alkylene, which may optionally be substituted by one or more groups selected from among $C_{1-4}$-alkyl, $C_{2-4}$-alkenyl, $C_{2-4}$-alkynyl, CN, $C_{1-4}$-haloalkyl, $CONH_2$, CONH—$C_{1-4}$-alkyl, CON($C_{1-4}$-alkyl)$_2$, COOH, COO—$C_{1-4}$-alkyl, COH, CO—$C_{1-4}$-alkyl, OH, O—$C_{1-4}$-alkyl, halogen, $SO_2$—$C_{1-4}$-alkyl, $SO_2$—$NH_2$, $SO_2$—NH—$C_{1-4}$-alkyl, $SO_2$—N($C_{1-4}$-alkyl)$_2$, $NO_2$, $NH_2$, NH—$C_{1-4}$-alkyl, and $N(C_{1-4}$-alkyl)$_2$; and $R^{5.1}$ denotes $C_{1-4}$-alkyl, or $C_{6-10}$-aryl-$C_{1-6}$-alkylene, optionally in the form of the racemates, enantiomers, diastereomers, and optionally in the form of the pharmacologically acceptable acid addition salts, solvates, or hydrates thereof, as well as deuterated forms thereof.

Particularly preferred are the compounds of formula 1a

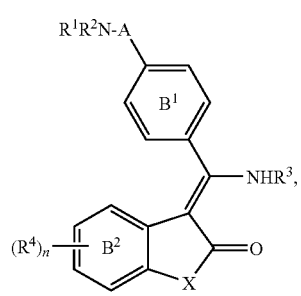

1a wherein A, X, n, $R^1$, $R^2$, $R^3$, and $R^4$ are as hereinbefore defined, optionally in the form of the racemates, enantiomers, diastereomers, and optionally in the form of the pharmacologically acceptable acid addition salts, solvates, or hydrates thereof, as well as deuterated forms thereof.

Particularly preferred are the above compounds of formula 1 or 1a, wherein $R^1$, $R^2$, $R^3$, $R^4$, and A, $B^1$, $B^2$, and n have the meanings given above and wherein X denotes O, optionally in the form of the racemates, enantiomers, diastereomers, and optionally in the form of the pharmacologically acceptable acid addition salts, solvates, or hydrates thereof, as well as deuterated forms thereof.

Particularly preferred are the above compounds of formula 1 or 1a, wherein $R^1$, $R^2$, $R^3$, $R^4$, $R^5$, and A, $B^1$, $B^2$, and n have the meanings given above and wherein X denotes $NR^5$, optionally in the form of the racemates, enantiomers, diastereomers, and optionally in the form of the pharmacologically acceptable acid addition salts, solvates, or hydrates thereof, as well as deuterated forms thereof.

Particularly preferred are the above compounds of formula 1 or 1a, wherein $R^1$, $R^2$, $R^3$, $R^4$, $R^6$, and $R^7$ as well as A, $B^1$, $B^2$, and n have the meanings given above and wherein X denotes $CR^6R^7$, optionally in the form of the racemates, enantiomers, diastereomers, and optionally in the form of the pharmacologically acceptable acid addition salts, solvates, or hydrates thereof, as well as deuterated forms thereof.

Particularly preferred are the above compounds of formula 1 or 1a, wherein $R^1$, $R^2$, $R^3$, $R^4$, $R^5$, $R^6$, $R^7$ as well as A, $B^1$, $B^2$, and X have the meanings given above and wherein n denotes 0, 1, or 2, preferably 0 or 1, particularly preferably 0, optionally in the form of the racemates, enantiomers, diastereomers, and optionally in the form of the pharmacologically acceptable acid addition salts, solvates, or hydrates thereof, as well as deuterated forms thereof.

Particularly preferred are the above compounds of formula 1 or 1a, wherein:

A denotes $CH_2$, CHMe, $CMe_2$, C=NH, 1,1'-cyclopropylene, 1,1'-cyclobutylidene;
$B^1$ denotes phenyl;
$B^2$ denotes phenyl;
X denotes O or $NR^5$;
n denotes 0, 1, or 2;
$R^1$ denotes H, methyl, or ethyl;
$R^2$ denotes H, methyl, or ethyl;
$R^3$ denotes H, cyclopropyl, cyclobutyl, N-methylpiperidinyl, pyridinyl, phenyl, or 4-phenylcyclohexanyl, or
$R^3$ denotes phenyl, which may optionally be substituted by one or more groups selected from among phenyl, methyl, ethyl, propyl, butyl, $CF_3$, $CONH_2$, CONHMe, $CONMe_2$, COOH, COOMe, COOEt, COH, COMe, OH, OMe, OEt, F, Cl, Br, SH, $SO_2Me$, $SONH_2$, $SONMe_2$, $NO_2$, $NH_2$, NHMe, and $NMe_2$; or
$R^3$ denotes phenyl, which is optionally substituted by a group selected from among methyl and ethyl, which may optionally be substituted by one or more groups selected from among COOH, COOMe, $NH_2$, $NMe_2$, NHCOMe, NHCOO-tert-butyl, NMe(benzyl), p-fluorophenyl, pyrrolidinyl, piperidinyl, morpholinyl, pyrrolidin-2-onyl, imidazolyl, and triazolyl; or
$R^3$ denotes phenyl, which is substituted by $NR^{3.1}R^{3.2}$, wherein $R^{3.1}$ denotes H, methyl, COH, COMe, COOMe, $CONH_2$, $CONMe_2$, $SO_2Me$, $SO_2CF_3$, or $SO_2$-phenyl, and $R^{3.2}$ denotes H or a group selected from among methyl and ethyl, which may optionally be substituted by one or more groups selected from among $NH_2$, NHMe, $NMe_2$, N-piperidinyl, N-morpholinyl, and N-methylpiperazinyl, wherein the N-piperidinyl, N-morpholinyl, and the N-methylpiperazinyl may optionally be substituted by a further oxo; or
$R^3$ denotes phenyl, which may be substituted by a $C_{5-10}$-heteroaryl, which may contain one, two, or three heteroatoms selected from among oxygen, sulfur, and nitrogen, while the $C_{5-10}$-heteroaryl may optionally be substituted by one or more groups selected from among phenyl, methyl, ethyl, propyl, butyl, cyclopropyl, cyclobutyl, $CF_3$, CN, $CONH_2$, $CONMe_2$, $CONEt_2$, COOH, COOMe, COOEt, COH, COMe, OH, OMe, OEt, F, Cl, Br, $NH_2$, $NMe_2$, $NEt_2$, and $NPr_2$; or
$R^3$ denotes phenyl which is substituted by a $C_{3-10}$-heterocycle, which may contain one or two heteroatoms selected from among oxygen and nitrogen, while the $C_{3-10}$-heterocycle may optionally be substituted by one or more groups selected from among $C_{1-4}$-alkyl and oxo; or
$R^3$ denotes benzimidazolyl, which may optionally be substituted by one or more groups selected from among methyl, propyl, $CF_3$, $CH_2CF_3$, cyclopropyl, and cyclohexyl;
$R^4$ denotes methyl, ethyl, propyl, butyl, $CF_3$, $CH_2CF_3$, F, Cl, or Br; and
$R^5$ denotes a group selected from among methyl, ethyl, propyl, butyl, cyclopropyl, cyclobutyl, $CF_3$, $CH_2CF_3$, $COR^{5.1}$, $CONHR^{5.1}$, phenyl, phenylsulfonyl, and benzyl, while benzyl may optionally be substituted by one or more groups selected from among methyl, ethyl, propyl, butyl, $CF_3$, CN, $CONH_2$, $CONMe_2$, $CONEt_2$, COOH, COOMe, COOEt, COH, COMe, OH, OMe, OEt, F, Cl, Br, $SO_2Me$, $SONH_2$, $SONMe_2$, $NO_2$, $NH_2$, $NMe_2$, $NEt_2$, and $NPr_2$, wherein $R^{5.1}$ denotes methyl, ethyl, propyl, butyl, or benzyl,
optionally in the form of the racemates, enantiomers, diastereomers thereof, and optionally in the form of the pharmacologically acceptable acid addition salts, solvates, or hydrates thereof, as well as deuterated forms thereof.

Particularly preferred are the above compounds of formula 1 or 1a, wherein:

A denotes $CH_2$, CHMe, $CMe_2$, CO, C=NH, 1,1'-cyclopropylene, or 1,1'-cyclobutylidene;
$B^1$ denotes phenyl;
$B^2$ denotes phenyl;
X denotes O or $NR^5$;
n denotes 0 or 1;
$R^1$ denotes H, methyl, or ethyl, preferably H;
$R^2$ denotes H, methyl, or ethyl, preferably H;
$R^3$ denotes H, OH, cyclopropyl, cyclobutyl, N-methylpiperidinyl, pyridinyl, phenyl, or 4-phenylcyclohexanyl, or
$R^3$ denotes phenyl, which may be substituted by a group selected from among phenyl, OH, F, and $CONH_2$; or
$R^3$ denotes phenyl, which is substituted by a group selected from among methyl and ethyl, which may optionally be substituted by a group selected from among COOH, COOMe, $NH_2$, $NMe_2$, NHCOMe, NHCOO-tert-butyl, NMe(benzyl), p-fluorophenyl, pyrrolidinyl, piperidinyl, morpholinyl, pyrrolidin-2-onyl, imidazolyl, and triazolyl; or
$R^3$ denotes phenyl, which is substituted by $NR^{3.1}R^{3.2}$, wherein $R^{3.1}$ denotes H, methyl, $SO_2Me$, $SO_2CF_3$, or $SO_2$-phenyl; $R^{3.2}$ denotes H or a group selected from among methyl and ethyl, which may optionally be substituted by one or more groups selected from among $NH_2$, NHMe, $NMe_2$, oxo, N-piperidinyl, N-morpholinyl, and N-methylpiperazinyl; or
$R^3$ denotes phenyl, which may be substituted by a $C_{5-10}$-heteroaryl, which may contain one, two, or three heteroatoms selected from among oxygen, sulfur, and nitrogen and which may optionally be substituted by one or more groups selected from among phenyl, methyl, ethyl, propyl, butyl, cyclopropyl, cyclobutyl, $CF_3$, CN, $CONH_2$, $CONMe_2$, $CONEt_2$, COOH, COOMe, COOEt, COH, COMe, OH, OMe, OEt, F, Cl, Br, $SO_2Me$, $SONH_2$, $SONMe_2$, $NO_2$, $NH_2$, $NMe_2$, $NEt_2$, and $NPr_2$, or
$R^3$ denotes phenyl, which is substituted by a $C_{3-10}$-heterocycle which may contain one or two heteroatoms selected from among oxygen and nitrogen and may optionally be substituted by one or more groups selected from among $C_{1-4}$-alkyl and oxo, or
$R^3$ denotes benzimidazolyl, which may optionally be substituted by methyl;
$R^4$ denotes F or Cl; and
$R^5$ denotes a group selected from among methyl, ethyl, cyclopropyl, COMe, $CONHR^{5.1}$, phenyl, phenylsulfonyl, and benzyl, which may optionally be substituted by F, wherein $R^{5.1}$ denotes butyl or benzyl,
optionally in the form of the racemates, enantiomers, diastereomers, and optionally in the form of the pharmacologically acceptable acid addition salts, solvates, or hydrates thereof, as well as deuterated forms thereof.

Particularly preferred are the above compounds of formula 1 or 1a, wherein:

A denotes $CH_2$, CHMe, $CMe_2$, 1,1'-cyclopropylene, 1,1'-cyclobutylidene;

$B^1$ denotes phenyl;

$B^2$ denotes phenyl;

X denotes O or $NR^5$;

n denotes 0 or 1;

$R^1$ denotes H;

$R^2$ denotes H;

$R^3$ denotes H or 4-phenylcyclohexanyl; or $R^3$ denotes phenyl, which may optionally be substituted by $NR^{3.1}R^{3.2}$, wherein $R^{3.1}$ denotes H, methyl, $SO_2Me$, $SO_2CF_3$, or $SO_2$-phenyl; and $R^{3.2}$ denotes H or a group selected from among methyl and ethyl, which may optionally be substituted by one or more groups selected from among $NH_2$, NHMe, $NMe_2$, oxo, N-piperidinyl, N-morpholinyl, and N-methylpiperazinyl, or $R^3$ denotes phenyl, which is substituted by a $C_{5-10}$-heteroaryl, which may contain one, two, or three heteroatoms selected from among oxygen, sulfur, and nitrogen, while the $C_{5-10}$-heteroaryl may optionally be substituted by one or more groups selected from among phenyl, methyl, ethyl, propyl, butyl, cyclopropyl, cyclobutyl, $CF_3$, CN, $CONH_2$, $CONMe_2$, $CONEt_2$, COOH, COOMe, COOEt, COH, COMe, OH, OMe, OEt, F, Cl, Br, $SO_2Me$, $SONH_2$, $SONMe_2$, $NO_2$, $NH_2$, $NMe_2$, $NEt_2$, and $NPr_2$, or $R^3$ denotes phenyl, which is substituted by a $C_{3-10}$-heterocycle, which may contain one or two heteroatoms selected from among oxygen and nitrogen, while the $C_{3-10}$-heterocycle may optionally be substituted by one or more groups selected from among $C_{1-4}$-alkyl and oxo;

$R^4$ denotes H, F, or Cl; and $R^5$ denotes methyl, ethyl, cyclopropyl, cyclobutyl, $CH_2CF_3$, or benzyl, while the benzyl may optionally be substituted by F, optionally in the form of the racemates, enantiomers, diastereomers, and optionally in the form of the pharmacologically acceptable acid addition salts, solvates, or hydrates thereof, as well as deuterated forms thereof.

Also particularly preferred are the above compounds of formula 1 or 1a, wherein:

A denotes a group selected from among $CH_2$, CHMe, $CMe_2$, CO, C=NH, and

$B^1$ denotes phenyl;

$B^2$ denotes phenyl;

X denotes O or $NR^5$;

n denotes 0 or 1;

$R^1$ denotes H;

$R^2$ denotes H;

$R^3$ denotes H, OH, 4-phenylcyclohexyl, or a group selected from among

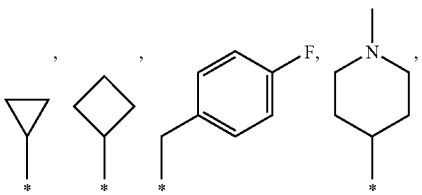

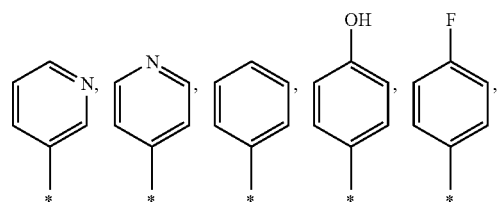

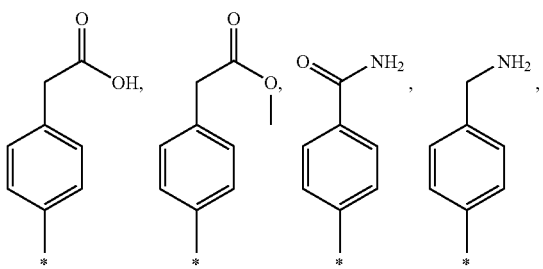

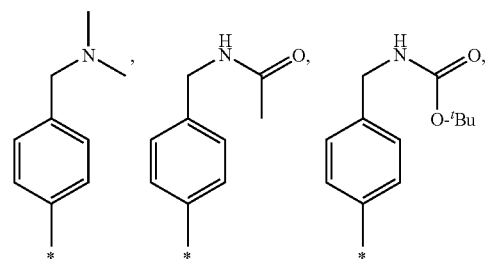

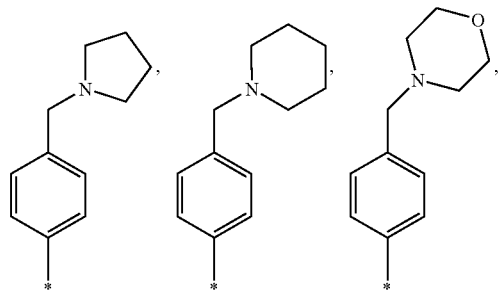

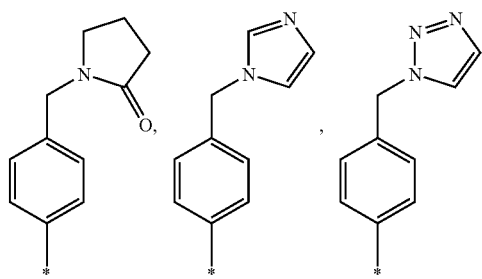

17
-continued
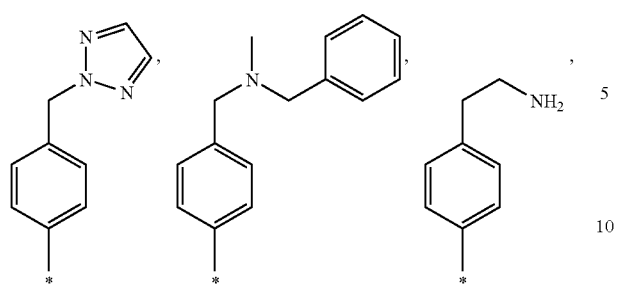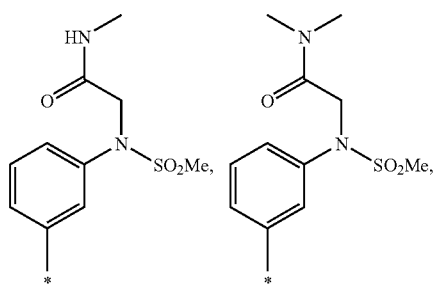
18
-continued
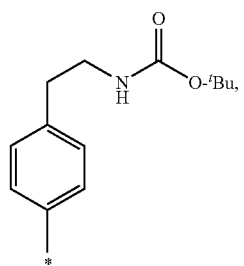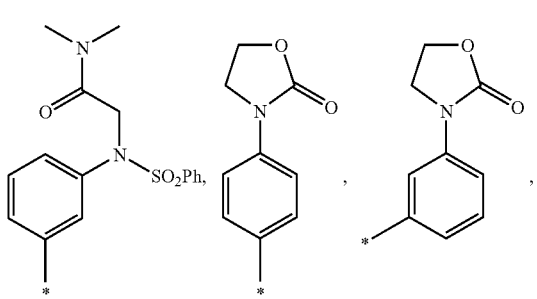
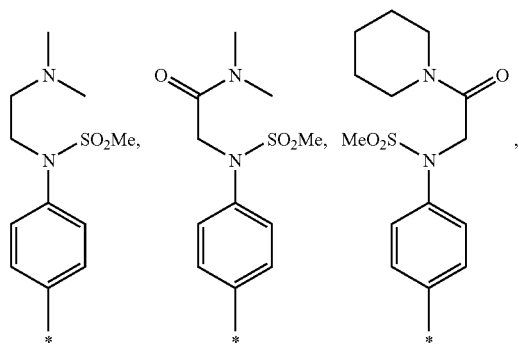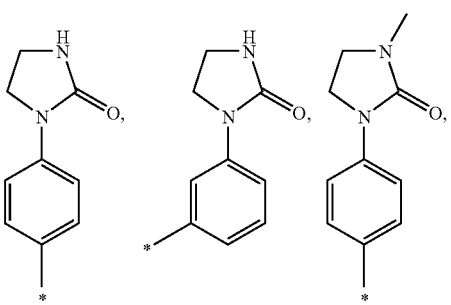
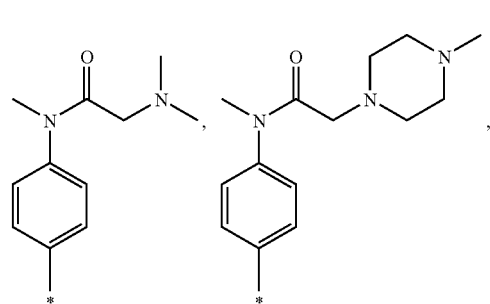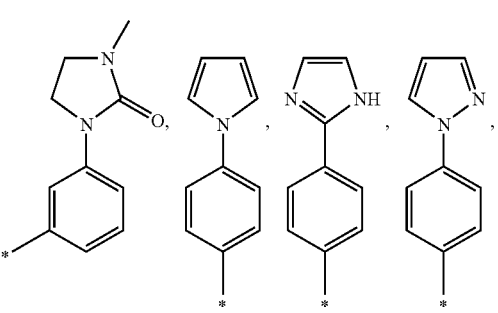
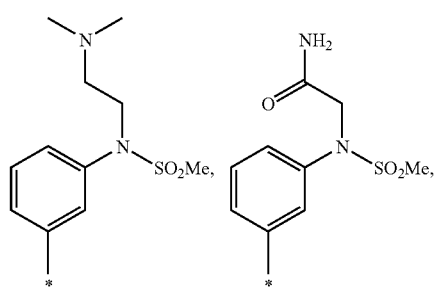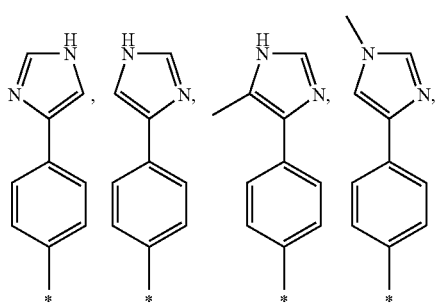

-continued

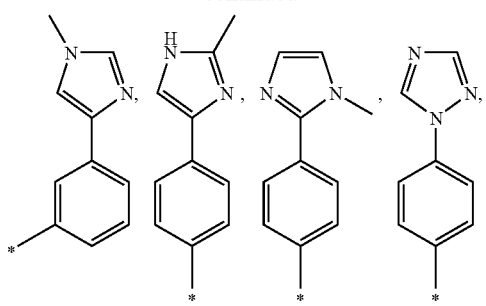
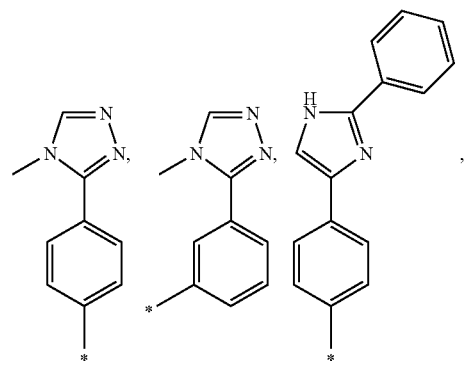
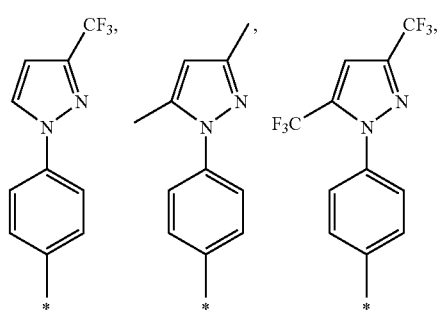
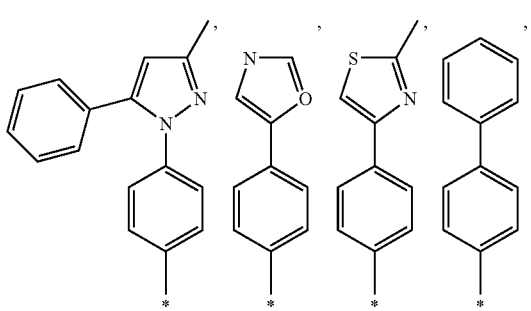
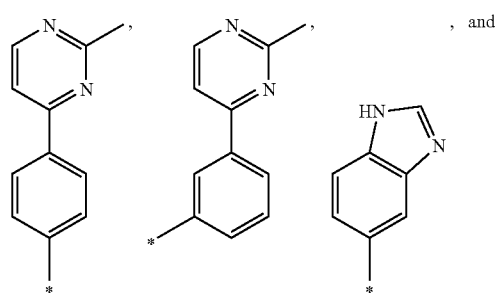

-continued

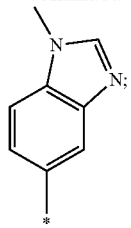

$R^4$ denotes H, F, or Cl; and
$R^5$ denotes methyl or a group selected from among

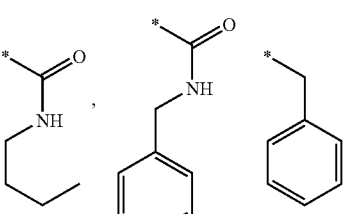
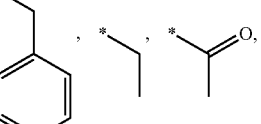
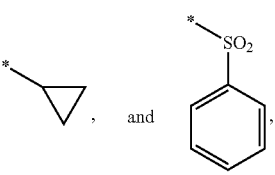

optionally in the form of the racemates, enantiomers, diastereomers thereof, and optionally in the form of the pharmacologically acceptable acid addition salts, solvates, or hydrates thereof, as well as deuterated forms thereof.

Also particularly preferred are the above compounds of formula 1 or 1a, wherein:
A denotes $CH_2$, $CD_2$, C=NH, CHMe, $CMe_2$, 1,1'-cyclopropylene, 1,1'-cyclobutylidene;
$B^1$ denotes phenyl;
$B^2$ denotes phenyl;
X denotes O or $NR^5$, wherein $R^5$ denotes methyl, ethyl, cyclopropyl, cyclobutyl, $CONHCH_2$-phenyl, $CH_2CF_3$, or benzyl, optionally substituted by F;
n denotes 0 or 1;
$R^1$ denotes H;
$R^2$ denotes H;
$R^3$ denotes $C_{1-6}$-alkyl, optionally substituted by one or more groups selected from among halogen, OH, CN, $CONH_2$, CONH—$C_{1-6}$-alkyl, $CON(C_{1-6}$-alkyl$)_2$, COOH, COO—$C_{1-6}$-alkyl, COH, CO—$C_{1-6}$-alkyl, COaryl, OH, O—$C_{1-6}$-alkyl, O—$C_{1-6}$-haloalkyl, halogen, SH, S—$C_{1-6}$-alkyl, S—$C_{1-6}$-haloalkyl, $SO_2$—$C_{1-6}$-alkanol; $SO_2$—$C_{1-6}$-alkyl, $SO_2$—$C_{1-6}$-haloalkyl, $SO_2$—$NH_2$, $SO_2$—NH—$C_{1-6}$-alkyl, $SO_2$—$N(C_{1-6}$-alkyl$)_2$, $NO_2$, $NH_2$, NH—$C_{1-6}$-alkyl, and $N(C_{1-6}$-alkyl$)_2$, or
$R^3$ denotes a group selected from among $C_{3-8}$-cycloalkyl, a $C_{3-8}$-cycloalkyl bridged by $C_{1-3}$-alkylene, or $C_{5-8}$-cycloalkenyl, and $C_{1-6}$-alkyl, $C_{1-6}$-alkanol, which may optionally be substituted in each case by one or more groups selected from among $C_{6-10}$-aryl, $C_{3-8}$-cycloalkyl, $C_{5-10}$-heteroaryl, and $C_{3-10}$-heterocycle, which may optionally be substituted by one or more groups selected from among $C_{1-6}$-alkyl, $C_{2-6}$-alkenyl, $C_{2-6}$-alkynyl, $C_{1-6}$- haloalkyl, CN, CONH$_2$, CONH—C$_{1-6}$-alkyl, CON(C$_{1-6}$-alkyl)$_2$, COOH, COO—C$_{1-6}$-alkyl, COH, CO—C$_{1-6}$-alkyl, CO—C$_{6-10}$-aryl, OH, O—C$_{1-6}$-alkyl, O—C$_{1-6}$-haloalkyl, halogen, SH, S—C$_{1-6}$-alkyl, S—C$_{1-6}$-haloalkyl, SO$_2$—C$_{1-6}$-alkanol, SO$_2$—C$_{1-6}$-alkyl, SO$_2$—C$_{1-6}$-haloalkyl, SO$_2$—NH$_2$, SO$_2$—NH—C$_{1-6}$-alkyl, SO$_2$—N(C$_{1-6}$-alkyl)$_2$, NO$_2$, NH$_2$, NH—C$_{1-6}$-alkyl, N(C$_{1-6}$-alkyl)$_2$, C$_{5-10}$-heteroaryl, and a C$_{3-10}$-heterocycle, which may optionally be substituted by a group selected from oxo, hydroxyl, halogen, or C$_{1-6}$-alkyl, and C$_{1-6}$-haloalkyl; or R$^3$ denotes a group selected from among C$_{6-10}$-aryl, C$_{5-10}$-heteroaryl, and a C$_{3-10}$-heterocycle, which may be substituted in each case by one or more groups selected from among C$_{6-10}$-aryl, C$_{2-6}$-alkenyl, C$_{2-6}$-alkynyl, C$_{1-6}$-haloalkyl, CONH$_2$, CONH—C$_{1-6}$-alkyl, CON(C$_{1-6}$-alkyl)$_2$, COOH, COO—C$_{1-6}$-alkyl, COH, CO—C$_{1-6}$-alkyl, CO—C$_{6-10}$-aryl, OH, O—C$_{1-6}$-alkyl, O—C$_{1-6}$-haloalkyl, halogen, SH, S—C$_{1-6}$-alkyl, S—C$_{1-6}$-halo alkyl, SO$_2$—C$_{1-6}$-alkyl, SO$_2$—C$_{1-6}$-alkanol, SO$_2$—C$_{1-6}$-halo alkyl, SO$_2$—NH$_2$, SO$_2$—NH—C$_{1-6}$-alkyl, SO$_2$—N(C$_{1-6}$-alkyl)$_2$, NO$_2$, NH$_2$, NH—C$_{1-6}$-alkyl, N(C$_{1-6}$-alkyl)$_2$, and N—(SO$_2$—C$_{1-4}$-alkyl)(R$^{3.4}$), wherein R$^{3.4}$ is a C$_{6-10}$-aryl, C$_{6-10}$-aryl-C$_{1-6}$-alkylene, or a C$_{5-10}$-heteroaryl-C$_{1-6}$-alkylene; or R$^3$ denotes a group selected from among C$_{1-6}$-alkyl, C$_{6-10}$-aryl-C$_{1-6}$-alkylene, C$_{5-10}$-heteroaryl-C$_{1-6}$-alkylene, C$_{3-7}$-cycloalkyl, C$_{6-10}$-aryl, C$_{5-10}$-heteroaryl, and a C$_{3-10}$-heterocycle, which may optionally be substituted in each case by one or more groups selected from among B, halogen, OH, C$_{1-6}$-alkyl, oxo, where B is a compound of formula 2

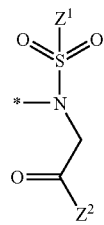

2 wherein Z$^1$ denotes H, OH, halogen, C$_{1-6}$-alkyl, C$_{1-6}$-alkanol, O(C$_{1-6}$-alkyl), C$_{6-10}$-aryl, O—C$_{6-10}$-aryl, NH$_2$, NH(C$_{1-6}$-alkyl), N(C$_{1-6}$-alkyl)$_2$, or C$_{3-7}$-cycloalkyl; and Z$^2$ OH, NH$_2$, NH(C$_{1-6}$-alkyl), N(C$_{1-6}$-alkyl)$_2$, C$_{6-10}$-aryl; mono- or bicyclic C$_{3-7}$-cycloalkyl, mono- or bicyclic aromatic or non-aromatic C$_{3-10}$-heterocycle, and R$^4$ denotes H, F, or Cl, optionally in the form of the racemates, enantiomers, diastereomers thereof, and optionally in the form of the pharmacologically acceptable acid addition salts, solvates, or hydrates thereof, as well as deuterated forms thereof.

Also particularly preferred are compounds of formula 1 or 1a, wherein:

A denotes CH$_2$, CD$_2$, C=NH, CHMe, CMe$_2$, 1,1'-cyclopropylene, 1,1'-cyclobutylidene;
B$^1$ denotes phenyl;
B$^2$ denotes phenyl;
X denotes O or NR$^5$, wherein R$^5$ denotes methyl, ethyl, cyclopropyl, cyclobutyl, CONHCH$_2$-phenyl, CH$_2$CF$_3$, or benzyl, optionally substituted with F;
n denotes 0 or 1;
R$^1$ denotes H;
R$^2$ denotes H;
R$^3$ denotes C$_{1-6}$-alkyl, which may optionally be substituted by one or more groups selected from among halogen, OH, CN, CONH$_2$, CONH—C$_{1-6}$-alkyl, CON(C$_{1-6}$-alkyl)$_2$, COOH, COO—C$_{1-6}$-alkyl, COH, CO—C$_{1-6}$-alkyl, phenyl, CO-phenyl, OH, O—C$_{1-6}$-alkyl, SO$_2$—C$_{1-6}$-alkanol; SO$_2$—C$_{1-6}$-alkyl, SO$_2$—C$_{1-6}$-haloalkyl, SO$_2$—NH$_2$, SO$_2$—NH—C$_{1-6}$-alkyl, SO$_2$—N(C$_{1-6}$-alkyl)$_2$, NO$_2$, NH$_2$, NH—C$_{1-6}$-alkyl, and N(C$_{1-6}$-alkyl)$_2$; or R$^3$ denotes a group selected from among C$_{3-8}$-cycloalkyl, a C$_{3-8}$-cycloalkyl bridged by C$_{1-3}$-alkylene and C$_{1-6}$-alkyl, which may optionally be substituted in each case by one or more groups selected from among phenyl or another aromatic or non-aromatic C$_{3-8}$ ring, preferably a C$_{5-7}$ ring, more preferably a C$_{5-6}$ ring, which may optionally contain in each case 1 to 4 heteroatoms independently of one another selected from N, O, S, while each of these groups may optionally be substituted by one or more groups selected from among C$_{1-6}$-alkyl, C$_{1-6}$-haloalkyl, CN, CONH$_2$, CONH—C$_{1-6}$-alkyl, CON(C$_{1-6}$-alkyl)$_2$, COOH, COO—C$_{1-6}$-alkyl, COH, CO—C$_{1-6}$-alkyl, phenyl, CO-phenyl, OH, O—C$_{1-6}$-alkyl, O—C$_{1-6}$-haloalkyl, halogen, SH, S—C$_{1-6}$-alkyl, S—C$_{1-6}$-haloalkyl, SO$_2$—C$_{1-6}$-alkanol, SO$_2$—C$_{1-6}$-alkyl, NH—C$_{1-6}$-alkyl, and N(C$_{1-6}$-alkyl)$_2$, an aromatic or non-aromatic C$_{3-8}$ ring, preferably a C$_{5-7}$ ring, more preferably a C$_{5-6}$ ring, which optionally contains 1 to 4 heteroatoms selected independently of one another from N, O, S, while this aromatic or non-aromatic C$_{3-8}$ ring may optionally be substituted by a group selected from oxo, hydroxyl, halogen, or C$_{1-6}$-alkyl, and C$_{1-6}$-haloalkyl; or R$^3$ denotes a group selected from among phenyl and another aromatic or non-aromatic C$_{3-8}$ ring, preferably a C$_{5-7}$ ring, more preferably a C$_{5-6}$ ring, which may optionally contain 1 to 4 heteroatoms selected from N, O, S, and which may optionally be substituted by one or more groups selected from among phenyl, C$_{1-6}$-alkyl, C$_{1-6}$-haloalkyl, CONH$_2$, CONH—C$_{1-6}$-alkyl, CON(C$_{1-6}$-alkyl)$_2$, COOH, COO—C$_{1-6}$-alkyl, COH, CO—C$_{1-6}$-alkyl, CO-phenyl, OH, O—C$_{1-6}$-alkyl, O—C$_{1-6}$-haloalkyl, halogen, SO$_2$—C$_{1-6}$-alkyl, SO$_2$—C$_{1-6}$-alkanol, SO$_2$—C$_{1-6}$-haloalkyl, SO$_2$—NH$_2$, SO$_2$—NH—C$_{1-6}$-alkyl, SO$_2$—N(C$_{1-6}$-alkyl)$_2$, NO$_2$, NH$_2$, NH—C$_{1-6}$ alkyl, N(C$_{1-6}$-alkyl)$_2$, and N—(SO$_2$—C$_{1-4}$-alkyl)(R$^{3.4}$), wherein R$^{3.4}$ denotes a C$_{5-10}$-heteroaryl-C$_{1-6}$-alkylene;

R$^3$ denotes a group selected from among C$_{1-6}$-alkyl, C$_{5-10}$-heteroaryl-C$_{1-6}$-alkylene, C$_{6-10}$-aryl-C$_{1-6}$-alkylene, C$_{3-7}$-cycloalkyl, phenyl, and an aromatic or non-aromatic C$_{3-8}$ ring, preferably a C$_{5-7}$ ring, more preferably a C$_{5-6}$ ring, which may contain 1 to 4 heteroatoms selected from N, O, and S, while each of these groups may optionally be substituted by one or more groups selected from among B, halogen, OH, C$_{1-6}$-alkyl, oxo, and B is a compound of formula 2

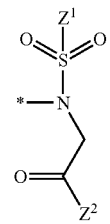

2 wherein Z$^1$ denotes H, OH, halogen, C$_{1-6}$-alkyl, C$_{1-6}$-alkanol, or O(C$_{1-6}$-alkyl), and Z$^2$ denotes OH, NH$_2$, NH(C$_{1-6}$-alkyl), N(C$_{1-6}$-alkyl)$_2$, O(C$_{1-6}$-alkyl), mono- or bicyclic C$_{3-7}$-cycloalkyl, mono- or bicyclic aromatic or non-aromatic C$_{3-10}$-heterocycle, or phenyl; and $R^4$ denotes H, F, or Cl,
optionally in the form of the racemates, enantiomers, diastereomers thereof, and optionally in the form of the pharmacologically acceptable acid addition salts, solvates, or hydrates thereof, as well as deuterated forms thereof.

Also particularly preferred are compounds of the above formula 1 or 1a, wherein:
A denotes $CH_2$, $CD_2$, C=NH, CHMe, $CMe_2$, 1,1'-cyclopropylene, 1,1'-cyclobutylidene;
$B^1$ denotes phenyl;
$B^2$ denotes phenyl;
X denotes O or $NR^5$, wherein $R^5$ denotes methyl, ethyl, cyclopropyl, cyclobutyl, $CONHCH_2$-phenyl, $CH_2CF_3$, or benzyl, optionally substituted by F;
n denotes 0 or 1;
$R^1$ denotes H;
$R^2$ denotes H;
wherein $R^3$ denotes a group selected from among

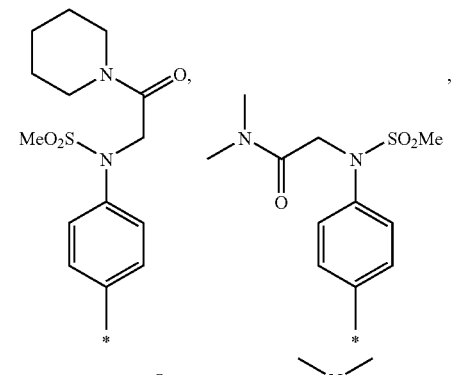

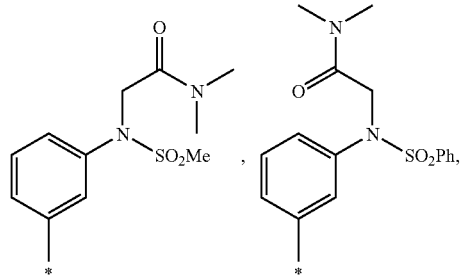

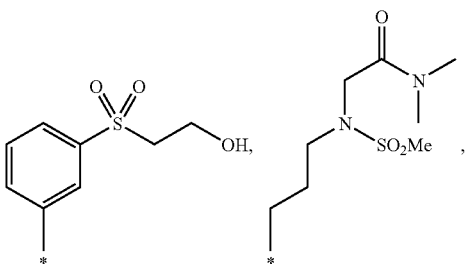

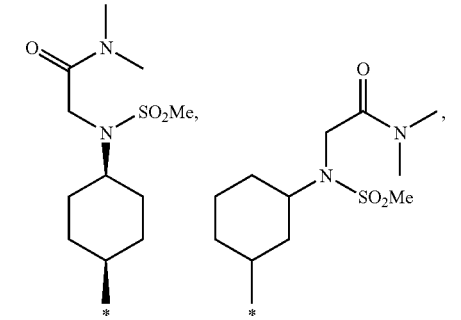

-continued

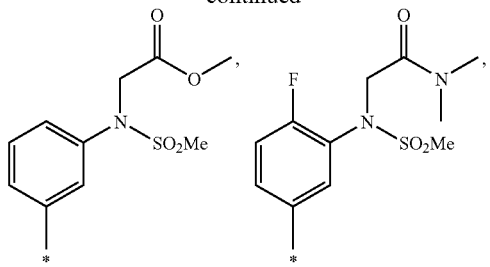

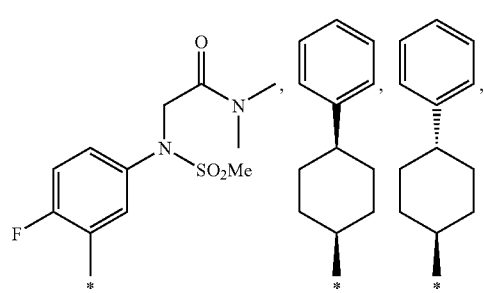

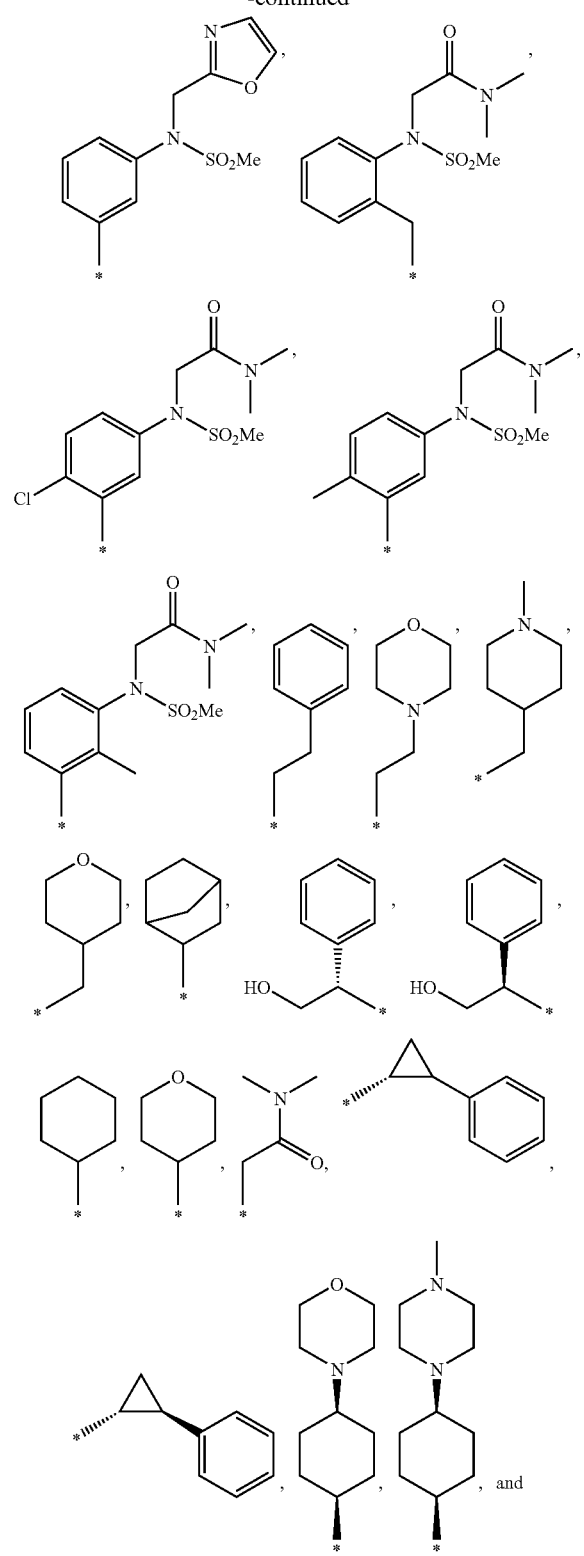

R[4] denotes H, F, or Cl,
optionally in the form of the racemates, enantiomers, diastereomers, and optionally in the form of the pharmacologically acceptable acid addition salts, solvates, or hydrates thereof, as well as deuterated forms thereof.

TERMS AND DEFINITIONS USED

Unless otherwise stated, all the substituents are independent of one another. If, for example, there are a plurality of $C_{1-6}$-alkyl groups as substituents in one group, in the case of three substituents $C_{1-6}$-alkyl, one may represent methyl, one n-propyl, and one tert-butyl.

Within the scope of this application, in the definition of possible substituents, these may also be represented in the form of a structural formula. An asterisk (*) in the structural formula of the substituent is to be understood as being the linking point to the rest of the molecule. Moreover, the atom of the substituent which follows the linking point is referred to as the atom in position number 1. Thus, for example, the groups N-piperidinyl (I), 4-piperidinyl (II), 2-tolyl (III), 3-tolyl (IV), and 4-tolyl (V) are shown as follows:

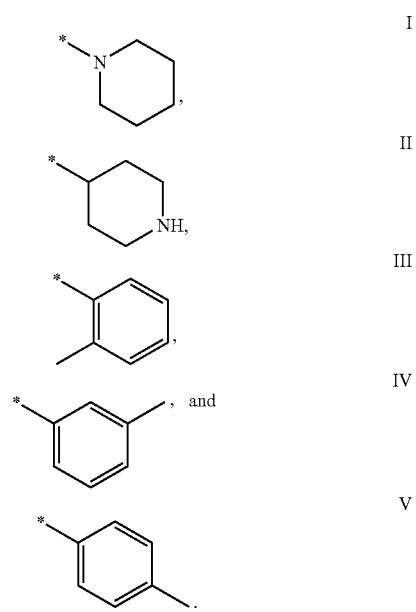

If there is no asterisk (*) in the structural formula of the substituent, each hydrogen atom may be removed from the substituent and the valency thus freed may act as a binding site to the rest of a molecule. Thus, for example, VI may represent 2-tolyl, 3-tolyl, 4-tolyl, and benzyl

By the term "$C_{1-6}$-alkyl" (including those which are part of other groups) are meant branched and unbranched alkyl groups with 1 to 6 carbon atoms and by the term "$C_{1-4}$-alkyl" are meant branched and unbranched alkyl groups with 1 to 4 carbon atoms. Alkyl groups with 1 to 4 carbon atoms are preferred. Examples include: methyl, ethyl, n-propyl, isopropyl, n-butyl, isobutyl, sec-butyl, tert-butyl, n-pentyl, isopentyl, neopentyl, or hexyl. The following abbreviations may optionally also be used for the abovementioned groups: Me, Et, n-Pr, i-Pr, n-Bu, i-Bu, t-Bu, etc. Unless stated otherwise, the definitions propyl, butyl, pentyl, and hexyl include all the possible isomeric forms of the groups in question. Thus, for example, propyl includes n-propyl and isopropyl, butyl includes isobutyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Preferred are alkylene groups with 1 to 4 carbon atoms. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, or hexylene. Unless stated otherwise, the definitions propylene, butylene, pentylene, and hexylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

If the carbon chain is substituted by a group which together with one or two carbon atoms of the alkylene chain forms a carbocyclic ring with 3, 5, or 6 carbon atoms, the following examples of rings are also included:

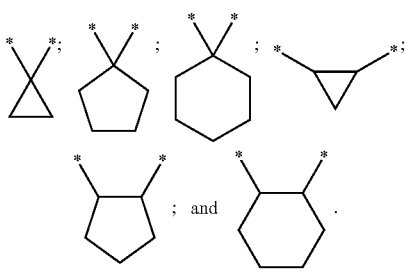

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl, and hexenyl include all the possible isomeric forms of the groups in question. Thus, for example, propenyl includes 1-propenyl and 2-propenyl, butenyl includes 1-, 2-, and 3-butenyl, 1-methyl-1-propenyl, 1-methyl-2-propenyl, etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Preferred are alkenylene groups with 2 to 4 carbon atoms. Examples include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, or hexenylene. Unless stated otherwise, the definitions propenylene, butenylene, pentenylene, and hexenylene include all the possible isomeric forms of the groups in question with the same number of carbons. Thus, for example, propenyl also includes 1-methylethenylene and butenylene includes 1-methylpropenylene, 1,1-dimethylethenylene, and 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl, and hexynyl include all the possible isomeric forms of the groups in question. Thus, for example, propynyl includes 1-propynyl and 2-s propynyl, butynyl includes 1-, 2-, and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Preferred are alkynylene groups with 2 to 4 carbon atoms. Examples include: ethynylene, propynylene, 1-methylethynylene, butynylene, 1-methylpropynylene, 1,1-dimethylethynylene, 1,2-dimethylethynylene, pentynylene, 1,1-dimethylprop ynylene, 2,2-dimethylpropynylene, 1,2-dimethylpropynylene, 1,3-dimethylpropynylene, or hexynylene. Unless stated otherwise, the definitions propynylene, butynylene, pentynylene, and hexynylene include all the possible isomeric forms of the groups in question with the same number of carbons. Thus, for example, propynyl also includes 1-methylethynylene and butynylene includes 1-methylpropynylene, 1,1-dimethylethynylene, 1,2-dimethylethynylene.

By the term "aryl" (including those which are part of other groups) are meant aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, isopropyl, tert-butyl, hydroxy, fluorine, chlorine, bromine, and iodine.

By the term "aryl-$C_{1-6}$-alkylene" (including those which are part of other groups) are meant branched and unbranched alkylene groups with 1 to 6 carbon atoms, which are substituted by an aromatic ring system with 6 or 10 carbon atoms. Examples include: benzyl, 1- or 2-phenylethyl, or 1- or 2-naphthylethyl. Unless otherwise stated, the aromatic groups may be substituted by one or more groups selected from among methyl, ethyl, isopropyl, tert-butyl, hydroxy, fluorine, chlorine, bromine, and iodine.

By the term "heteroaryl-$C_{1-6}$-alkylene" (including those which are part of other groups) are meant, even though they are already included under "aryl-$C_{1-6}$-alkylene", branched and unbranched alkylene groups with 1 to 6 carbon atoms, which are substituted by a heteroaryl.

A heteroaryl of this kind includes five- or six-membered heterocyclic aromatic groups or 5-10-membered, bicyclic heteroaryl rings which may contain one, two, or three heteroatoms selected from among oxygen, sulfur, and nitrogen, and contain so many conjugated double bonds that an aromatic system is formed. The following are examples of five- or six-membered heterocyclic aromatic groups:

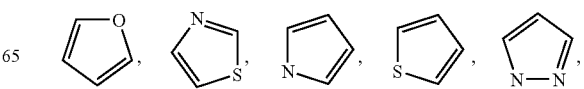

-continued

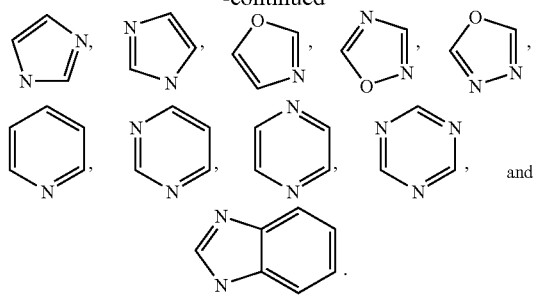

Unless otherwise stated, these heteroaryls may be substituted by one or more groups selected from among methyl, ethyl, isopropyl, tert-butyl, hydroxy, fluorine, chlorine, bromine, and iodine. The following are examples of heteroaryl-$C_{1-6}$-alkylenes:

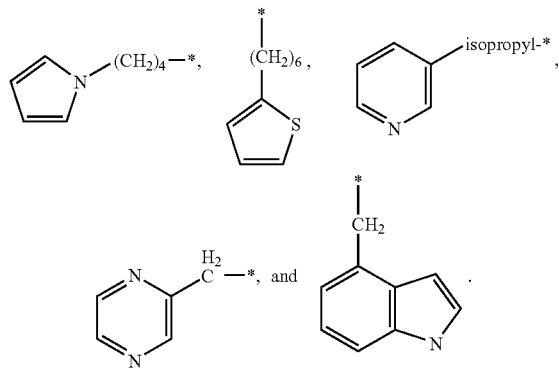

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, and $CH_2CF_3$.

By the term "$C_{3-7}$-cycloalkyl" (including those which are part of other groups) are meant cyclic alkyl groups with 3 to 7 carbon atoms. Examples include: cyclopropyl, cyclobutyl, cyclopentyl, cyclohexyl, or cycloheptyl. Unless otherwise stated, the cyclic alkyl groups may be substituted by one or more groups selected from among methyl, ethyl, isopropyl, tert-butyl, hydroxy, fluorine, chlorine, bromine, and iodine.

By the term "heterocyclic rings" or also "heterocycles" are meant five-, six-, or seven-membered, saturated or unsaturated heterocyclic rings which may contain one, two, or three heteroatoms, selected from among oxygen, sulfur, and nitrogen, while the ring may be linked to the molecule through a carbon atom or through a nitrogen atom, if there is one. Although included by the term "heterocyclic rings" or "heterocycles", the term "heterocyclic non-aromatic rings" refers to five-, six-, or seven-membered unsaturated rings. Examples include:

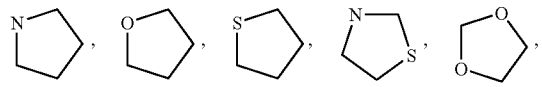

-continued

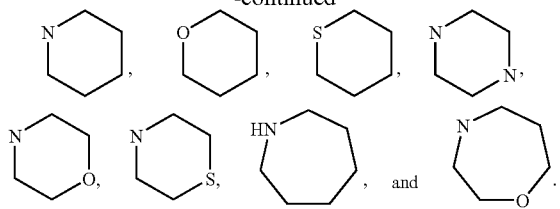

Although included by the term "heterocyclic rings" or "heterocycles", the term "heterocyclic aromatic rings" or "heteroaryl" refers to five- or six-membered heterocyclic aromatic groups or 5-10-membered, bicyclic heteroaryl rings which may contain one, two, or three heteroatoms, selected from among oxygen, sulfur, and nitrogen, and contain so many conjugated double bonds that an aromatic system is formed. Examples of five- or six-membered heterocyclic aromatic groups include:

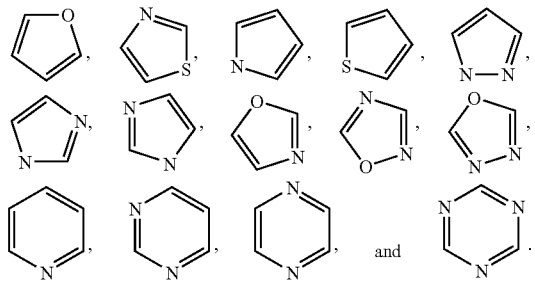

Unless otherwise mentioned, a heterocyclic ring (or "heterocycle") may be provided with a keto group. Examples include:

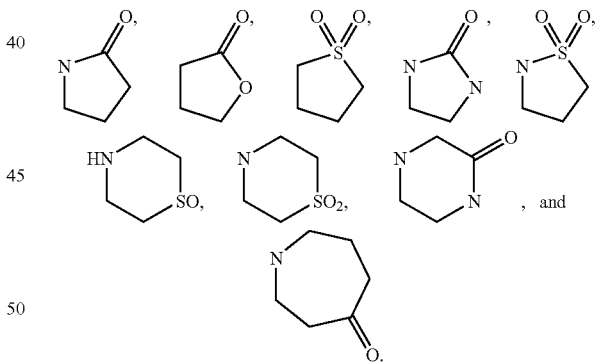

By the term "bicyclic rings" are meant eight-, nine-, or ten-membered bicyclic rings which may optionally contain one or more heteroatoms, selected from among oxygen, sulfur, and nitrogen. The ring may be linked to the molecule through a carbon atom of the ring or through a nitrogen atom of the ring, if there is one. Examples include:

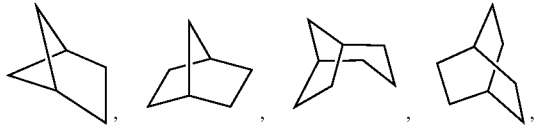

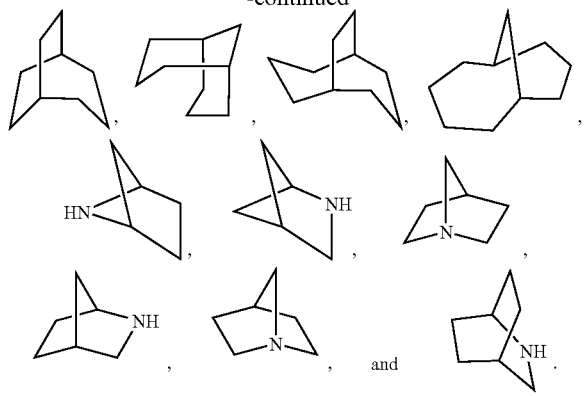

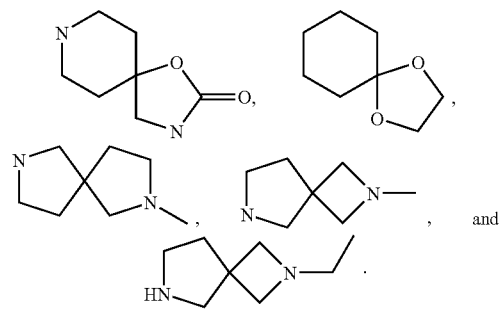

Although included by the term "bicyclic rings", the term "fused bicyclic rings" denotes bicyclic rings wherein the bridge separating the rings denotes a direct single bond. The following are examples of a fused, bicyclic ring:

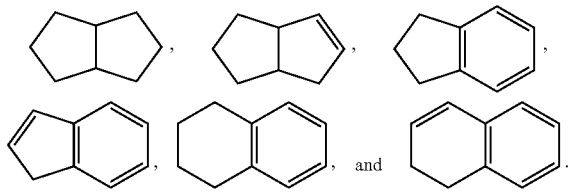

Although included by the term "bicyclic rings", the term "fused bicyclic heterorings" denotes bicyclic 5-10 membered heterorings which contain one, two, or three heteroatoms, selected from among oxygen, sulfur, and nitrogen, and wherein the bridge separating the rings denotes a direct single bond. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

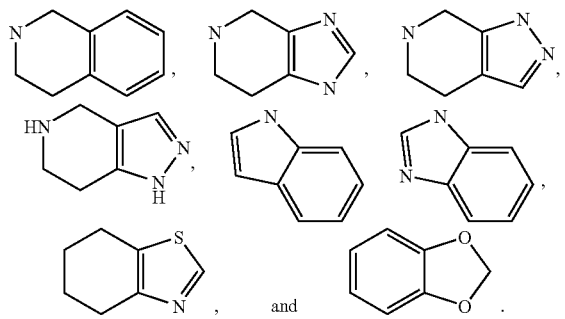

By the term "heterocyclic spirorings" (spiro) are meant 5-10 membered, spirocyclic rings which may optionally contain one, two, or three heteroatoms, selected from among oxygen, sulfur, and nitrogen, while the ring may be linked to the molecule through a carbon atom or through a nitrogen atom, if there is one. Unless otherwise mentioned, a spirocyclic ring may be provided with an oxo, methyl, or ethyl group. Examples include:

"Halogen" within the scope of the present invention denotes fluorine, chlorine, bromine, or iodine. Unless stated to the contrary, fluorine, chlorine, and bromine are regarded as preferred halogens.

By the terms "ambient temperature" or "RT" is meant normal room temperature.

Compounds of general formula 1 may have acid groups, mainly carboxyl groups, and/or basic groups such as, e.g., amino functions. Compounds of general formula 1 may therefore be present as internal salts, as salts with pharmaceutically useable inorganic acids such as, for example, hydrochloric acid, sulfuric acid, phosphoric acid, sulfonic acid, or organic acids (such as, for example, maleic acid, fumaric acid, citric acid, tartaric acid, or acetic acid) or as salts with pharmaceutically useable bases such as alkali or alkaline earth metal hydroxides or carbonates, zinc, or ammonium hydroxides or organic amines such as e.g., diethylamine, triethylamine, or triethanolamine, inter alia.

As mentioned hereinbefore, the compounds of formula 1 may be converted into the salts thereof, particularly for pharmaceutical use, into the physiologically and pharmacologically acceptable salts thereof. These salts may on the one hand be in the form of the physiologically and pharmacologically acceptable acid addition salts of the compounds of formula 1 with inorganic or organic acids. On the other hand, if R is hydrogen, the compound of formula 1 may also be converted by reaction with inorganic bases into physiologically and pharmacologically acceptable salts with alkali or alkaline earth metal cations as counter ion. The acid addition salts may be prepared, for example, using hydrochloric acid, hydrobromic acid, sulfuric acid, phosphoric acid, methanesulfonic acid, acetic acid, fumaric acid, succinic acid, lactic acid, citric acid, tartaric acid, or maleic acid. It is also possible to use mixtures of the abovementioned acids. The alkali and alkaline earth metal salts of the compound of formula I are preferably prepared using the alkali and alkaline earth metal hydroxides and hydrides thereof, of which the hydroxides and hydrides of the alkaline earth metals, particularly of sodium and potassium, are preferred and sodium and potassium hydroxide are particularly preferred.

If desired, the compounds of general formula (1) may be converted into the salts thereof, particularly, for pharmaceutical use, into the pharmaceutically acceptable acid addition salts with an inorganic or organic acid. Suitable acids include, for example, succinic acid, hydrobromic acid, acetic acid, fumaric acid, maleic acid, methanesulfonic acid, lactic acid, phosphoric acid, hydrochloric acid, sulfuric acid, tartaric acid, or citric acid. It is also possible to use mixtures of the abovementioned acids.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids such as, for example, acid addition salts with hydrohalic acids, for example, hydrochloric or hydrobromic acid or organic acids such as, for example, oxalic, fumaric, diglycolic, or methanesulfonic acid.

The compounds according to the invention may optionally occur as racemates, but they may also be obtained as pure enantiomers, i.e., in the (R) or (S) form. Preferred compounds are those which occur as racemates or as the (S) form.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids such as, for example, acid addition salts with hydrohalic acids, for example, hydrochloric or hydrobromic acid or organic acids, such as, for example, oxalic, fumaric, diglycolic, or methanesulfonic acid.

The Tables of Examples A and B that follow list compounds of formula 1 prepared according to the invention.

EXAMPLES A

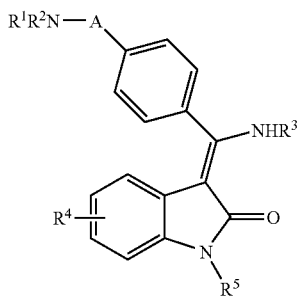

| # | $R^1$ | $R^2$ | $R^3$ | $R^4$ | $R^5$ | A |
|---|---|---|---|---|---|---|
| 1. | H | H | (N-imidazolyl-methyl-phenyl) | H | Me | $CH_2$ |
| 2. | H | H | (4-imidazolyl-phenyl) | H | (butyl-NH-C(O)-) | $CH_2$ |
| 3. | H | H | (4-imidazolyl-phenyl) | H | (benzyl-NH-C(O)-) | $CH_2$ |

-continued
EXAMPLES A
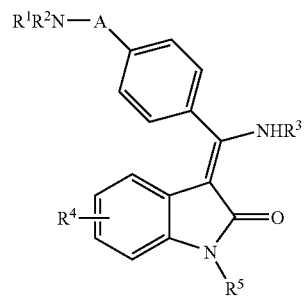
| # | R¹ | R² | R³ | R⁴ | R⁵ | A |
|---|----|----|----|----|----|---|
| 4. | H | H | 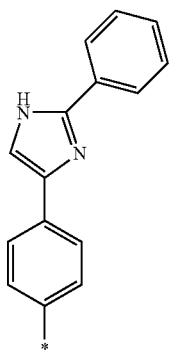 | H | Me | $CH_2$ |
| 5. | H | H | 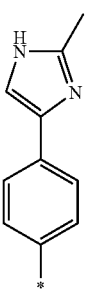 | H | Me | $CH_2$ |
| 6. | H | H | 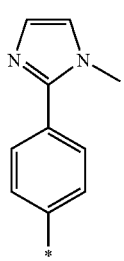 | H | Me | $CH_2$ |
| 7. | H | H | 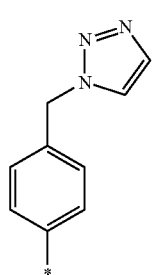 | H | Me | $CH_2$ |

EXAMPLES A
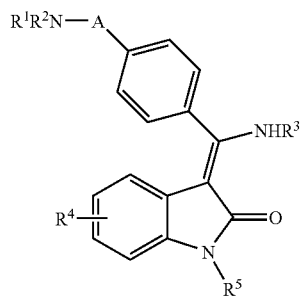
| #   | R¹ | R² | R³ | R⁴ | R⁵ | A   |
|-----|----|----|-----|----|-----|-----|
| 8.  | H  | H  | (1-benzyl-2-oxopyrrolidin-1-yl phenyl) | H | Me | $CH_2$ |
| 9.  | H  | H  | (4-((2H-1,2,3-triazol-2-yl)methyl)phenyl) | H | Me | $CH_2$ |
| 10. | H  | H  | (4-(1H-imidazol-4-yl)phenyl) | H | benzyl | $CH_2$ |
| 11. | H  | H  | (4-(1H-imidazol-4-yl)phenyl) | H | ethyl | $CH_2$ |

-continued
EXAMPLES A
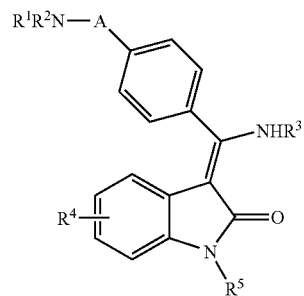
| # | R¹ | R² | R³ | R⁴ | R⁵ | A |
|---|----|----|----|----|----|---|
| 12. | H | H | (4-(1H-imidazol-4-yl)phenyl) | H | acetyl | CH₂ |
| 13. | H | H | (4-(1-methyl-1H-imidazol-4-yl)phenyl) | H | phenyl | CH₂ |
| 14. | H | H | (4-(1-methyl-1H-imidazol-4-yl)phenyl) | H | phenyl | C=NH |
| 15. | H | H | (4-(1-methyl-1H-imidazol-4-yl)phenyl) | H | 4-fluorobenzyl | CH₂ |

-continued
EXAMPLES A
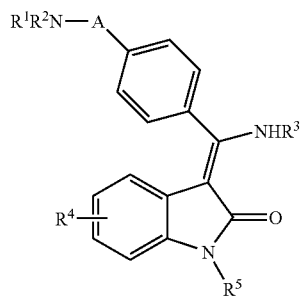
| # | R[1] | R[2] | R[3] | R[4] | R[5] | A |
|---|---|---|---|---|---|---|
| 16. | H | H | 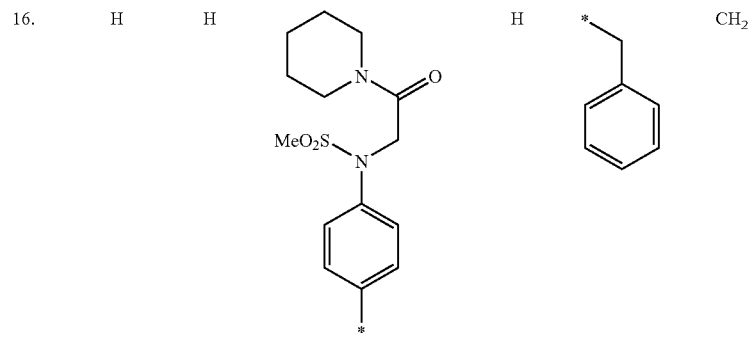 | H | * <br> (benzyl) | $CH_2$ |
| 17. | H | H | 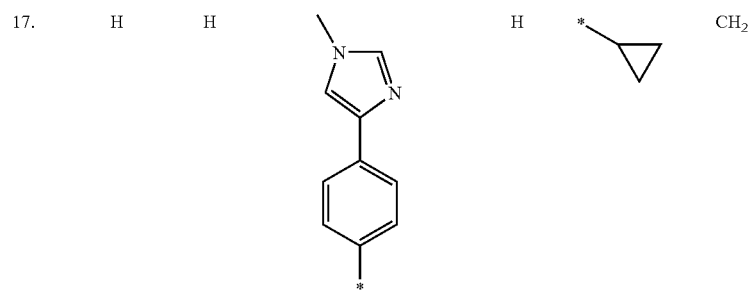 | H | * <br> (cyclopropyl) | $CH_2$ |
| 18. | H | H | 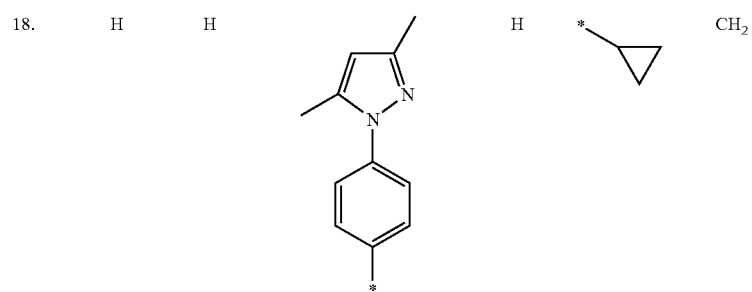 | H | * <br> (cyclopropyl) | $CH_2$ |
| 19. | H | H | 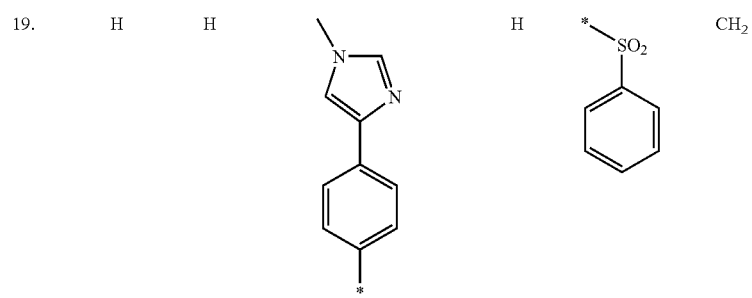 | H | *—$SO_2$—Ph | $CH_2$ |

-continued
EXAMPLES A
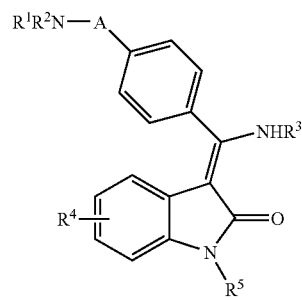
| # | R¹ | R² | R³ | R⁴ | R⁵ | A |
|---|----|----|----|----|----|---|
| 20. | H | H | N,N-dimethyl-2-[N-(4-*)phenyl-N-(methylsulfonyl)amino]acetamide | H | *-benzyl | CH₂ |
| 21. | H | H | 4-(1-methyl-1H-imidazol-4-yl)phenyl-* | H | *-benzyl | CH₂ |
| 22. | Et | Et | 4-(1-methyl-1H-imidazol-4-yl)phenyl-* | H | *-benzyl | CH₂ |
| 23. | H | H | N,N-dimethyl-2-[N-(3-*)phenyl-N-(methylsulfonyl)amino]acetamide | H | *-benzyl | CH₂ |

-continued
EXAMPLES A
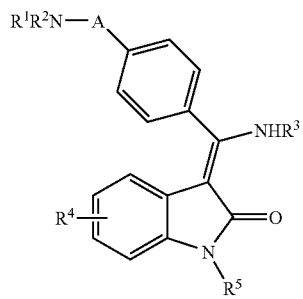
| # | R¹ | R² | R³ | R⁴ | R⁵ | A |
|---|----|----|----|----|----|----|
| 24. | H | H | N,N-dimethylacetamide-N-(3-phenylsulfonamide) | H | benzyl* | $CH_2$ |
| 25. | H | H | 4-(1-methyl-1H-imidazol-4-yl)phenyl* | H | benzyl* | $C=NH$ |
| 26. | H | H | 4-(1-methyl-1H-imidazol-2-yl)phenyl* | H | 4-fluorobenzyl* | $CH_2$ |
| 27. | H | H | 4-(2-(1H-indol-2-yl)-1H-imidazol-4-yl)phenyl* | H | 4-fluorobenzyl* | $CH_2$ |

-continued
EXAMPLES A
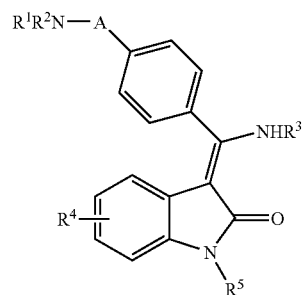
| # | R¹ | R² | R³ | R⁴ | R⁵ | A |
|---|----|----|----|----|----|----|
| 28. | H | H | 4-(1H-pyrazol-1-yl)phenyl | H | 4-fluorobenzyl | CH₂ |
| 29. | H | H | 4-(1H-1,2,4-triazol-1-yl)phenyl | H | 4-fluorobenzyl | CH₂ |
| 30. | H | H | 4-(5-methyl-1H-imidazol-4-yl)phenyl | H | 4-fluorobenzyl | CH₂ |
| 31. | H | H | 3-(2-methylpyrimidin-4-yl)phenyl | H | 4-fluorobenzyl | CH₂ |

-continued
EXAMPLES A
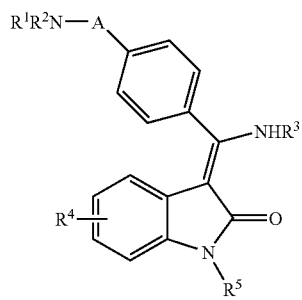
| # | R¹ | R² | R³ | R⁴ | R⁵ | A |
|---|---|---|---|---|---|---|
| 32. | H | H | H | H | *-CH₂-(4-F-C₆H₄) | CH₂ |
| 33. | H | H | H | H | Me | CH₂ |
| 34. | *-C(O)-O-ᵗBu | H | *-(4-(1H-imidazol-4-yl)phenyl) | H | Me | CH₂ |
| 35. | H | H | *-(4-(1H-imidazol-4-yl)phenyl) | H | Me | CH₂ |
| 36. | H | H | *-(4-(1-methyl-1H-imidazol-4-yl)phenyl) | H | Me | CH₂ |

-continued
EXAMPLES A
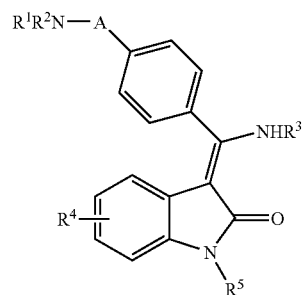
| # | R¹ | R² | R³ | R⁴ | R⁵ | A |
|---|----|----|----|----|----|----|
| 37. | H | H | 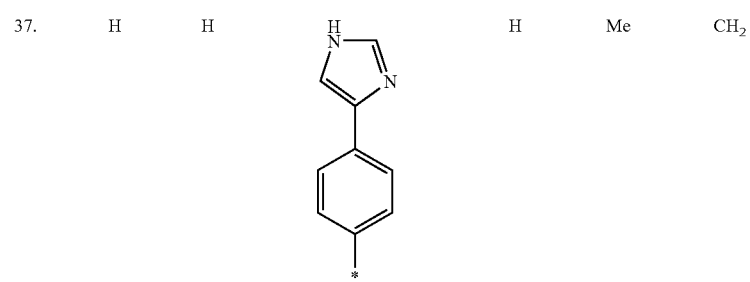 | H | Me | CH₂ |
| 37a. | H | H | 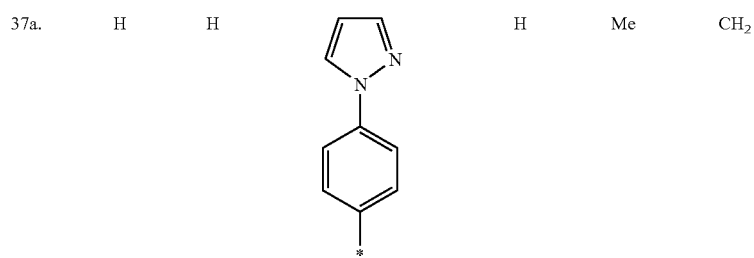 | H | Me | CH₂ |
| 37b. | H | H | 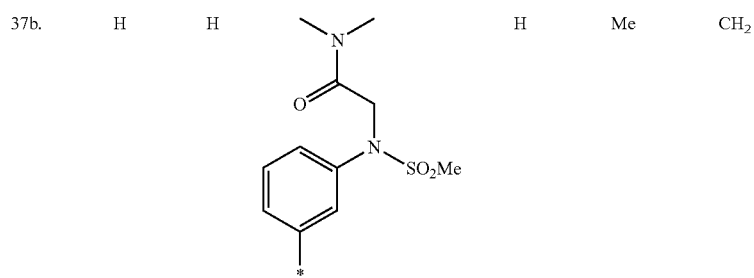 | H | Me | CH₂ |
| 37c. | H | H | 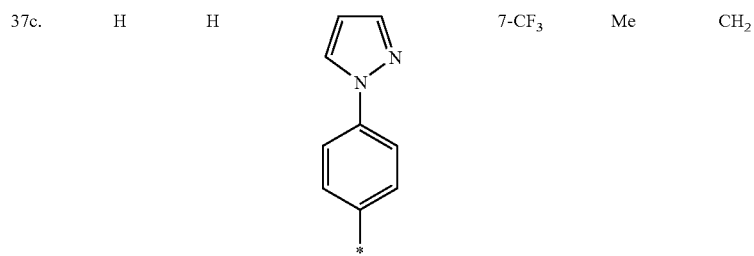 | 7-CF₃ | Me | CH₂ |

EXAMPLES A
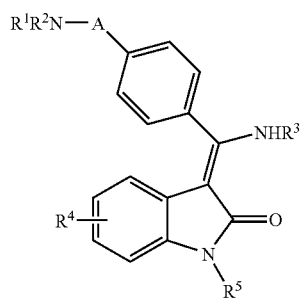
| # | R¹ | R² | R³ | R⁴ | R⁵ | A |
|---|----|----|----|----|----|----|
| 37d. | H | H | (1-phenyl-pyrazol-4-yl)phenyl | H | cBu | $CH_2$ |
| 37e. | H | H | (1-methyl-imidazol-4-yl)phenyl | H | cBu | $CH_2$ |
| 37f. | H | H | 3-[N-(methylsulfonyl)-N-(N,N-dimethylcarbamoylmethyl)amino]phenyl | H | cBu | $CH_2$ |
| 37g. | H | H | 3-[N-(methylsulfonyl)-N-(N,N-dimethylcarbamoylmethyl)amino]phenyl | H | $CH_2CF_3$ | $CH_2$ |

-continued
EXAMPLES A
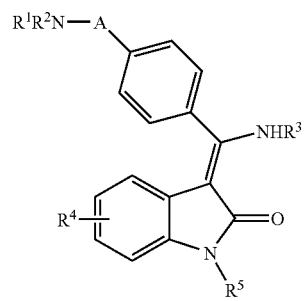
| # | $R^1$ | $R^2$ | $R^3$ | $R^4$ | $R^5$ | A |
|---|---|---|---|---|---|---|
| 37h. | H | H | 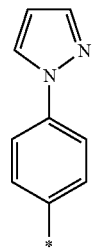 | H | $CH_2CF_3$ | $CH_2$ |
| 37i. | H | H | 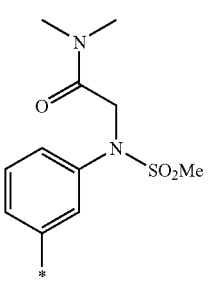 | H | $CONHCH_2Ph$ | $CH_2$ |
| 37j. | H | H | 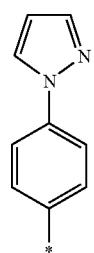 | H | $CONHCH_2Ph$ | $CH_2$ |
| 37k. | H | H | 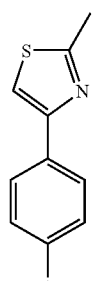 | H | $CH_2CF_3$ | $CH_2$ |

-continued
EXAMPLES A
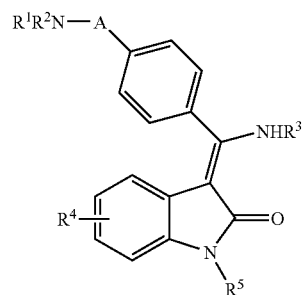
| # | R¹ | R² | R³ | R⁴ | R⁵ | A |
|---|---|---|---|---|---|---|
| 37l. | H | H | (trans-4-phenylcyclohexyl) | H | $CH_2CF_3$ | $CH_2$ |
| 37m. | H | H | (trans-4-(2-methylthiazol-4-yl)phenyl-cyclohexyl) | H | cBu | $CH_2$ |
| 37n. | H | H | (trans-4-(pyrazol-1-yl)cyclohexyl) | H | $CH_2CF_3$ | $CH_2$ |
| 37o. | H | H | (trans-4-(pyrazol-1-yl)cyclohexyl) | H | cBu | $CH_2$ |

EXAMPLES B
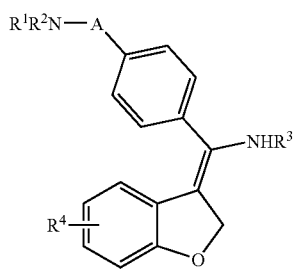
| # | R¹ | R² | R³ | R⁴ | A |
|---|---|---|---|---|---|
| 38. | H | H | 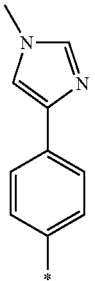 | H | C=NH |
| 39. | H | H | 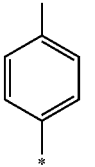 | H | $CH_2$ |
| 40. | H | H | 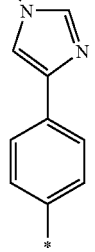 | H | 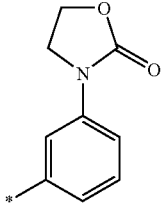 |
| 41. | H | H | 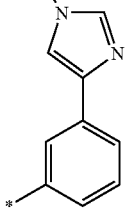 | H | $CH_2$ |
| 42. | H | H | 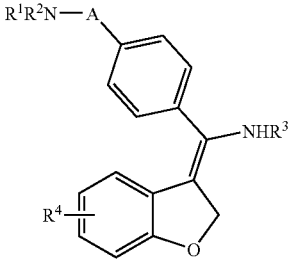 | H | $CH_2$ |
-continued
EXAMPLES B
| # | R¹ | R² | R³ | R⁴ | A |
|---|---|---|---|---|---|
| 43. | H | H | H | H | $CH_2$ |
| 44. | H | H | 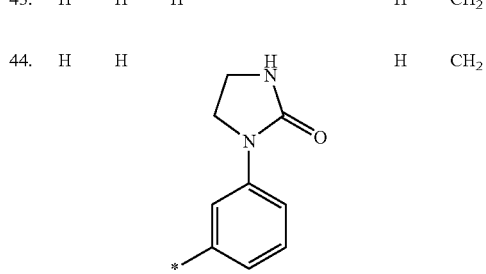 | H | $CH_2$ |
| 45. | H | H | 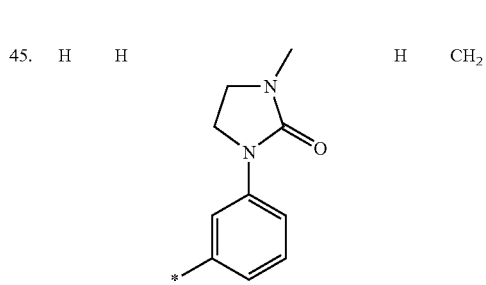 | H | $CH_2$ |
| 46. | H | H | 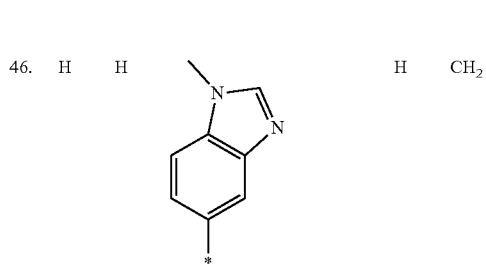 | H | $CH_2$ |
| 47. | H | H | 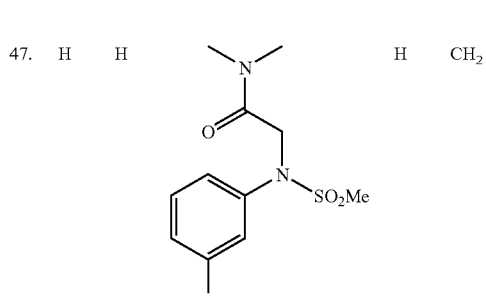 | H | $CH_2$ |

TABLE-continued
EXAMPLES B
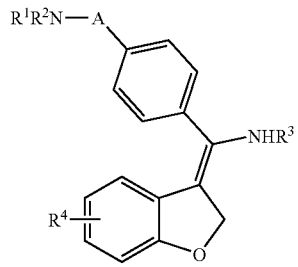
| # | R¹ | R² | R³ | R⁴ | A |
|---|----|----|----|----|----|
| 48. | H | H | 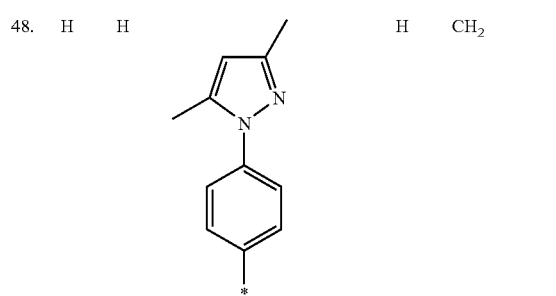 | H | CH₂ |
| 49. | H | H | 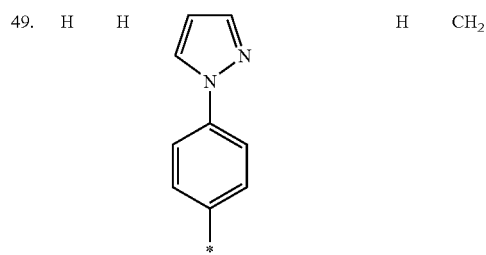 | H | CH₂ |
| 50. | H | H | 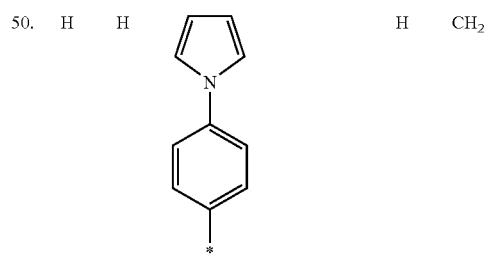 | H | CH₂ |
| 51. | H | H | 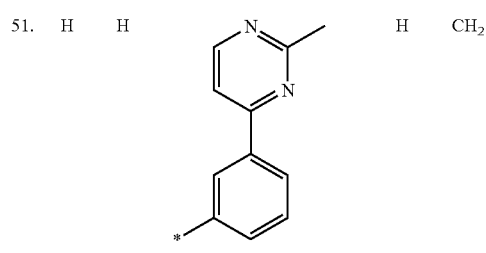 | H | CH₂ |
TABLE-continued
EXAMPLES B
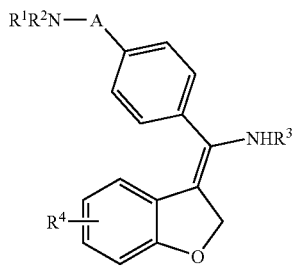
| # | R¹ | R² | R³ | R⁴ | A |
|---|----|----|----|----|----|
| 52. | H | H | 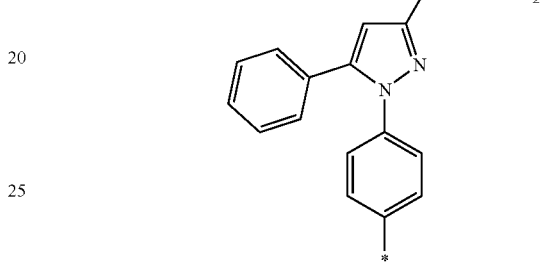 | H | CH₂ |
| 53. | H | H | 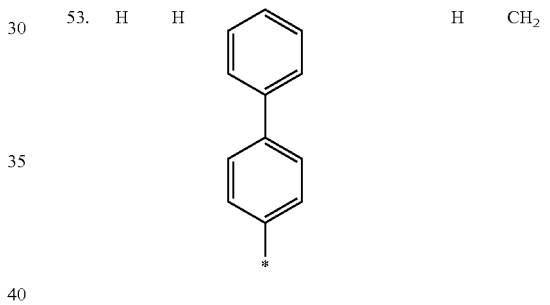 | H | CH₂ |
| 54. | H | H | 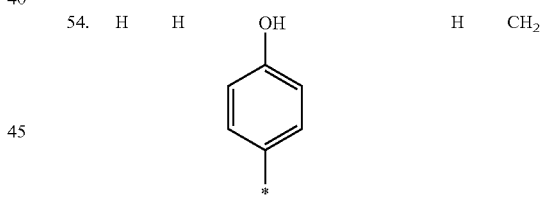 | H | CH₂ |
| 55. | H | H | 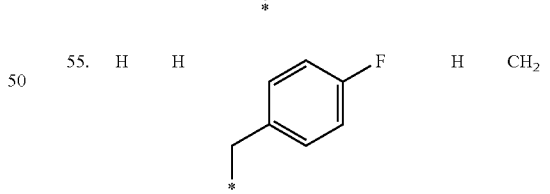 | H | CH₂ |
| 56. | H | H | 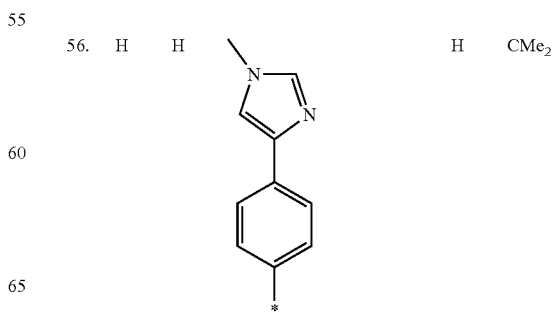 | H | CMe₂ |

-continued

EXAMPLES B

Structure: R¹R²N—A—(4-phenyl)—C(NHR³)=(3-position of 2,3-dihydrobenzofuran with R⁴)

| # | R¹ | R² | R³ | R⁴ | A |
|---|----|----|----|----|----|
| 57. | H | H | 1-(4-*-phenyl)-3-(trifluoromethyl)-1H-pyrazol-1-yl | H | CH₂ |
| 58. | H | H | 3-(3-*-phenyl)-4-methyl-4H-1,2,4-triazol-5-yl | H | CH₂ |
| 59. | H | H | 1-(4-*-phenyl)-3,5-bis(trifluoromethyl)-1H-pyrazol-1-yl | H | CH₂ |
| 60. | H | H | 1-(4-*-phenyl)-1H-pyrazol-1-yl | H | *-cyclopropyl-1,1-diyl |
| 61. | H | H | H | H | *-cyclopropyl-1,1-diyl |
| 62. | H | H | cyclopropyl | H | CH₂ |

-continued

EXAMPLES B

| # | R¹ | R² | R³ | R⁴ | A |
|---|----|----|----|----|----|
| 63. | H | H | cyclobutyl | H | CH₂ |
| 64. | H | H | 3-(*-phenyl)-N-(methylsulfonyl)-N-(2-(dimethylamino)-2-oxoethyl) | H | *-cyclopropyl-1,1-diyl |
| 65. | H | H | OH | H | *-cyclopropyl-1,1-diyl |
| 66. | H | H | 3-(4-*-phenyl)-4-methyl-4H-1,2,4-triazol-5-yl | H | CH₃ |
| 67. | H | H | 4-*-phenol (OH) | H | *-cyclopropyl-1,1-diyl |

-continued

EXAMPLES B

R¹R²N—A—[4-phenyl]—C(=benzofuran-3(2H)-ylidene)—NHR³ with R⁴ on benzofuran

| # | R¹ | R² | R³ | R⁴ | A |
|---|----|----|----|----|---|
| 68. | H | H | 2-methylthiazol-4-yl-phenyl (4-*) | H | CH₂ |
| 69. | H | H | 1-methylimidazol-4-yl-phenyl (4-*) | H | CH₂ |
| 70. | H | H | CH₂CF₃ | H | CH₂ |
| 71. | H | H | 3-(SO₂Me)phenyl (*) | H | CH₂ |
| 72. | H | H | 3-(N(Me)SO₂Me)phenyl (*) | H | CH₂ |

EXAMPLES C

R¹R²N—A—[4-phenyl]—C(=benzofuran-2(3H)-on-3-ylidene)—NHR³ with R⁴ on benzofuran

| # | R¹ | R² | R³ | R⁴ | A |
|---|----|----|----|----|---|
| 73. | H | H | 4-(furan-2-yl)phenyl (*) | H | CH₂ |
| 74. | H | H | 3-[N(SO₂Me)CH₂C(=O)N(Me)₂]phenyl (*) | H | CMe₂ |
| 75. | H | H | 4-(pyrazol-1-yl)phenyl (*) | H | CMe₂ |
| 76. | H | H | 3-[S(=O)₂CH₂CH₂OH]phenyl (*) | H | CH₂ |
| 77. | H | H | 4-(2-methylthiazol-4-yl)phenyl (*) | H | CMe₂ |

-continued
EXAMPLES C
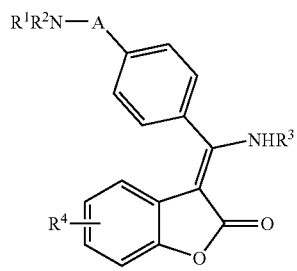
| # | R¹ | R² | R³ | R⁴ | A |
|---|----|----|----|----|----|
| 78. | H | H | 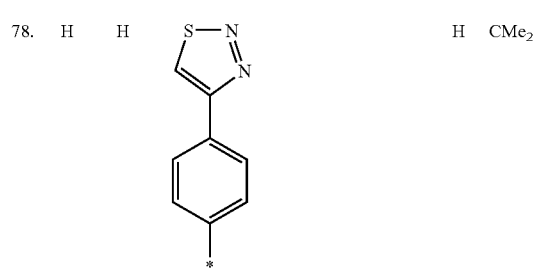 | H | CMe₂ |
| 79. | H | H | 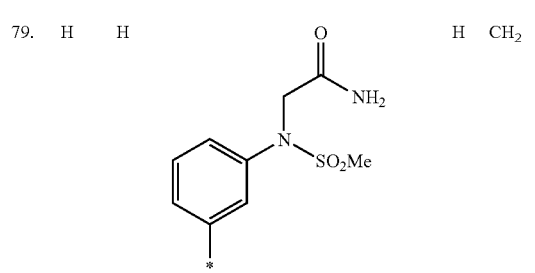 | H | CH₂ |
| 80. | H | H | 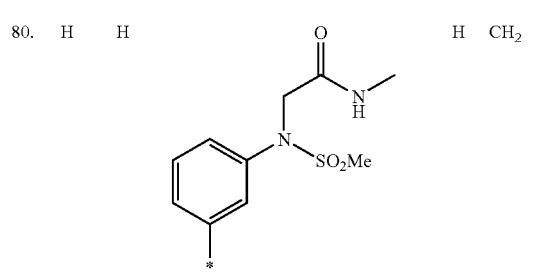 | H | CH₂ |
| 81. | H | H | 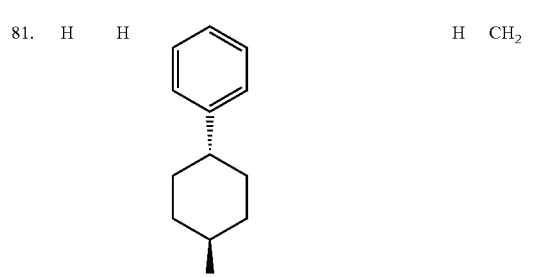 | H | CH₂ |
-continued
EXAMPLES C
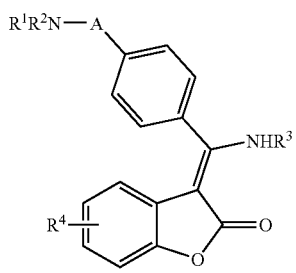
| # | R¹ | R² | R³ | R⁴ | A |
|---|----|----|----|----|----|
| 82. | H | H | 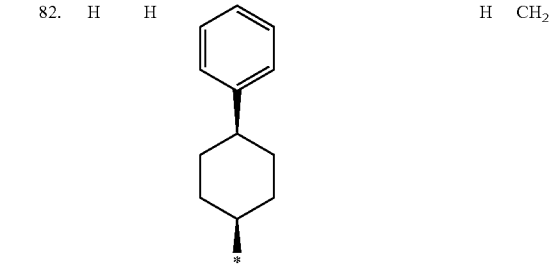 | H | CH₂ |
| 83. | H | H | 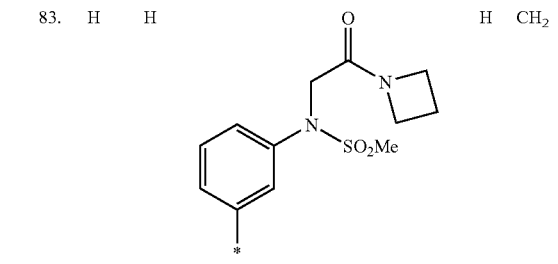 | H | CH₂ |
| 84. | H | H | 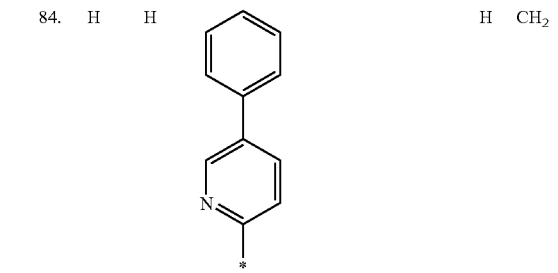 | H | CH₂ |
| 85. | H | H | 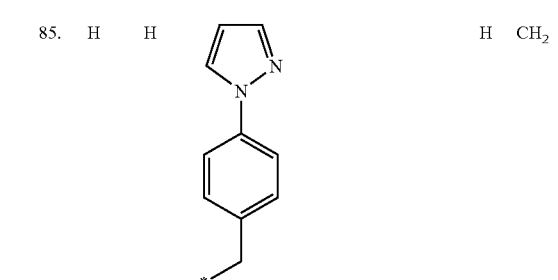 | H | CH₂ |

TABLE-continued
EXAMPLES C
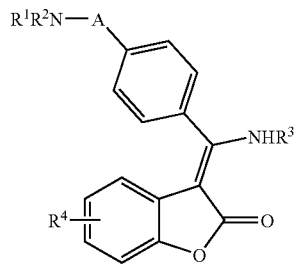
| # | R¹ | R² | R³ | R⁴ | A |
|---|----|----|----|----|----|
| 86. | H | H | 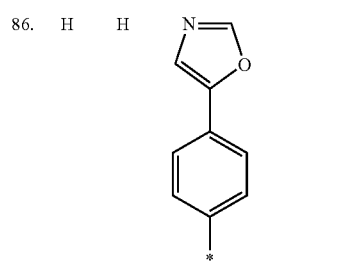 | H | CH₂ |
| 87. | H | H | 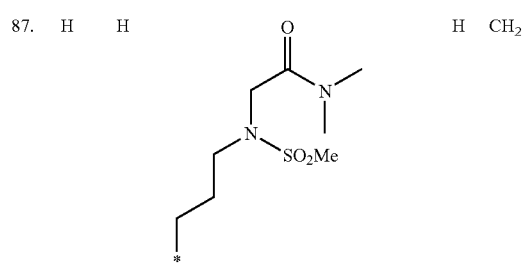 | H | CH₂ |
| 88. | H | H | 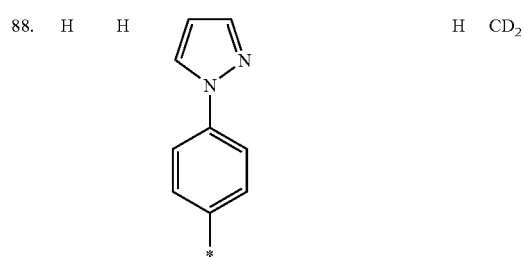 | H | CD₂ |
| 89. | H | H | 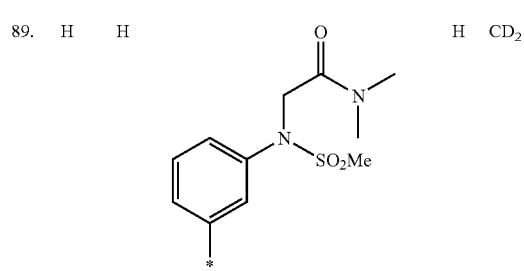 | H | CD₂ |
EXAMPLES C
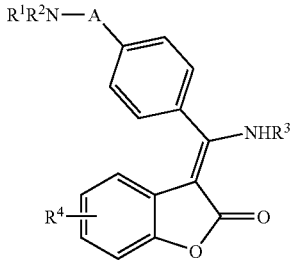
| # | R¹ | R² | R³ | R⁴ | A |
|---|----|----|----|----|----|
| 90. | H | H | 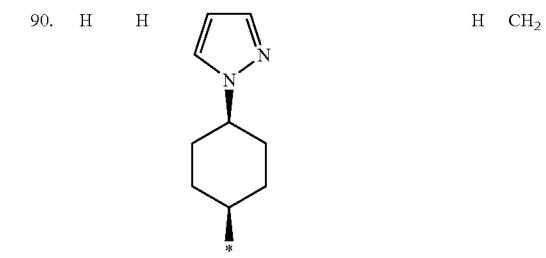 | H | CH₂ |
| 91. | H | H | 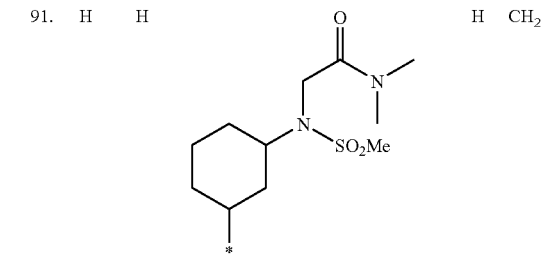 | H | CH₂ |
| 92. | H | H | 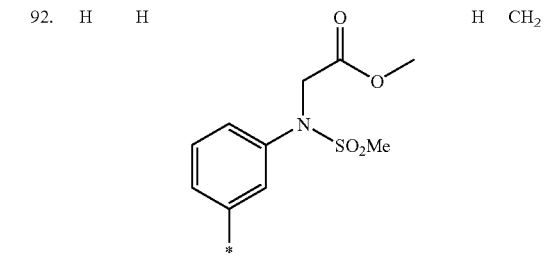 | H | CH₂ |
| 93. | H | H | 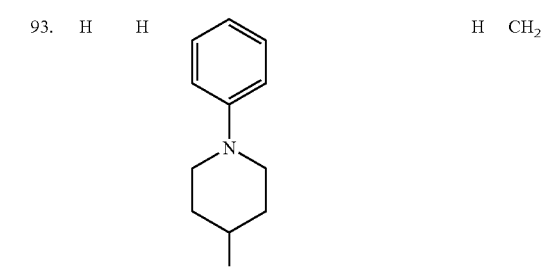 | H | CH₂ |

TABLE-continued

EXAMPLES C

| # | R¹ | R² | R³ | R⁴ | A |
|---|----|----|----|----|----|
| 94. | H | H | (3-(N-SO₂Et)-N-(CH₂C(O)NMe₂)amino)benzyl | H | CH₂ |
| 95. | H | H | (3-(N-SO₂Me)-N-(CH₂C(O)NMe₂)amino)benzyl | H | CH₂ |
| 96. | H | H | (3-(N-SO₂cPr)-N-(CH₂C(O)NMe₂)amino)benzyl | H | CH₂ |
| 97. | H | H | trans-4-(2-methylthiazol-4-yl)cyclohexyl | H | CH₂ |
| 98. | H | H | (3-(N-SO₂Me)-N-(oxazol-2-ylmethyl)amino)benzyl | H | CH₂ |
| 99. | H | H | (2-(N-SO₂Me)-N-(CH₂C(O)NMe₂)amino)benzyl | H | CH₂ |
| 100. | CHO | H | (3-(N-SO₂Me)-N-(CH₂C(O)NMe₂)amino)benzyl | H | CH₂ |
| 104. | H | H | 2-phenylethyl | H | CH₂ |
| 105. | H | H | 2-morpholinoethyl | H | CH₂ |

EXAMPLES C

| # | R¹ | R² | R³ | R⁴ | A |
|---|----|----|----|----|----|
| 106. | H | H | 1-methylpiperidin-4-ylmethyl | H | CH₂ |
| 107. | H | H | (tetrahydro-2H-pyran-4-yl)methyl | H | CH₂ |
| 108. | H | H | bicyclo[2.2.1]heptan-2-yl | H | CH₂ |
| 109. | H | H | 2-hydroxy-1-phenylethyl | H | CH₂ |
| 110. | H | H | cyclohexyl | H | CH₂ |
| 111. | H | H | 4-methyltetrahydro-2H-pyran-4-yl | H | CH₂ |
| 112. | H | H | (S)-2-hydroxy-1-phenylethyl | H | CH₂ |
| 113. | H | H | 2-(dimethylamino)-2-oxoethyl | H | CH₂ |
| 114. | H | H | 3-phenylcyclopentyl | H | CH₂ |
| 115. | H | H | (1R,2S)-2-phenylcyclopropyl | H | CH₂ |
| 116. | H | H | (1S,2S)-2-phenylcyclopropyl | H | CH₂ |
| 117. | H | H | trans-4-morpholinocyclohexyl | H | CH₂ |
| 118. | H | H | trans-4-(4-methylpiperazin-1-yl)cyclohexyl | H | CH₂ |

EXAMPLES C
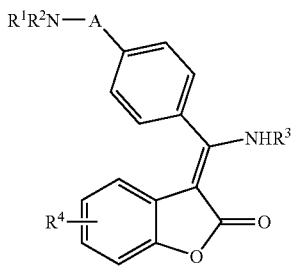
| # | R¹ | R² | R³ | R⁴ | A |
|---|---|---|---|---|---|
| 119. | H | H | 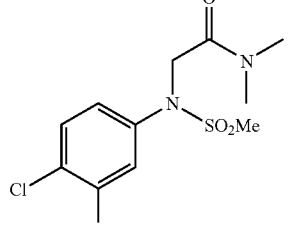 | H | CH₂ |
| 120. | H | H | 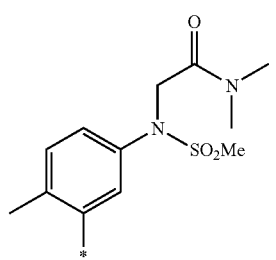 | H | CH₂ |
| 121. | H | H | 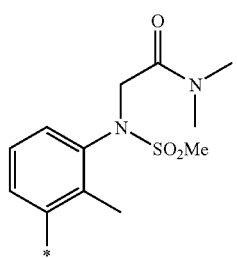 | H | CH₂ |
| 122. | H | H | 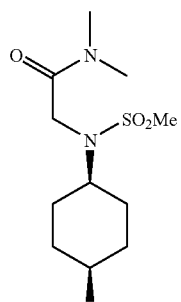 | H | CH₂ |
| 123. | H | H | 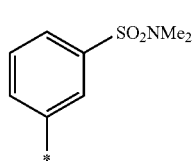 | H | CH₂ |
EXAMPLES C
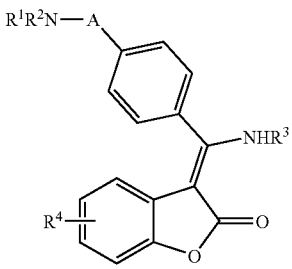
| # | R¹ | R² | R³ | R⁴ | A |
|---|---|---|---|---|---|
| 124. | H | H | 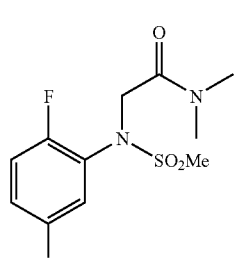 | H | CH₂ |
| 125. | H | H | 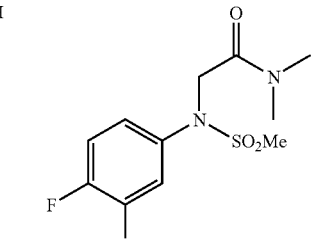 | H | CH₂ |
EXAMPLE D
Other Examples according to the invention are as follows:
Example 101
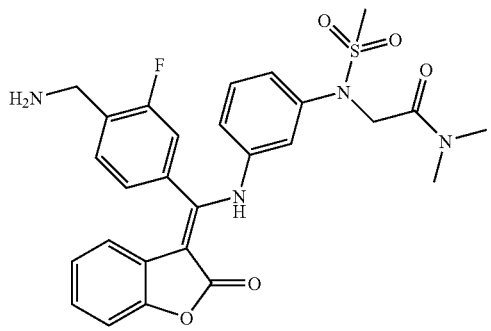

Example 102

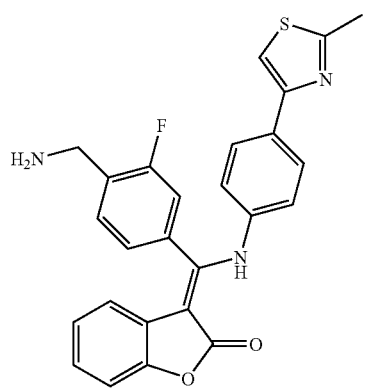

Example 103

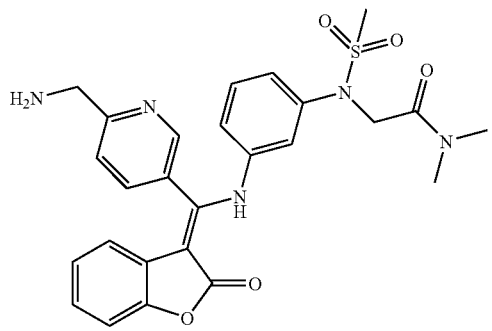

General synthesis scheme 1 is shown below, according to which the compounds of formula 1 according to the invention (coumaranones and indolinones) may be prepared. Instead of the allyloxycarbonyl protecting group used in Scheme 1 to protect the amino function, it is also possible to use other protecting groups, preferably the tert-butyloxycarbonyl protecting group (BOC protecting group).

Synthesis Scheme 1

1. Coupling of the tBu-O protecting group to the substituted benzoic acid

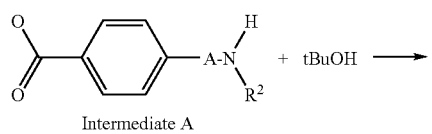

2. Coupling of the alkyloxycarbonyl protecting group to intermediate B

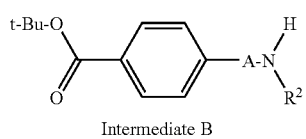

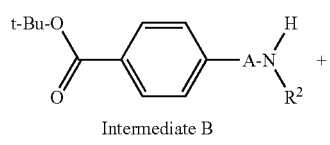

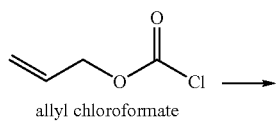

allyl chloroformate

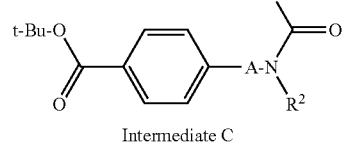

Intermediate C

3. Cleaving of the tBu-O protecting group

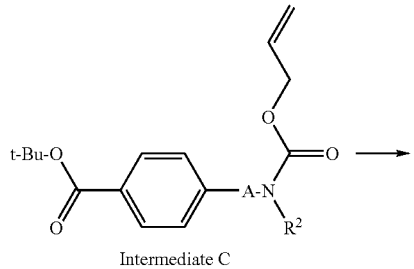

Intermediate C

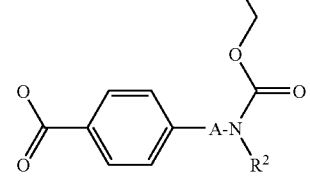

Intermediate D

4. Coupling of the intermediate D to coumaranone or indolinone

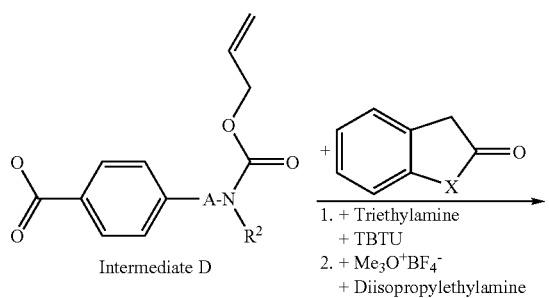

Intermediate D

1. + Triethylamine
   + TBTU
2. + Me₃O⁺BF₄⁻
   + Diisopropylethylamine

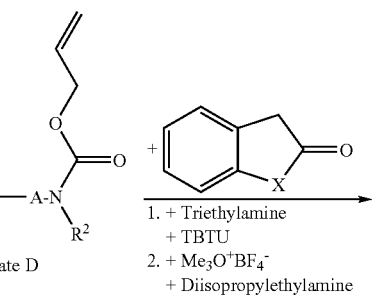

Intermediate E

5. Coupling of the intermediate E to an R³-substituted amine

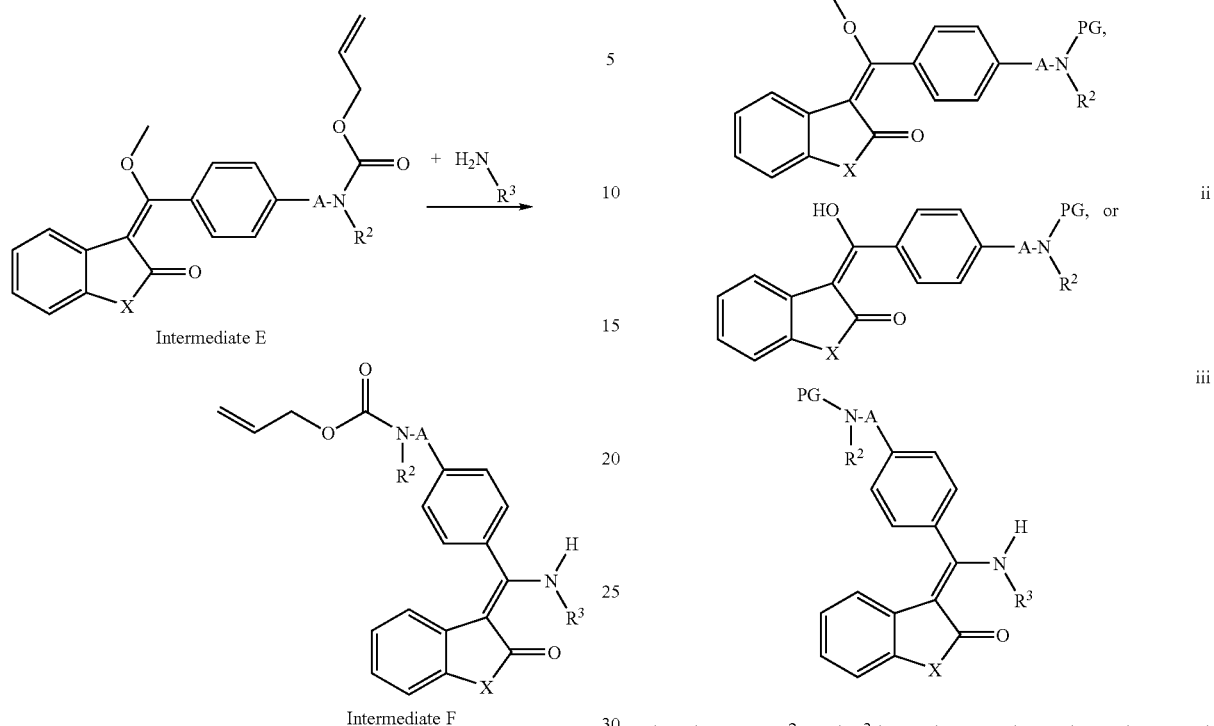

Intermediate E

Intermediate F

6. Cleaving of the allyloxycarbonyl protecting group from intermediate F

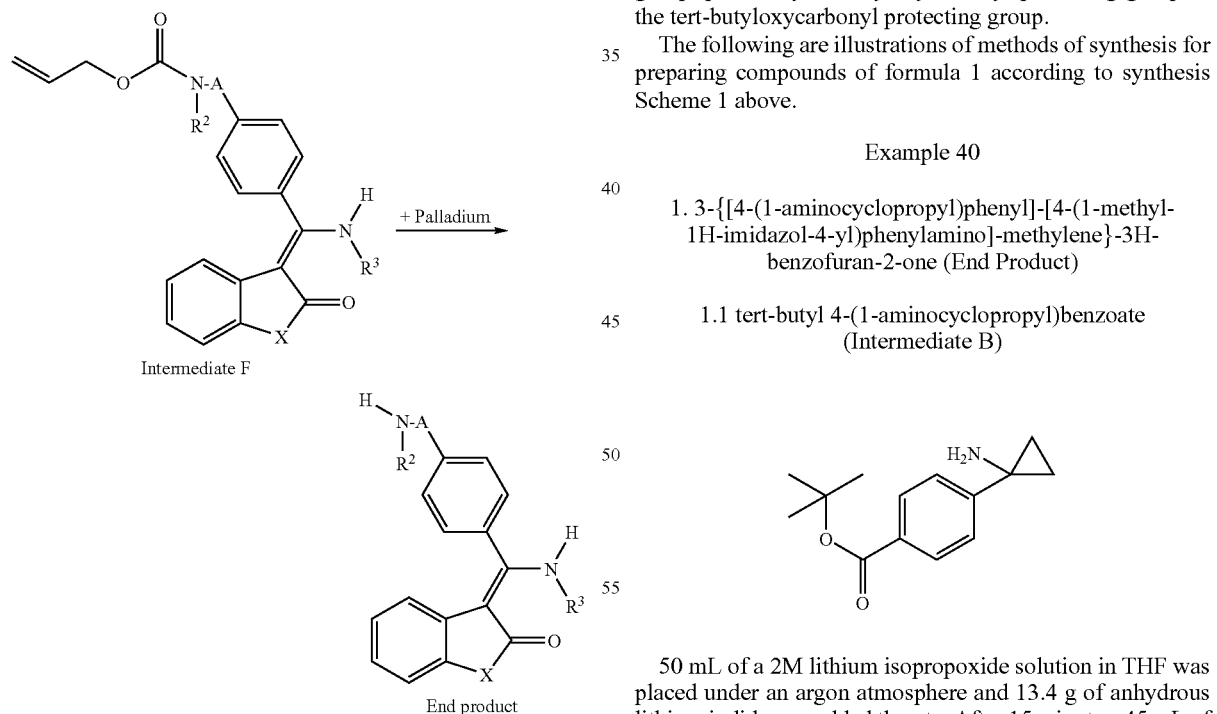

Intermediate F

End product

The present invention further relates to all intermediate products of the process according to Scheme 1, particularly the intermediate products according to formulae i, ii, or iii wherein X, A, R², and R³ have the meanings given above and PG (=protective group) is hydrogen or a suitable protecting group, preferably the allyloxycarbonyl protecting group or the tert-butyloxycarbonyl protecting group.

The following are illustrations of methods of synthesis for preparing compounds of formula 1 according to synthesis Scheme 1 above.

Example 40

1. 3-{[4-(1-aminocyclopropyl)phenyl]-[4-(1-methyl-1H-imidazol-4-yl)phenylamino]-methylene}-3H-benzofuran-2-one (End Product)

1.1 tert-butyl 4-(1-aminocyclopropyl)benzoate (Intermediate B)

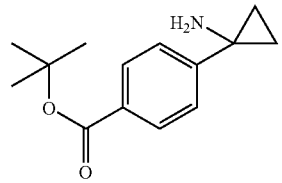

50 mL of a 2M lithium isopropoxide solution in THF was placed under an argon atmosphere and 13.4 g of anhydrous lithium iodide was added thereto. After 15 minutes, 45 mL of a 1M methyltitanium isopropoxide solution in THF was added. Then the mixture was combined with 8.1 g of tert-butyl 4-cyanobenzoate and stirred for 10 minutes. Then within 60 minutes, 47.3 mL of a 15% diethylzinc solution in hexane was added thereto and the mixture was stirred for 12 hours at RT. After hydrolysis with 20 mL of water, it was stirred for a further 30 minutes, filtered off, and washed 3×

1.2 tert-butyl 4-(1-allyloxycarbonylaminocyclopropyl)benzoate (Intermediate C)

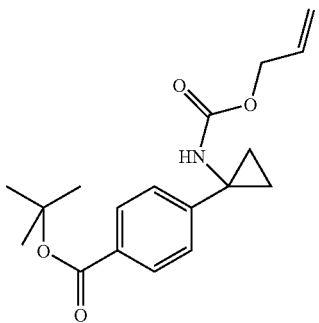

3 g of tert-butyl 4-(1-aminocyclopropyl)benzoate was placed in 30 mL of dichloromethane and 1.8 mL of pyridine. The solution was cooled to 0° C. and 1.2 mL of allyl chloroformate (dissolved in 5 mL of dichloromethane) was added dropwise at 0° C.-5° C. The mixture was left to react for 30 minutes at 0° C. and 2 hours at RT. The solution was combined with silica gel and evaporated down to the residue. This was chromatographed with dichloromethane on silica gel 70. Yield: 1.46 g of oil.

1.3 4-(1-allyloxycarbonylaminocyclopropyl)benzoic acid

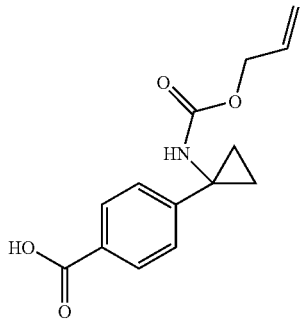

A solution of 1.46 g of tert-butyl 4-(1-allyloxycarbonylaminocyclopropyl)benzoate in 10 mL of acetonitrile was combined with 1 g of montmorillonite and refluxed for 3 hours. Then more montmorillonite was added and the mixture was boiled for 4 hours. The suspension was filtered hot, the inorganic material was extracted 3× with hot acetonitrile and filtered off, and the acetonitrile solutions were combined and evaporated down. Residue: 0.8 g of crystals.

1.4 allyl (1-{4-[dihydroxy-(2-oxobenzofuran-3-ylidene)methyl]phenyl}cyclopropyl)-carbamate (Intermediate D)

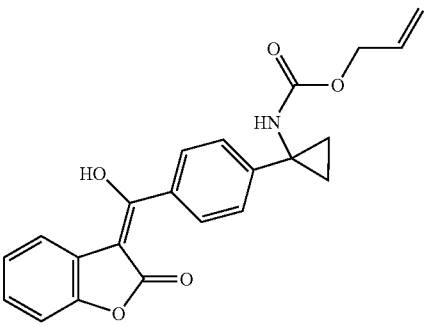

0.8 g of 4-(1-allyloxycarbonylaminocyclopropyl)benzoic acid and 0.585 mL of triethylamine were dissolved in 10 mL of anhydrous DMF and combined with 1.16 g of TBTU, stirred for 15 minutes at RT, then combined with 0.4 g of coumaranone and stirred for a further 10 minutes. While cooling with the ice bath, 0.42 g of NaH was added batchwise as a 60% suspension in white oil, the mixture was stirred for 2 hours at RT and, once the reaction had ended, the mixture was diluted with water to a total volume of approximately 150 mL. The mixture was acidified with 2N acetic acid. The crystals were suction filtered and washed with water. Yield: 1.1 g of solid with a melting point of 125° C.-126° C.

1.5 allyl (1-{4-[dimethoxy-(2-oxobenzofuran-3-yliden)methyl]phenyl}cyclopropyl)-carbamate (Intermediate E)

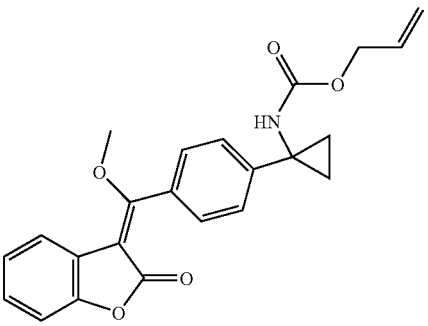

1 g of allyl (1-{4-[hydroxy-(2-oxobenzofuran-3-ylidene)methyl]phenyl}cyclopropyl)-carbamate, 0.78 g of trimethyloxonium tetrafluoroborate (Meerwein salt), and 1 mL of diisopropylethylamine (Hünig base) were refluxed in 20 mL of dichloromethane for 2 hours, zo then another 1 mL of Hünig base and 0.5 g of Meerwein salt were added and the mixture was refluxed again for 2 hours. After cooling, the mixture was extracted 3× with water, and the organic phase was dried over MgSO₄ and evaporated down to the residue. Yield: 1.05 g of crude.

83

1.6 allyl (1-{4-[[4-(1-methyl-1H-imidazol-4-yl)phe-nylamino]-(2-oxobenzofuran-3-ylidene)methyl]phenyl}cyclopropyl)carbamate (Intermediate F)

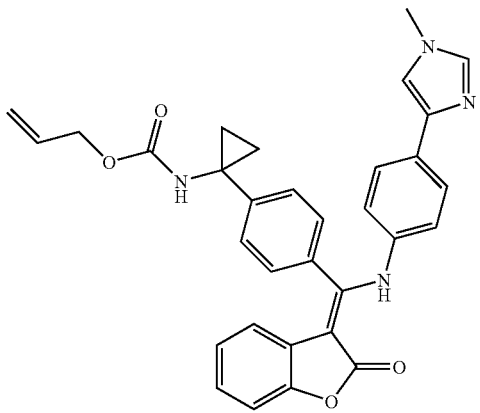

1.05 g of allyl (1-{4-[methoxy-(2-oxobenzofuran-3-ylidene)methyl]phenyl}cyclopropyl)-carbamate and 0.47 g of 4-(4-aminophenyl)-1-methylimidazole in 3 mL of DMPU were reacted in the microwave reactor at 180° C. After cooling, the mixture was diluted to 150 mL with ethyl acetate, extracted 2× with water, and the organic phase was dried over $MgSO_4$ and evaporated down to the residue with silica gel. The substance was chromatographed with dichloromethane/methanol (97:3) on silica gel 70 at a flow rate of 30 mL/min Residue: 0.6 g of yellow oil.

1.7 3-{[4-(1-aminocyclopropyl)phenyl]-[4-(1-me-thyl-1H-imidazol-4-yl)phenylamino]-methylene}-3H-benzofuran-2-one (End product)

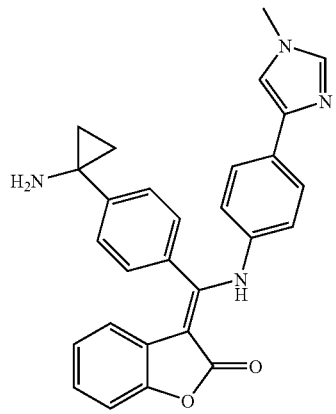

84

0.58 g of allyl (1-{4-[[4-(1-methyl-1H-imidazol-4-yl)phe-nylamino]-(2-oxobenzofuran-3-ylidene)methyl]phenyl}cyclopropyl)carbamate was dissolved in 20 mL of dichloromethane.

The solution was freed from oxygen using argon. Then at RT, 0.52 mL of diethylamine and 0.058 g of tetrakis(triph-enylphosphine)palladium (0) were added. The mixture was stirred for 2 hours at RT, the suspension was evaporated down with silica gel and chromatographed with dichloromethane/methanol (97:3) on silica gel 70 at a flow rate of 30 mL/min. The clean fractions were combined, evaporated down to the residue, dissolved in dichloromethane, filtered, and combined with diisopropyl ether. The dichloromethane was distilled off, the crystals formed were suction filtered and washed with diisopropyl ether. Yield: 0.26 g of yellow crystals, melting point 190° C.-191° C., as base. $R_f$ value: 0.51 (dichloromethane/methanol (9:1)).

The following compounds were prepared analogously to Synthesis Scheme 1 or to Example 40:

| Example | salt form | melting point (° C.) |
|---------|-----------|----------------------|
| 60 | x HCl | >250 |
| 61 | x HCl | 185-187 |
| 64 | x HCl | 261-262 |
| 65 | x HCl | 210-211 |
| 67 | x HCl | 254-255 |
| 74 | x HCl | 285-286 |
| 77 | x HCl | 275-276 |
| 78 | x HCl | 214-216 |
| 37k | x HCl | 263-265 |
| 37m | x HCl | >270 |
| 68 | x HCl | 286-287 decomp. |
| 97 | x HCl | 234-235 |
| 102 | base | 196-197 |

Scheme 2 shows the method of preparation for synthesizing the compound according to Example 47. The majority of the compounds of formula 1 according to the invention (coumaranones and indolinones) may also be prepared analogously to this preparation method according to Scheme 2, particularly the compounds according to the invention mentioned on the following pages.

Scheme 2

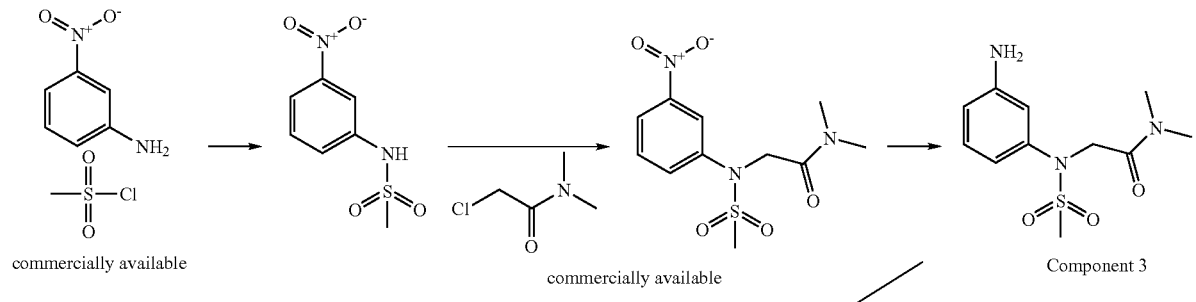

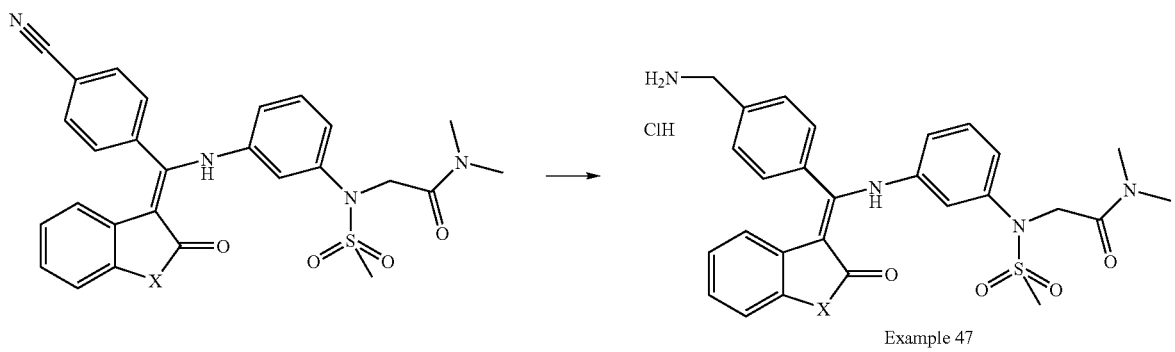

Example 47

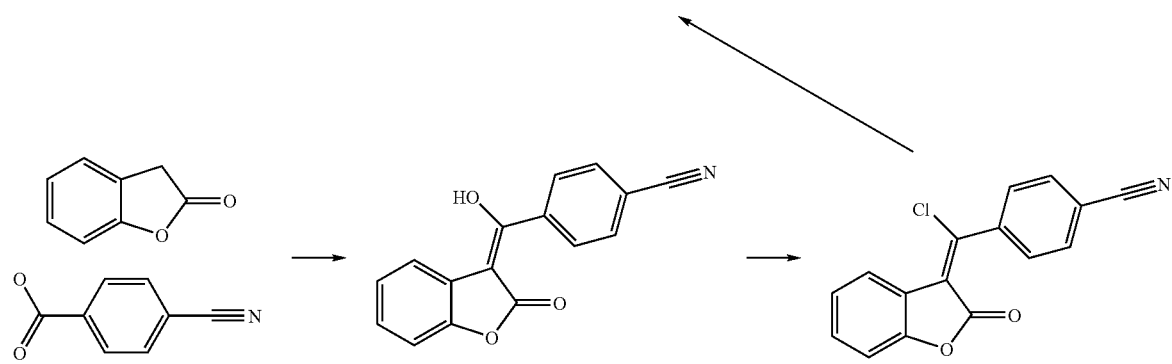

The present invention further relates to all the intermediate products of the process according to Scheme 2, particularly the intermediate products according to formulae I, II, III, IV, or V

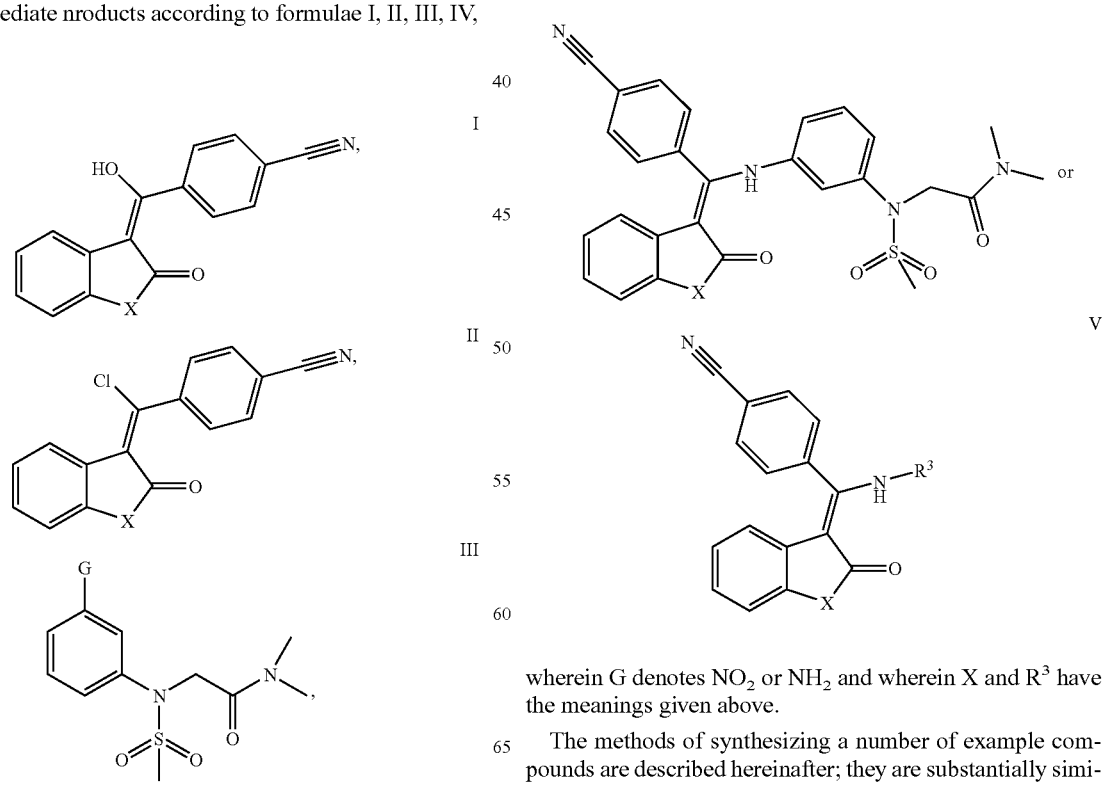

wherein G denotes $NO_2$ or $NH_2$ and wherein X and $R^3$ have the meanings given above.

The methods of synthesizing a number of example compounds are described hereinafter; they are substantially similar to Synthesis Scheme 2 described above.

Example 36

2. 3-{(4-aminomethylphenyl)-[4-(1-methyl-1H-imidazol-4-yl)phenylamino]methylene}-1-methyl-1,3-dihydroindol-2-one

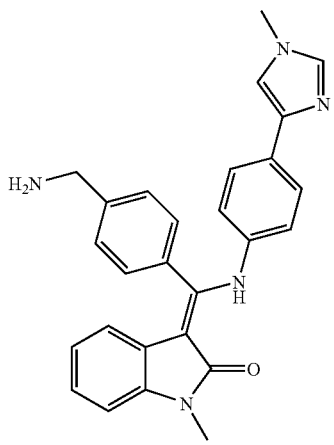

Starting from 4-cyanobenzoic acid, synthesis was carried out analogously to Example 40. Only the final step differed as follows. 6.15 g of 3-{(4-cyanophenyl)-[4-(1-methyl-1H-imidazol-4-yl)phenylamino]methylene}-1-methyl-1,3-dihydroindol-2-one was dissolved in 200 mL of methanolic ammonia and THF and hydrogenated with 5 g of Raney nickel at RT and under a pressure of 50 psi. After about 10 hours, the catalyst was removed by suction filtering and the filtrate was again filtered through a glass filter, evaporated down, and the crystalline residue was filtered with diisopropyl ether suction. The crystals were suspended in 400 mL of methanol, adjusted to pH 1 with 10% ethanolic hydrochloric acid, and heated to boiling temperature. The mixture was filtered and the filtrate was evaporated down to a residual volume of about 100 mL and combined with 300 mL of ethanol. After further evaporation to approximately 100 mL residual volume, the substance crystallized out. After cooling, it was suction filtered and washed with ice-cold ethanol. Yield: 6.15 yellow crystals; melting point>300° C.; $R_f$ value=0.32 (dichloromethane/methanol/ammonia (85:15:1)).

The following were prepared analogously:

| Example | salt form | melting point (° C.) | $R_f$ value |
|---|---|---|---|
| 1 | base | | |
| 2 | x TFA | | 0.38 ($CH_2Cl_2/CH_3OH/NH_3$ 9:1:0.1) |
| 3 | x TFA | | 0.5 ($CH_2Cl_2/CH_3OH/NH_3$ 4:1:0.1) |
| 4 | base | | 0.34 ($CH_2Cl_2/CH_3OH/NH_3$ 9:1:0.1) |
| 5 | x TFA | | 0.25 ($CH_2Cl_2/CH_3OH/NH_3$ 4:1:0.1) |
| 6 | base | | 0.27 ($CH_2Cl_2/CH_3OH/NH_3$ 9:1:0.1) |
| 7 | base | | 0.54 ($CH_2Cl_2/CH_3OH/NH_3$ 4:1:0.1) |
| 8 | base | | 0.33 ($CH_2Cl_2/CH_3OH/NH_3$ 9:1:0.1) |
| 9 | base | | 0.21 ($CH_2Cl_2/CH_3OH/NH_3$ 9:1:0.1) |
| 10 | x HCl | 294 decomp. | |
| 11 | base | | 0.27 ($CH_2Cl_2/CH_3OH/NH_3$ 9:1:0.1) |
| 12 | x HCl | 272 | |
| 13 | x HCl | >250 | |
| 15 | x HCl | 278 | |
| 16 | x HCl | 214-215 decomp. | |
| 17 | x HCl | >245 decomp. | |
| 18 | base | 225 decomp. | |
| 19 | x HCl | 295-296 | |
| 20 | x HCl | 265-267 | |
| 21 | x HCl | 274-275 | |
| 22 | x HCl | 259-260 decomp. | |
| 23 | x HCl | 281 decomp. | |
| 24 | x HCl | 245-246 decomp. | |
| 26 | x HCl | >260 decomp. | |
| 27 | base | 230-232 | |
| 28 | base | 153-155 | |
| 29 | base | 168-171 | |
| 30 | base | 233-238 | |
| 31 | base | 194-197 | |
| 32 | x HCl | 210-212 | |
| 33 | base | 157-159 | |
| 34 | base | 229 | |
| 35 | base | 228 | |
| 36 | base | 214-217 | |
| 37a | base | 204-206 | |
| 37b | base | 214-216 | |
| 37c | base | 186-188 | |
| 37d | base | 227-229 | |
| 37e | base | 263-265 | |
| 37f | base | 198-200 | |
| 37g | x HCl | 255-256 | |
| 37h | x HCl | 284 | |
| 37i | x HCl | 251-252 | |
| 37j | x HCl | 226-227 | |
| 37l | base | 172-173 | |
| 37n | x HCl | 195-198 | |
| 37o | x HCl | 297-298 | |
| 39 | x HCl | >290 | |

-continued

| Example | salt form | melting point (° C.) | R_f value |
|---|---|---|---|
| 41 | base | 167-169 | |
| 42 | base | 201-203 | |
| 43 | x HCl | 95-97 decomp. | |
| 44 | base | 222-224 | |
| 45 | base | 208-210 | |
| 46 | base | 186-188 | |
| 47 | x HCl | 274 | |
| 48 | x HCl | 186-188 | |
| 49 | base | 171-173 | |
| 50 | base | 164-166 | |
| 51 | base | 177-179 | |
| 52 | x HCl | 232-233 | |
| 53 | x HCl | >285 | |
| 54 | x HCl | 245-247 | |
| 55 | base | 149-151 | |
| 57 | base | 161-164 | |
| 58 | base | 168-172 | |
| 59 | base | 153-156 | |
| 62 | x HCl | 285-286 | |
| 63 | x HCl | 289-290 | |
| 66 | base | 215-217 | |
| 69 | base | 204-205 | |
| 70 | x HCl | 285-286 | |
| 71 | x HCl | >290 | |
| 72 | x HCl | 289 | |
| 73 | base | 163-166 | |
| 76 | x HCl | 288 | |
| 79 | base | 182-184 | |
| 80 | base | 135-137 | |
| 81 | x HCl | 294-295 | |
| 82 | x HCl | 254-255 | |
| 83 | x HCl | >275 | |
| 84 | x HCl | 215-220 | |
| 85 | base | 135-137 | |
| 86 | x HCl | 207 | |
| 87 | x HCl | 253-254 | |
| 88 | x HCl | >290 | |
| 89 | x HCl | >270 | |
| 90 | x HCl | 85-88 (amorphous?) | |
| 91 | x HCl | 283-284 | |
| 92 | x TFA | amorphous | |
| 93 | base | 161-162 | |
| 94 | x HCl | 271-272 | |
| 95 | x HCl | 188 | |
| 96 | x HCl | 268-269 | |
| 98 | x HCl | 241 decomposition | |
| 99 | x HCl | 196 | |
| 100 | — | 140 | |
| 101 | x HCl | 253-254 | |
| 103 | x TFA | amorphous | |

| Example | m + H | R_f value | retention time [min] |
|---|---|---|---|
| 104 | | 0.5 | |
| 105 | 380 | | |
| 106 | | 0.5 | |
| 107 | | 0.4 | |
| 108 | | 0.5 | |
| 109 | | 0.2 | |
| 110 | | 0.4 | |
| 111 | | 0.5 | |
| 112 | | 0.3 | |
| 113 | 352 | | |
| 114 | | 0.3 | |
| 115 | | 0.6 | |
| 116 | | 0.4 | |
| 117 | | 0.4 | |
| 118 | | 0.2 | |
| 119 | | 0.3 | |
| 120 | | 0.3 | |
| 121 | | 0.3 | |
| 122 | | | 1.7 |
| 123 | | 0.6 | |
| 124 | 539 | | |
| 125 | | 0.2 | |

Method of Carrying Out Thin Layer Chromatography to Determine the R_f Values:

The solid phase used was silica gel 60 F254 (made by Merck) and the liquid phase, unless otherwise specified, was a (9:1:0.1) mixture of dichloromethane:methanol:ammonia.

Chromolith Method:

HPLC-MS-1 Waters ZMD, Alliance 2690/2695 HPLC, Waters 2700 Autosampler, Waters 996/2996 diode array detector. The mobile phase used was:
A: water with 0.10% TFA
B: acetonitrile with 0.10% TFA

| time in min | % A | % B | flow rate in mL/min |
| --- | --- | --- | --- |
| 0.00 | 95 | 5 | 2.00 |
| 0.10 | 95 | 5 | 2.00 |
| 2.10 | 2 | 98 | 2.00 |
| 3.00 | 2 | 98 | 2.00 |
| 3.25 | 95 | 5 | 2.00 |

The stationary phase used was a Merck Chromolith™ Speed-ROD RP-18e column, 4.6 mm×50 mm (column temperature: constant at 25° C.).

The diode array detection took place in a wavelength range of 210-400 nm.

Example 14

3. 4-[[4-(1-methyl-1H-imidazol-4-yl)phenylamino]-(2-oxo-1-phenyl-1,2-dihydroindol-3-ylidene)methyl]benzamidine

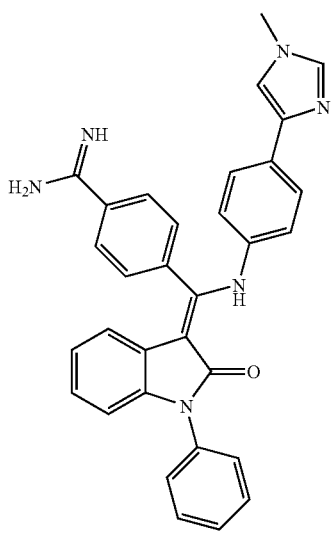

Starting from 4-cyanobenzoic acid synthesis was carried out analogously to Example 40. Only the last step differed as follows. 0.6 g of 3-{(4-cyanophenyl)-[4-(1-methyl-1H-imidazol-4-yl)phenylamino]methylene}-1-phenyl-1,3-dihydroindol-2-one was dissolved in 20 mL of dichloromethane and 30 mL of 40% ethanolic hydrochloric acid and stored in the refrigerator for 12 hours. The solution was evaporated down to the residue, combined with 50 mL of 6N ethanolic ammonia solution, and refluxed for 3 hours. The solution was evaporated down with silica gel and purified by chromatography with dichloromethane/methanol (8:2) on silica gel 70 (flow rate 20 mL/min). The clean fractions were evaporated down and the crystals with acetone, suction filtered, and washed. Yield: 0.2 g of yellow crystals; melting point 241° C. (decomp.).

Example 25 was prepared analogously (melting point 230° C.-232° C. as hydrochloride), as was Example 38 (melting point>275° C. with decomp. as hydrochloride).

Example 56

4. 3-{[4-(1-amino-1-methylethyl)phenyl]-[4-(1-methyl-1H-imidazol-4-yl)phenylamino]-methylene}-3H-benzofuran-2-one 4.1 1-[4-(4,4-dimethyl-4,5-dihydroxazol-2-yl)phenyl]-1-methylethylamine

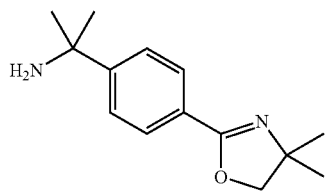

130 g of anhydrous cerium (III) chloride was suspended in 1 L of THF and stirred for 1 hour, cooled to −60° C. with thorough mechanical stirring and combined dropwise with 330 mL of a 1.5M methyl lithium solution in THF/cumene, while the internal temperature did not rise above—50° C. The yellow suspension was stirred for 30 minutes and at −50° C. combined with a solution of 34.4 g of 2-(4-cyanophenyl)-4,4-dimethyl-4,5-dihydroxazole in 50 mL of THF. After another 12 hours, 330 mL of concentrated ammonia solution was added dropwise at −55° C., whereupon a violet precipitate was formed. It was allowed to come up to RT, filtered, and the residue was washed with 1 L of THF. The organic phase was evaporated down. The oily yellow residue was purified by chromatography (dichloromethane/methanol (9:1), silica gel 70, flow rate 50 mL/min). The clean fractions yielded 33.3 g of yellow oil with an $R_f$ value 0.20 (dichloromethane/methanol (7:3)).

4.2 tert-butyl {1-[4-(4,4-dimethyl-4,5-dihydroxazol-2-yl)phenyl]-1-methylethyl}carbamate

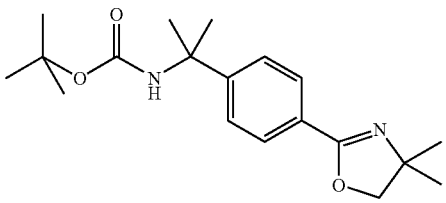

A solution of 0.4 g of sodium carbonate in 4 mL of water was added to a solution of 0.8 g of 1-[4-(4,4-dimethyl-4,5-dihydroxazol-2-yl)phenyl]-1-methylethylamine in 15 mL of dioxane. Then within 10 minutes, a solution of 0.83 g of Boc-anhydride in dioxane was added dropwise. The yellow solution was stirred for 12 hours at RT. The dioxane was distilled off and the aqueous residue was extracted 2× with ethyl acetate. The organic phases were combined, dried over $MgSO_4$, filtered, and evaporated down to the residue. After crystallization, 0.87 g of yellowish-white product was obtained.

4.3 4-(1-tert-butoxycarbonylamino-1-methylethyl)benzoic acid

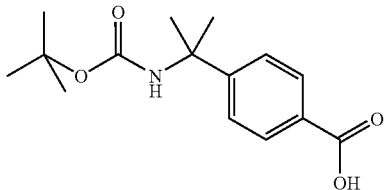

A solution of 0.83 g of tert-butyl {1-[4-(4,4-dimethyl-4,5-dihydroxazol-2-yl)phenyl]-1-methylethyl}carbamate and 3.1 mL of methyl iodide in 2 mL of DMF was stirred for 12 hours at 60° C. in a pressure tube reactor and, after cooling, evaporated down to the residue. The oil was stirred with 15 mL of 1M NaOH for 3 hours at RT. The suspension was extracted with ether. The aqueous phase was acidified to pH 2 with 1M HCl and the precipitate formed was taken up in ether. After the aqueous phase had been extracted twice more with ether, the organic phases were combined, dried over MgSO$_4$, filtered, and the filtrate was evaporated down to the residue. Yield: 0.4 g of crystals; $R_f$ value 0.41 (dichloromethane/methanol (9:1)).

The process used in Example 40 hereinbefore was used to cleave the Boc protecting group.

4.4 3-{[4-(1-amino-1-methyl ethyl)phenyl]-[4-(1-methyl-1H-imidazol-4-yl)phenylamino]methylene}-3H-benzofuran-2-one

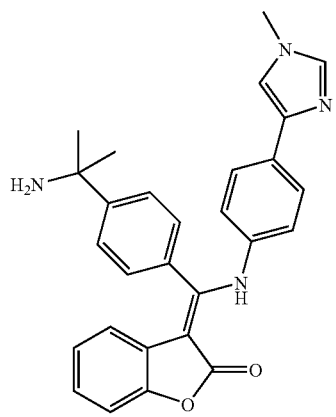

2.5 g of tert-butyl (1-methyl-1-{4-[[4-(1-methyl-1H-imidazol-4-yl)phenylamino]-(2-oxobenzofuran-3-ylidene)methyl]phenyl}ethyl)carbamate (N-Boc derivative of Example 56) was dissolved in 50 mL of dioxane and combined with 50 mL of a 4N solution of hydrogen chloride in dioxane. The solution was stirred for 1 hour at RT and evaporated down. The residue was dissolved in 50 mL of methanol and evaporated down with another 150 mL of isopropanol almost to the residue and then crystallized. After diluting with acetone, the product was suction filtered and washed with acetone. Yield: 1.9 g of yellow crystals of melting point>280° C. as hydrochloride; $R_f$ value: 0.18 (dichloromethane/methanol (8:2)).

The components of the synthesis described above are known in the literature, commercially available or prepared as follows:

Component 1

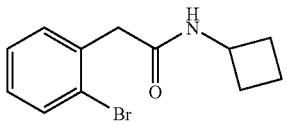

26.3 g of 2-bromophenylacetic acid was dissolved in 200 mL of dichloromethane and combined with 15 mL of oxalyl chloride and one drop of DMF. After 1 hour at RT, the solution was evaporated down and the acid chloride was further used directly. The acid chloride was dissolved in 40 mL of dichloromethane and added dropwise to a solution of 9 g of cyclobutylamine and 27 mL of diisopropylethylamine in dichloromethane at 15° C.-20° C. After 12 hours at RT, the dichloromethane was distilled off, the residue was dissolved in 600 mL of ethyl acetate and extracted 2× with 4N HCl, 2× with 4N NaOH, and 3× with water. The organic phase was dried over MgSO$_4$, filtered, and evaporated down to the crystalline residue. After the addition of diisopropyl ether, the mixture was suction filtered and 24.1 g of 2-bromophenylacetic acid-cyclobutylamide was obtained. Melting point 159° C.-161° C.; $R_f$ value: 0.67 (dichloromethane/methanol (9:1)).

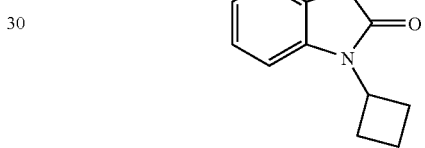

400 mL of toluene was degassed with argon and then 13.4 g of 2-bromophenylacetic acid-cyclobutylamide, 9.7 g of powdered K$_2$CO$_3$, 0.9 g of tris(dibenzylideneacetone)dipalladium (0) and 1.2 g of tri-o-tolylphosphine were added. After 72 hours stirring at 100° C. and cooling, the mixture was diluted to 2 L with diethyl ether, filtered to remove insoluble matter, and evaporated down to the residue. After crystallization in diisopropyl ether, the mixture was suction filtered and the filtrate was evaporated down to the residue with silica gel. The purification was carried out by chromatography on silica gel 60 (eluant: dichloromethane). Yield: 3.75 g of oil; $R_f$ value: 0.18 (dichloromethane).

Component 2

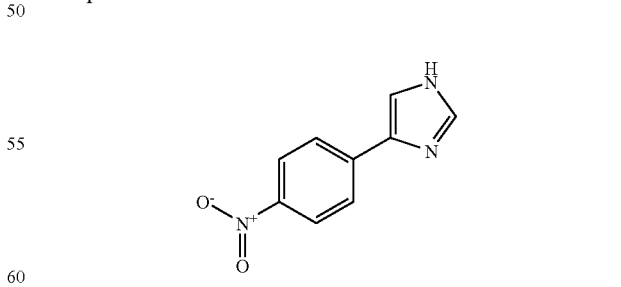

100 g of p-nitrophenacylbromide and 400 mL of formamide were stirred for 2 hours at 175° C. After cooling, the mixture was made alkaline with 20 mL of ammonia, stirred into 800 mL of water, and the precipitate was suction filtered. The crystals were recrystallized from methanol and suction filtered. Yield: 46.5 g; melting point 217° C.-219° C.

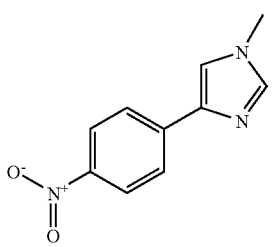

45 g of 1H-4-(4-nitrophenyl)imidazole was placed in 300 mL of DMSO and 30 g of potassium tert-butoxide was added batchwise while cooling with ice. The mixture was heated to RT and stirred for 1 hour. Then 16.5 mL of methyl iodide was added dropwise between 20° C.-25° C. and stirred for a further 2 hours at RT. Then the mixture was poured onto 300 g of ice, stirred, the precipitate formed was suction filtered and washed thoroughly with water. Yield: 39.8 g.

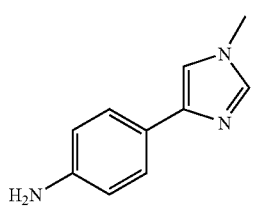

22 g of 1-methyl-4-(4-nitrophenyl)imidazole was dissolved in 1.6 L of methanol and combined with 4 g of Pd/C (10%). The mixture was hydrogenated at 50 psi and RT for approximately 5 hours. Then another gram of catalyst was added and the mixture was hydrogenated for 18 zo hours, then for a further 12 hours with the addition of another 2 g of catalyst. Finally, the catalyst was suction filtered and the filtrate was evaporated down. The residue was taken up in toluene and some methanol, and evaporated down somewhat until a dark-grey precipitate formed. This was suction filtered, taken up in methanol, combined with 4 g of activated charcoal, and filtered off. The filtrate was combined with 100 mL of toluene, concentrated by rotary evaporation, and crystallized. Yield: 22 g; $R_f$ value: 0.34 (dichloromethane/methanol (9:1)).

Component 3

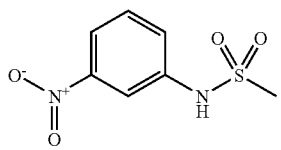

100 g of 3-nitroaniline was dissolved in 400 mL of pyridine and 57 mL of methanesulfonic acid chloride was added dropwise while cooling gently with ice. After 12 hours at RT, the red reaction mixture was poured onto 1.2 L of ice, stirred, suction filtered, and the solid was suspended with copious amounts of water, washed, and dried. Yield: 148 g of solid with a melting point of 165° C.-166° C.; $R_f$ value. 0.65 (dichloromethane/methanol (9:1)).

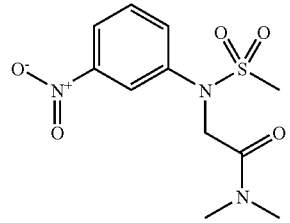

50 g of 3-methanesulfonylaminonitrobenzene was placed in 200 mL of DMF, 31 g of potassium tert-butoxide was added and the reaction mixture was stirred for 1 hour at RT. After the addition of 28.5 g of 2-chloro-N,N-dimethylacetamide, the mixture was stirred for 12 hours at 60° C. After cooling to RT, water was added and the mixture was extracted 5× with ethyl acetate. The organic phases were washed with water, dried over $MgSO_4$, filtered, and the filtrate was evaporated down to the residue. The residue was crystallized from diisopropylether. Yield: 31.5 g.

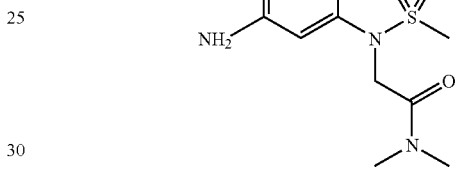

31.5 g of 2-(N-methanesulfonyl-N-(3-nitrophenyl)amino)-N,N-dimethylacetamide was hydrogenated with 3 g of Pd/C at RT and 50 psi in ammoniacal methanol for 24 hours. Then the catalyst was suction filtered while warm and washed several times with ethyl acetate. The filtrate was evaporated down to the residue. Yield: 20 g of solid with a melting point of 143° C.-144° C.

Component 4

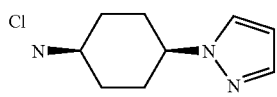

9.25 g (47 mmol) of 4-aminophenylpyrazole hydrochloride is placed in 150 mL of methanol and hydrogenated with 1.00 g of Nishimura catalyst at ambient temperature under a pressure of 50 psi. Then the catalyst is filtered off and the filtrate is concentrated by evaporation. The residue is crystallized from acetonitrile and the enantiomers are obtained by chromatographic separation. Yield: 1.89 g (20%) of cis compound; NMR: LH201668; m.p.: 175° C.-177° C.

Component 5

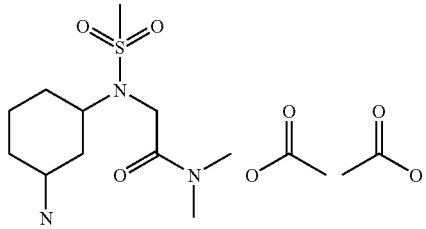

4.00 g (15 mmol) of Component 3 is placed in 60 mL of glacial acetic acid and hydrogenated with 0.600 g of Nishimura catalyst at ambient temperature under a pressure of 50 psi. Then the catalyst is filtered off and the filtrate is concentrated by evaporation. The residue is dissolved in a little water, treated with activated charcoal, and filtered. The filtrate is lyophilized. Yield: 4.90 g (84%); NMR: LH201565.
Component 6

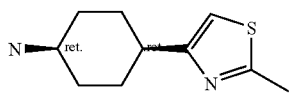

2-methyl-2-(4-nitrophenyl)-[1,3]dioxolane: 33.03 g (200 mmol) of 4-nitroacetophenone, 12.30 mL (220 mmol) of ethylene glycol, and 1.00 g (5 mmol) of p-toluenesulfonic acid are placed in 250 mL of toluene, then refluxed for 16 hours using the water separator. Then the reaction mixture is cooled and extracted with water. The organic phase is dried and evaporated to dryness. The residue is extracted with diisopropyl ether and suction filtered. Yield: 34.45 g (82%).

4-(2-methyl-[1.3]dioxolan-2-yl)cyclohexylamine: 8.37 g (40 mmol) of 2-methyl-2-(4-nitrophenyl)-[1,3]dioxolane is placed in 160 mL of methanol and hydrogenated with 1.00 g of Nishimura catalyst at ambient temperature under a pressure of 50 psi. Then the catalyst is filtered off and the filtrate is concentrated by evaporation. The residue is dissolved in cyclohexane, filtered to remove insoluble matter, and the filtrate is evaporated to dryness. Yield: 7.00 g (94%), cis/trans ratio 77:23; NMR: LG201616.

9H-fluoren-9-ylmethyl[4-(2-methyl-[1.3]dioxolan-2-yl)cyclohexyl]carbamate: A solution of 12.72 g (120 mmol) of sodium carbonate is placed in 120 mL of water and combined with a solution of 7.00 g (38 mmol) of 4-(2-methyl-[1,3]dioxolan-2-yl)cyclohexylamine (cis/trans mixture) in 50 g of dioxane. After cooling to 0° C., a solution of 10.09 g (39 mmol) of Fmoc-chloride in 100 g of dioxane is added dropwise within 0.2 hours. The reaction mixture is stirred for 16 hours with the cooling removed. Then the mixture is poured onto water and extracted with ethyl acetate. The organic phase is washed with water, dried, and evaporated to dryness. The residue is purified by chromatography. Yield: 13.10 g (85%) cis/trans ratio 4:1; NMR: LH201618.

9H-fluoren-9-ylmethyl (4-acetylcyclohexyl)carbamate: 13.10 g (32 mmol) of 9H-fluoren-9-ylmethyl[4-(2-methyl-[1,3]dioxolan-2-yl)cyclohexyl]carbamate (cis/trans mixture) and 1.30 g of p-toluenesulfonic acid are refluxed in 25 mL of water and 500 mL of acetone for 16 hours with stirring. Then the reaction mixture is concentrated by evaporation and the residue is dissolved in ethyl acetate and extracted with water. The organic phase is dried and evaporated to dryness. The residue is extracted with diisopropylether and suction filtered. Yield: 7.77 g (89%) of cis compound; NMR: LH201628.

9H-fluoren-9-ylmethyl[4-(2-bromoacetyl)cyclohexyl]carbamate: 7.77 g (21 mmol) of 9H-fluoren-9-ylmethyl (4-acetylcyclohexyl)carbamate (cis compound) is dissolved in 100 mL of methanol at ambient temperature and combined with 1.09 mL (21 mmol) of bromine. The mixture is stirred for 16 hours at ambient temperature, cooled, and the crystals precipitated are suction filtered. Yield: 6.35 g (50%); NMR: LG201641.

9H-fluoren-9-ylmethyl[4-(2-methylthiazol-4-yl)cyclohexyl]carbamate: 4.00 g (7 mmol) of 9H-fluoren-9-ylmethyl [4-(2-bromoacetyl)cyclohexyl]carbamate (cis compound) and 0.700 g (9 mmol) of thioacetamide are refluxed in 50 mL of acetonitrile for 72 hours with stirring. Then the reaction mixture is concentrated by evaporation, the residue is purified by chromatography. Corresponding fractions are combined and evaporated to dryness. The crystalline residue is extracted with diisopropyl ether and suction filtered. Yield: 1.10 g (39%) of cis compound; NMR: LH201648; m.p.: 140° C.-141° C.

4-(2-methylthiazol-4-yl)cyclohexylamine (Component 6): 1.10 g (2 mmol) of 9H-fluoren-9-ylmethyl[4-(2-methylthiazol-4-yl)cyclohexyl]carbamate (cis compound) and 15 mL of diethylamine are stirred in 30 mL of THF for 16 hours at ambient temperature. Then the reaction mixture is concentrated by evaporation and the residue is combined with THF and concentrated again by evaporation. The residue is purified by chromatography. Yield: 0.13 g (36%).

Indications

As has been found, the compounds of formula 1 are characterized by their wide range of applications in the therapeutic field. Particular mention should be made of those applications for which the compounds according to the invention of formula 1 are preferably suited on account of their pharmaceutical efficacy as PDE4 inhibitors. Examples include respiratory or gastrointestinal diseases or complaints, inflammatory diseases of the joints, skin, or eyes, cancers, and also diseases of the peripheral or central nervous system.

Particular mention should be made of the prevention and treatment of diseases of the airways and of the lung which are accompanied by increased mucus production, inflammations, and/or obstructive diseases of the airways. Examples include acute, allergic, or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, pediatric asthma, bronchiectases, pulmonary fibrosis, ARDS (acute adult respiratory distress syndrome), bronchial edema, pulmonary edema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis, or mucoviscidosis, or alpha1-antitrypsin deficiency.

Also deserving special mention is the treatment of inflammatory diseases of the gastrointestinal tract. Examples include acute or chronic inflammatory changes in gall bladder inflammation, Crohn's disease, ulcerative colitis, inflammatory pseudopolyps, juvenile polyps, colitis cystica profunda, pneumatosis cystoides intestinales, diseases of the bile duct, and gall bladder, e.g., gallstones and conglomerates, for the treatment of inflammatory diseases of the joints such as rheumatoid arthritis or inflammatory diseases of the skin and eyes.

Preferential mention should also be made of the treatment of cancers. Examples include all forms of acute and chronic leukemias such as acute lymphatic and acute myeloid leukemia, chronic lymphatic and chronic myeloid leukemia, and bone tumors such as osteosarcoma and all types of glioma such as oligodendroglioma and glioblastoma.

Preferential mention should also be made of the prevention and treatment of diseases of the peripheral or central nervous system. Examples of these include depression, bipolar or manic depression, acute and chronic anxiety states, schizophrenia, Alzheimer's disease, Parkinson's disease, acute and chronic multiple sclerosis, or acute and chronic pain as well as injuries to the brain caused by stroke, hypoxia, or craniocerebral trauma.

Particularly preferably the present invention relates to the use of compounds of formula 1 for preparing a pharmaceutical composition for the treatment of inflammatory or obstructive diseases of the upper and lower respiratory tract including the lungs, such as, for example, allergic rhinitis, chronic rhinitis, bronchiectasis, cystic fibrosis, idiopathic pulmonary fibrosis, fibrosing alveolitis, COPD, chronic bronchitis, chronic sinusitis, asthma, Crohn's disease, ulcerative colitis, particularly COPD, chronic bronchitis, and asthma.

It is most preferable to use the compounds of formula 1 for the treatment of inflammatory and obstructive diseases such as COPD, chronic bronchitis, chronic sinusitis, asthma, Crohn's disease, ulcerative colitis, particularly COPD, chronic bronchitis, and asthma.

It is also preferable to use the compounds of formula 1 for the treatment of diseases of the peripheral or central nervous system such as depression, bipolar or manic depression, acute and chronic anxiety states, schizophrenia, Alzheimer's disease, Parkinson's disease, acute and chronic multiple sclerosis, or acute and chronic pain as well as injuries to the brain caused by stroke, hypoxia, or craniocerebral trauma.

An outstanding aspect of the present invention is the reduced profile of side effects. This means, within the scope of the invention, being able to administer a dose of a pharmaceutical composition without inducing vomiting, preferably nausea and most preferably malaise in the patient. It is particularly preferable to be able to administer a therapeutically effective quantity of substance without inducing emesis or nausea, at every stage of the disease.

Combinations

The compounds of formula 1 may be used on their own or in conjunction with other active substances of formula 1 according to the invention. If desired the compounds of formula 1 may also be used in combination with other pharmacologically active substances. It is preferable to use for this purpose active substances selected, for example, from among betamimetics, anticholinergics, corticosteroids, other PDE4-inhibitors, LTD4-antagonists, EGFR-inhibitors, dopamine agonists, H1-antihistamines, PAF-antagonists, and PI3-kinase inhibitors or double or triple combinations thereof, such as, for example, combinations of betamimetics with corticosteroids, PDE4-inhibitors, EGFR-inhibitors, or LTD4-antagonists,
anticholinergics with betamimetics, corticosteroids, PDE4-inhibitors, EGFR-inhibitors, or LTD4-antagonists,
corticosteroids with PDE4-inhibitors, EGFR-inhibitors, or LTD4-antagonists
PDE4-inhibitors with EGFR-inhibitors, or LTD4-antagonists
EGFR-inhibitors with LTD4-antagonists
MRP4-inhibitors.

The invention also encompasses combinations of three active substances, each selected from one of the abovementioned categories of compounds.

Suitable betamimetics used are preferably compounds selected from among albuterol, bambuterol, bitolterol, broxaterol, carbuterol, clenbuterol, fenoterol, formoterol, arformoterol, zinterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenol, sulfonterol, tiaramide, terbutaline, tolubuterol, CHF-1035, HOKU-81, KUL-1248, 3-(4-{6-[2-hydroxy-2-(4-hydroxy-3-hydroxymethylphenyl)ethylamino]hexyloxy}butyl)benzylsulfonamide, 5-[2-(5.6-diethylindan-2-ylamino)-1-hydroxyethyl]-8-hydroxy-1H-quinolin-2-one, 4-hydroxy-7-[2-{[2-{[3-(2-phenylethoxy)propyl]sulfonyl}ethyl]amino}ethyl]-2(3H)benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{-4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert-butylamino)ethanol, 6-hydroxy-8-{1-hydroxy-2-[2-(4-methoxyphenyl)-1,1-dimethylethylamino]ethyl}-4H-benzo[1,4]oxazin-3-one, 6-hydroxy-8-{1-hydroxy-2-[2-(ethyl 4-phenoxyacetate)-1,1-dimethylethylamino]ethyl}-4H-benzo[1,4]oxazin-3-one, 6-hydroxy-8-{1-hydroxy-2-[2-(4-phenoxyacetic acid)-1,1-dimethylethylamino]ethyl}-4H-benzo[1,4]oxazin-3-one, 8-{2-[1,1-dimethyl-2-(2,4,6-trimethylphenyl)ethylamino]-1-hydroxyethyl}-6-hydroxy-4H-benzo[1,4]oxazin-3-one, 6-hydroxy-8-{1-hydroxy-2-[2-(4-hydroxyphenyl)-1,1-dimethylethylamino]ethyl}-4H-benzo[1,4]oxazin-3-one, 6-hydroxy-8-{1-hydroxy-2-[2-(4-isopropylphenyl)-1,1-dimethylethylamino]ethyl}-4H-benzo[1,4]oxazin-3-one, 8-{2-[2-(4-ethylphenyl)-1,1-dimethylethylamino]-1-hydroxyethyl}-6-hydroxy-4H-benzo[1,4]oxazin-3-one, 8-{2-[2-(4-ethoxyphenyl)-1,1-dimethylethylamino]-1-hydroxyethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)ethylamino]-2-methylpropyl}phenoxy)butyric acid, 8-{2-[2-(3.4-difluorophenyl)-1,1-dimethylethylamino]-1-hydroxyethyl}-6-hydroxy-4H-benzo[1,4]oxazin-3-one, and 1-(4-ethoxycarbonylamino-3-cyano-5-fluorophenyl)-2-(tert-butylamino)ethanol, optionally in the form of the racemates, enantiomers, diastereomers, and optionally in the form of the pharmacologically acceptable acid addition salts, solvates, or hydrates thereof.

Preferably the betamimetics are selected from among bambuterol, bitolterol, carbuterol, clenbuterol, fenoterol, formoterol, hexoprenaline, ibuterol, pirbuterol, procaterol, reproterol, salmeterol, sulfonterol, terbutaline, tolubuterol, 3-(4-{6-[2-hydroxy-2-(4-hydroxy-3-hydroxymethylphenyl)ethylamino]hexyloxy}butyl)benzenesulfonamide, 5-[2-(5.6-diethylindan-2-ylamino)-1-hydroxyethyl]-8-hydroxy-1H-quinolin-2-one, 4-hydroxy-7-[2-{[2-{[3-(2-phenylethoxy)propyl]sulfonyl}ethyl]amino}ethyl]-2(3H)benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert-butylamino)ethanol, 6-hydroxy-8-{1-hydroxy-2-[2-(4-methoxyphenyl)-1,1-dimethylethylamino]ethyl}-4H-benzo[1,4]oxazin-3-one, 6-hydroxy-8-{1-hydroxy-2-[2-(ethyl-4-phenoxyacetate)-1,1-dimethylethylamino]ethyl}-4H-benzo[1,4]oxazin-3-one, 6-hydroxy-8-{1-hydroxy-2-[2-(4-phenoxyacetic acid)-1,1-dimethylethylamino]ethyl}-4H- benzo[1,4]oxazin-3-one, 8-{2-[1,1-dimethyl-2-(2,4,6-trimethylphenyl)ethylamino]-1-hydroxyethyl}-6-hydroxy-4H-benzo[1,4]oxazin-3-one, 6-hydroxy-8-{1-hydroxy-2-[2-(4-hydroxyphenyl)-1,1-dimethylethylamino]ethyl}-4H-benzo[1,4]oxazin-3-one, 6-hydroxy-8-{1-hydroxy-2-[2-(4-isopropylphenyl)-1,1-dimethylethylamino]ethyl}-4H-benzo[1,4]oxazin-3-one, 8-{2-[2-(4-ethylphenyl)-1,1-dimethylethylamino]-1-hydroxyethyl}-6-hydroxy-4H-benzo[1,4]oxazin-3-one, 8-{2-[2-(4-ethoxyphenyl)-1,1-dimethylethylamino]-1-hydroxyethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)ethylamino]-2-methylpropyl}phenoxy)butyric acid, 8-{2-[2-(3,4-difluorophenyl)-1,1-dimethylethylamino]-1-hydroxyethyl}-6-hydroxy-4H-benzo[1,4]oxazin-3-one, and 1-(4-ethoxycarbonylamino-3-cyano-5-fluorophenyl)-2-(tert-butylamino)ethanol, optionally in the form of the racemates, enantiomers, diastereomers, and optionally in the form of the pharmacologically acceptable acid addition salts, solvates, or hydrates thereof.

Particularly preferred betamimetics are selected from among fenoterol, formoterol, salmeterol, 3-(4-{6-[2-hydroxy-2-(4-hydroxy-3-hydroxymethylphenyl)ethylamino]hexyloxy}butyl)benzenesulfonamide, 5-[2-(5,6-diethylindan-2-ylamino)-1-hydroxyethyl]-8-hydroxy-1H-quinoline-2-one, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 6-hydroxy-8-{1-hydroxy-2-[2-(4-methoxyphenyl)-1,1-dimethylethylamino]ethyl}-4H-benzo[1,4]oxazin-3-one, 6-hydroxy-8-{1-hydroxy-2-[2-(ethyl 4-phenoxyacetate)-1,1-dimethylethylamino]ethyl}-4H-benzo[1,4]oxazin-3-one, 6-hydroxy-8-{1-hydroxy-2-[2-(4-phenoxyacetic acid)-1,1-dimethylethylamino]ethyl}-4H-benzo[1,4]oxazin-3-one, 8-{2-[1,1-dimethyl-2-(2,4,6-trimethylphenyl)ethylamino]-1-hydroxyethyl}-6-hydroxy-4H-benzo[1,4]oxazin-3-one, 6-hydroxy-8-{1-hydroxy-2-[2-(4-hydroxyphenyl)-1,1-dimethylethylamino]ethyl}-4H-benzo[1,4]oxazin-3-one, 6-hydroxy-8-{1-hydroxy-2-[2-(4-isopropylphenyl)-1,1-dimethylethylamino]ethyl}-4H-benzo[1,4]oxazin-3-one, 8-{2-[2-(4-ethylphenyl)-1,1-dimethylethylamino]-1-hydroxyethyl}-6-hydroxy-4H-benzo[1,4]oxazin-3-one, 8-{2-[2-(4-ethoxyphenyl)-1,1-dimethylethylamino]-1-hydroxyethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)ethylamino]-2-methylpropyl}phenoxy)butyric acid, 8-{2-[2-(3,4-difluorophenyl)-1,1-dimethylethylamino]-1-hydroxyethyl}-6-hydroxy-4H-benzo[1,4]oxazin-3-one, and 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, enantiomers, diastereomers, and optionally in the form of the pharmacologically acceptable acid addition salts, solvates, or hydrates thereof.

Of these betamimetics the particularly preferred ones according to the invention are formoterol, salmeterol, 3-(4-{6-[2-hydroxy-2-(4-hydroxy-3-hydroxymethylphenyl)ethylamino]hexyloxy}butyl)benzenesulfonamide, 6-hydroxy-8-{1-hydroxy-2-[2-(4-methoxyphenyl)-1,1-dimethylethylamino]ethyl}-4H-benzo[1,4]oxazin-3-one, 6-hydroxy-8-{1-hydroxy-2-[2-(ethyl 4-phenoxyacetate)-1,1-dimethylethylamino]ethyl}-4H-benzo[1,4]oxazin-3-one, 6-hydroxy-8-{1-hydroxy-2-[2-(4-phenoxyacetic acid)-1,1-dimethylethylamino]ethyl}-4H-benzo[1,4]oxazin-3-one, 8-{2-[1,1-dimethyl-2-(2,4,6-trimethylphenyl)ethylamino]-1-hydroxyethyl}-6-hydroxy-4H-benzo[1,4]oxazin-3-one, 6-hydroxy-8-{1-hydroxy-2-[2-(4-hydroxyphenyl)-1,1-dimethylethylamino]ethyl}-4H-benzo[1,4]oxazin-3-one, 6-hydroxy-8-{1-hydroxy-2-[2-(4-isopropylphenyl)-1,1-dimethylethylamino]ethyl}-4H-benzo[1,4]oxazin-3-one, 8-{2-[2-(4-ethylphenyl)-1,1-dimethylethylamino]-1-hydroxyethyl}-6-hydroxy-4H-benzo[1,4]oxazin-3-one, 8-{2-[2-(4-ethoxyphenyl)-1,1-dimethylethylamino]-1-hydroxyethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)ethylamino]-2-methylpropyl}phenoxy)butyric acid, 8-{2-[2-(3,4-difluorophenyl)-1,1-dimethylethylamino]-1-hydroxyethyl}-6-hydroxy-4H-benzo[1,4]oxazin-3-one, and 5-[2-(5,6-diethylindan-2-ylamino)-1-hydroxyethyl]-8-hydroxy-1H-quinoline-2-one, optionally in the form of the racemates, enantiomers, diastereomers, and optionally in the form of the pharmacologically acceptable acid addition salts, solvates, or hydrates thereof.

According to the invention the acid addition salts of the betamimetics are preferably selected from among the hydrochloride, hydrobromide, hydroiodide, hydrosulfate, hydrophosphate, hydromethanesulfonate, hydronitrate, hydromaleate, hydroacetate, hydrocitrate, hydrofumarate, hydrotartrate, hydroxalate, hydrosuccinate, hydrobenzoate, and hydro-p-toluenesulfonate, preferably the hydrochloride, hydrobromide, hydrosulfate, hydrophosphate, hydrofumarate, and hydromethanesulfonate. Of the abovementioned acid addition salts the salts of hydrochloric acid, methanesulfonic acid, benzoic acid, and acetic acid are particularly preferred according to the invention.

The anticholinergics used are preferably compounds selected from among the tiotropium salts, oxitropium salts, flutropium salts, ipratropium salts, glycopyrronium salts, trospium salts, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxyfluorene-9-carboxylate methobromide, tropenol 9-fluorofluorene-9-carboxylate methobromide, scopine 9-hydroxyfluorene-9-carboxylate methobromide, scopine 9-fluorofluorene-9-carboxylate methobromide, tropenol 9-methylfluorene-9-carboxylate methobromide, scopine 9-methylfluorene-9-carboxylate methobromide, cyclopropyltropine benzilate methobromide, cyclopropyltropine 2,2-diphenylpropionate methobromide, cyclopropyltropine 9-hydroxyxanthene-9-carboxylate methobromide, cyclopropyltropine 9-methylfluorene-9-carboxylate methobromide, cyclopropyltropine 9-methylxanthene-9-carboxylate methobromide, cyclopropyltropine 9-hydroxyfluorene-9-carboxylate methobromide, methylcyclopropyltropine 4,4'-difluorobenzilate methobromide, tropenol 9-hydroxyxanthene-9-carboxylate methobromide, scopine 9-hydroxyxanthene-9-carboxylate methobromide, tropenol 9-methylxanthene-9-carboxylate methobromide, scopine 9-methylxanthene-9-carboxylate methobromide, tropenol 9-ethylxanthene-9-carboxylate methobromide, tropenol 9-difluoromethylxanthene-9-carboxylate methobromide, scopine 9-hydroxymethylxanthene-9-carboxylate methobromide, optionally in the form of the solvates, or hydrates thereof.

In the abovementioned salts the cations tiotropium, oxitropium, flutropium, ipratropium, glycopyrronium, and trospium are the pharmacologically active ingredients. As anions, the abovementioned salts may preferably contain chloride, bromide, iodide, sulfate, phosphate, methanesulfonate, nitrate, maleate, acetate, citrate, fumarate, tartrate, oxalate, succinate, benzoate, or p-toluenesulfonate, while chloride, bromide, iodide, sulfate, methanesulfonate, or p-toluenesulfonate are preferred as counter-ions. Of all the salts, the chlorides, bromides, iodides, and methanesulfonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among prednisolone, prednisone, butixocortpropionate, flunisolide, beclomethasone, triamcinolone, budesonide, fluticasone, mometasone, ciclesonide, rofleponide, dexamethasone, betamethasone, deflazacort, RPR-106541, NS-126, (S)-fluoromethyl 6,9-difluoro-17-[(2-furanylcarbonyl)oxy]-11-hydroxy-16-methyl-3-oxoandrosta-1,4-diene-17-carbothionate, and (S)-(2-oxotetrahydrofuran-3S-yl) 6,9-difluoro-11-hydroxy-16-methyl-3-oxo-17-propionyloxyandrosta-1,4-diene-17-carbothionate, optionally in the form of the racemates, enantiomers, or diastereomers thereof, and optionally in the form of the salts and derivatives, solvates, and/or hydrates thereof.

Particularly preferred is the steroid selected from among flunisolide, beclomethasone, triamcinolone, budesonide, fluticasone, mometasone, ciclesonide, rofleponide, dexamethasone, NS-126, (S)-fluoromethyl 6,9-difluoro-17-[(2-furanylcarbonyl)oxy]-11-hydroxy-16-methyl-3-oxoandrosta-1,4-diene-17-carbothionate, and (S)-(2-oxotetrahydrofuran-3S-yl) 6,9-difluoro-11-hydroxy-16-methyl-3-oxo-17-propionyloxyandrosta-1,4-diene-17-carbothionate, optionally in the form of the racemates, enantiomers, or diastereomers thereof, and optionally in the form of the salts and derivatives, solvates, and/or hydrates thereof.

Particularly preferred is the steroid selected from among budesonide, fluticasone, mometasone, ciclesonide, and (S)-fluoromethyl 6,9-difluoro-17-[(2-furanylcarbonyl)oxy]-11-hydroxy-16-methyl-3-oxoandrosta-1,4-diene-17-carbothionate, optionally in the form of the racemates, enantiomers, or diastereomers thereof, and optionally in the form of the salts and derivatives, solvates, and/or hydrates thereof.

Any reference to steroids includes a reference to any salts or derivatives, hydrates, or solvates thereof which may exist. Examples of possible salts and derivatives of the steroids may be: alkali metal salts, such as, for example, sodium or potassium salts, sulfobenzoates, phosphates, isonicotinates, acetates, propionates, dihydrogen phosphates, palmitates, pivalates, or furoates thereof.

Other PDE4 inhibitors which may be used are preferably compounds selected from among enprofyllin, theophyllin, roflumilast, ariflo (cilomilast), tofimilast, pumafentrin, lirimilast, arofyllin, atizoram, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370, N-(3,5-dichloro-1-oxop yridin-4-yl)-4-difluoromethoxy-3-cyclopropylmethoxybenzamide, (−)-p-[(4aR*,10bS*)-9-ethoxy-1,2,3,4,4a,10b-hexahydro-8-methoxy-2-methylbenzo[s][1,6] naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methylisothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexane-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl [4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-tri azolo[4,3-a]pyridine, and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers, or diastereomers, and optionally in the form of the pharmacologically acceptable acid addition salts, solvates, and/or hydrates thereof.

Particularly preferably the PDE4-inhibitor is selected from among enprofyllin, roflumilast, ariflo (cilomilast), arofyllin, atizoram, AWD-12-281 (GW-842470), T-440, T-2585, PD-168787, V-11294A, Cl-1018, CDC-801, D-22888, YM-58997, Z-15370, N-(3,5-dichloro-1-oxopyridin-4-yl)-4-difluoromethoxy-3-cyclopropylmethoxybenzamide, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl) cyclohexan-1-one, cis[4-cyano-4-(3-cyclopropylmethoxy-4-difluoromethoxyphenyl)cyclohexan-1-ol], 9-cyclopentyl-5,6-dihydro-7-ethyl-3-(2-thienyl)-9H-pyrazolo[3,4-c]-1,2,4-triazolo[4,3-a]pyridine, and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers, or diastereomers, and optionally in the form of the pharmacologically acceptable acid addition salts, solvates, and/or hydrates thereof.

Particularly preferably the PDE4-inhibitor is selected from among roflumilast, ariflo (cilomilast), arofyllin, AWD-12-281 (GW-842470), 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], atizoram, Z-15370, 9-cyclopentyl-5,6-dihydro-7-ethyl-3-(2-thienyl)-9H-pyrazolo[3,4-c]-1,2,4-triazolo[4,3-a]pyridine, and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers, or diastereomers, and optionally in the form of the pharmacologically acceptable acid addition salts, solvates, and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulfate, hydrophosphate, hydromethanesulfonate, hydronitrate, hydromaleate, hydroacetate, hydrobenzoate, hydrocitrate, hydrofumarate, hydrotartrate, hydroxalate, hydrosuccinate, hydrobenzoate, and hydro-p-toluenesulfonate, preferably hydrochloride, hydrobromide, hydrosulfate, hydrophosphate, hydrofumarate, and hydromethanesulfonate.

LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321, 1-(((R)-(3-(2-(6,7-difluoro-2-quinolinyl)ethenyl)phenyl)-3-(2-(2-hydroxy-2-propyl)phenyl)thio)methylcyclopropane acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropane acetic acid, and [2-[[2-(4-tert-butyl-2-thiazolyl)-5-benzofuranyl]oxymethyl]phenyl]acetic acid, optionally in the form of the racemates, enantiomers, or diastereomers, optionally in the form of the pharmacologically acceptable acid addition salts, and optionally in the form of the salts and derivatives, solvates, and/or hydrates thereof.

Preferably the LTD4-antagonist is selected from among montelukast, pranlukast, zafirlukast, MCC-847 (ZD-3523), MN-001, MEN-91507 (LM-1507), VUF-5078, VUF-K-8707, and L-733321, optionally in the form of the racemates, enantiomers, or diastereomers, optionally in the form of the pharmacologically acceptable acid addition salts, and optionally in the form of the salts and derivatives, solvates, and/or hydrates thereof.

Particularly preferably the LTD4-antagonist is selected from among montelukast, pranlukast, zafirlukast, MCC-847 (ZD-3523), MN-001, and MEN-91507 (LM-1507), optionally in the form of the racemates, enantiomers, or diastereomers, optionally in the form of the pharmacologically acceptable acid addition salts, and optionally in the form of the salts and derivatives, solvates, and/or hydrates thereof.

By acid addition salts with pharmacologically acceptable acids which the LTD4-antagonists may be capable of forming are meant, for example, salts selected from among the zo hydrochloride, hydrobromide, hydroiodide, hydro sulfate, hydrophosphate, hydromethanesulfonate, hydronitrate, hydromaleate, hydroacetate, hydrobenzoate, hydrocitrate, hydrofumarate, hydrotartrate, hydroxalate, hydrosuccinate, hydrobenzoate, and hydro-p-toluenesulfonate, preferably hydrochloride, hydrobromide, hydrosulfate, hydrophosphate, hydrofumarate, and hydromethanesulfonate. By salts or derivatives which the LTD4-antagonists may be capable of forming are meant, for example: alkali metal salts, such as, for example, sodium or potassium salts, alkaline earth metal salts, sulfobenzoates, phosphates, isonicotinates, acetates, propionates, dihydrogen phosphates, palmitates, pivalates, or furoates.

The EGFR-inhibitors used are preferably compounds selected from among 4-[(3-chloro-4-fluorophenyl)amino]-6-{[4-(morpholin-4-yl)-1-oxo-2-buten-1-yl]amino}-7-cyclopropylmethoxyquinazoline, 4-[(3-chloro-4-fluorophenyl)amino]-6-{[4-(N,N-diethylamino)-1-oxo-2-buten-1-yl]amino}-7-cyclopropylmethoxyquinazoline, 4-[(3-chloro-4-fluorophenyl)amino]-6-{[4-(N,N-dimethylamino)-1-oxo-2-buten-1-yl]amino}-7-cyclopropylmethoxyquinazoline, 4-[(R)-(1-phenylethyl)amino]-6-{[4-(morpholin-4-yl)-1-oxo-2-buten-1-yl]amino}-7-cyclopentyloxyquinazoline, 4-[(3-chloro-4-fluorophenyl)amino]-6-{[4-((R)-6-methyl-2-oxomorpholin-4-yl)-1-oxo-2-buten-1-yl]amino}-7-cyclopropylmethoxyquinazoline, 4-[(3-chloro-4-fluorophenyl)amino]-6-{[4-((R)-6-methyl-2-oxomorpholin-4-yl)-1-oxo-2-buten-1-yl]amino}-7-[(S)-(tetrahydrofuran-3-yl)oxy]quinazoline, 4-[(3-chloro-4-fluorophenyl)amino]-6-{[4-((R)-2-methoxymethyl-6-oxomorpholin-4-yl)-1-oxo-2-buten-1-yl]amino}-7-cyclopropylmethoxyquinazoline, 4-[(3-chloro-4-fluorophenyl)amino]-6-[2-((S)-6-methyl-2-oxomorpholin-4-yl)ethoxy]-7-methoxyquinazoline, 4-[(3-chloro-4-fluorophenyl)amino]-6-({4-[N-(2-methoxyethyl)-N-methylamino]-1-oxo-2-buten-1-yl}amino)-7-cyclopropylmethoxyquinazoline, 4-[(3-chloro-4-fluorophenyl)amino]-6-{[4-(N,N-dimethylamino)-1-oxo-2-buten-1-yl]amino}-7-cyclopentyloxyquinazoline, 4-[(R)-(1-phenylethyl)amino]-6-{[4-(N,N-bis-(2-methoxyethyl)amino)-1-oxo-2-buten-1-yl]amino}-7-cyclopropylmethoxyquinazoline, 4-[(R)-(1-phenylethyl)amino]-6-({4-[N-(2-methoxyethyl)-N-methylamino]-1-oxo-2-buten-1-yl}amino)-7-cyclopropylmethoxyquinazoline, 4-[(R)-(1-phenylethyl)amino]-6-({4-[N-(2-methoxyethyl)-N-methylamino]-1-oxo-2-buten-1-yl}amino)-7-cyclopropylmethoxyquinazoline, 4-[(R)-(1-phenylethyl)amino]-6-({4-[N-(tetrahydropyran-4-yl)-N-methylamino]-1-oxo-2-buten-1-yl}amino)-7-cyclopropylmethoxyquinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)quinazoline, 4-[(3-chloro-4-fluorophenyl)amino]-6-({4-[N-(2-methoxyethyl)-N-methylamino]-1-oxo-2-buten-1-yl}amino)-7-cyclopentyloxyquinazoline, 4-[(3-chloro-4-fluorophenyl)amino]-6-{[4-(N-cyclopropyl-N-methylamino)-1-oxo-2-buten-1-yl]amino}-7-cyclopentyloxyquinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]quinazoline, 4-[(3-ethynylphenyl)amino]-6,7-bis-(2-methoxyethoxy)quinazoline, 4-[(3-chloro-4-fluorophenyl)amino]-7-[3-(morpholin-4-yl)propyloxy]-6-[(vinylcarbonyl)amino]quinazoline, 4-[(R)-(1-phenylethyl)amino]-6-(4-hydroxyphenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxyquinoline, 4-{[3-chloro-4-(3-fluorobenzyloxy)phenyl]amino}-6-(5-{[(2-methanesulfonylethyl)amino]methyl}furan-2-yl)quinazoline, 4-[(R)-(1-phenylethyl)amino]-6-{[4-((R)-6-methyl-2-oxomorpholin-4-yl)-1-oxo-2-buten-1-yl]amino}-7-methoxyquinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]quinazoline, 4-[(3-chloro-4-fluorophenyl)amino]-6-({4-[N,N-bis-(2-methoxyethyl)amino]-1-oxo-2-buten-1-yl}amino)-7-[(tetrahydrofuran-2-yl)methoxy]quinazoline, 4-[(3-ethynylphenyl)amino]-6-{[4-(5,5-dimethyl-2-oxomorpholin-4-yl)-1-oxo-2-buten-1-yl]amino}quinazoline, 4-[(3-chloro-4-fluorophenyl)amino]-6-[2-(2,2-dimethyl-6-oxomorpholin-4-yl)ethoxy]-7-methoxyquinazoline, 4-[(3-chloro-4-fluorophenyl)amino]-6-[2-(2,2-dimethyl-6-oxomorpholin-4-yl)ethoxy]-7-[(R)-(tetrahydrofuran-2-yl)methoxy]quinazoline, 4-[(3-chloro-4-fluorophenyl)amino]-7-[2-(2,2-dimethyl-6-oxomorpholin-4-yl)ethoxy]-6-[(S)-(tetrahydrofuran-2-yl)methoxy]quinazoline, 4-[(3-chloro-4-fluorophenyl)amino]-6-{2-[4-(2-oxomorpholin-4-yl)piperidin-1-yl]ethoxy}-7-methoxyquinazoline, 4-[(3-chloro-4-fluorophenyl)amino]-6-[1-(tert-butyloxycarbonyl)piperidin-4-yloxy]-7-methoxyquinazoline, 4-[(3-chloro-4-fluorophenyl)amino]-6-(trans-4-aminocyclohexan-1-yloxy)-7-methoxyquinazoline, 4-[(3-chloro-4-fluorophenyl)amino]-6-(trans-4-methanesulfonylaminocyclohexan-1-yloxy)-7-methoxyquinazoline, 4-[(3-chloro-4-fluorophenyl)amino]-6-(tetrahydropyran-3-yloxy)-7-methoxyquinazoline, 4-[(3-chloro-4-fluorophenyl)amino]-6-(1-methylpiperidin-4-yloxy)-7-methoxyquinazoline, 4-[(3-chloro-4-fluorophenyl)

amino]-6-{1-[(morpholin-4-yl)carbonyl]piperidin-4-yloxy}-7-methoxyquinazoline, 4-[(3-chloro-4-fluorophenyl)amino]-6-{1-[(methoxymethyl)carbonyl]piperidin-4-yloxy}-7-methoxyquinazoline, 4-[(3-chloro-4-fluorophenyl)amino]-6-(piperidin-3-yloxy)-7-methoxyquinazoline, 4-[(3-chloro-4-fluorophenyl)amino]-6-[1-(2-acetylaminoethyl)piperidin-4-yloxy]-7-methoxyquinazoline, 4-[(3-chloro-4-fluorophenyl)amino]-6-(tetrahydropyran-4-yloxy)-7-ethoxyquinazoline, 4-[(3-chloro-4-fluorophenyl)amino]-6-((S)-tetrahydrofuran-3-yloxy)-7-hydroxyquinazoline, 4-[(3-chloro-4-fluorophenyl)amino]-6-(tetrahydropyran-4-yloxy)-7-(2-methoxyethoxy)quinazoline, 4-[(3-chloro-4-fluorophenyl)amino]-6-{trans-4-[(dimethylamino)sulfonylamino]cyclohexan-1-yloxy}-7-methoxyquinazoline, 4-[(3-chloro-4-fluorophenyl)amino]-6-{trans-4-[(morpholin-4-yl)carbonylamino]cyclohexan-1-yloxy}-7-methoxyquinazoline, 4-[(3-chloro-4-fluorophenyl)amino]-6-{trans-4-[(morpholin-4-yl)sulfonylamino]cyclohexan-1-yloxy}-7-methoxyquinazoline, 4-[(3-chloro-4-fluorophenyl)amino]-6-(tetrahydropyran-4-yloxy)-7-(2-acetylaminoethoxy)quinazoline, 4-[(3-chloro-4-fluorophenyl)amino]-6-(tetrahydropyran-4-yloxy)-7-(2-methanesulfonylaminoethoxy)quinazoline, 4-[(3-chloro-4-fluorophenyl)amino]-6-{1-[(piperidin-1-yl)carbonyl]piperidin-4-yloxy}-7-methoxyquinazoline, 4-[(3-chloro-4-fluorophenyl)amino]-6-(1-aminocarbonylmethylpiperidin-4-yloxy)-7-methoxyquinazoline, 4-[(3-chloro-4-fluorophenyl)amino]-6-(cis-4-{N-[(tetrahydropyran-4-yl)carbonyl]-N-methylamino}cyclohexan-1-yloxy)-7-methoxyquinazoline, 4-[(3-chloro-4-fluorophenyl)amino]-6-(cis-4-{N-[(morpholin-4-yl)carbonyl]-N-methylamino}cyclohexan-1-yloxy)-7-methoxyquinazoline, 4-[(3-chloro-4-fluorophenyl)amino]-6-(cis-4-{N-[(morpholin-4-yl)sulfonyl]-N-methylamino}cyclohexan-1-yloxy)-7-methoxy-quinazoline, 4-[(3-chloro-4-fluorophenyl)amino]-6-(trans-4-ethansulfonylaminocyclohexan-1-yloxy)-7-methoxyquinazoline, 4-[(3-chloro-4-fluorophenyl)amino]-6-(1-methanesulfonylpiperidin-4-yloxy)-7-ethoxyquinazoline, 4-[(3-chloro-4-fluorophenyl)amino]-6-(1-methanesulfonylpiperidin-4-yloxy)-7-(2-methoxyethoxy)quinazoline, 4-[(3-chloro-4-fluorophenyl)amino]-6-[1-(2-methoxyacetyl)piperidin-4-yloxy]-7-(2-methoxyethoxy)quinazoline, 4-[(3-chloro-4-fluorophenyl)amino]-6-(cis-4-acetylaminocyclohexan-1-yloxy)-7-methoxyquinazoline, 4-[(3-ethynylphenyl)amino]-6-[1-(tert-butyloxycarbonyl)piperidin-4-yloxy]-7-methoxyquinazoline, 4-[(3-ethynylphenyl)amino]-6-(tetrahydropyran-4-yloxy)-7-methoxyquinazoline, 4-[(3-chloro-4-fluorophenyl)amino]-6-(cis-4-{N-[(piperidin-1-yl)carbonyl]-N-methylamino}cyclohexan-1-yloxy)-7-methoxyquinazoline, 4-[(3-chloro-4-fluorophenyl)amino]-6-(cis-4-{N-[(4-methylpiperazin-1-yl)carbonyl]-N-methylamino}cyclohexan-1-yloxy)-7-methoxyquinazoline, 4-[(3-chloro-4-fluorophenyl)amino]-6-{cis-4-[(morpholin-4-yl)carbonylamino]cyclohexan-1-yloxy}-7-methoxyquinazoline, 4-[(3-chloro-4-fluorophenyl)amino]-6-{1-[2-(2-oxopyrrolidin-1-yl)ethyl]piperidin-4-yloxy}-7-methoxyquinazoline, 4-[(3-chloro-4-fluorophenyl)amino]-6-{1-[(morpholin-4-yl)carbonyl]piperidin-4-yloxy}-7-(2-methoxyethoxy)quinazoline, 4-[(3-ethynylphenyl)amino]-6-(1-acetylpiperidin-4-yloxy)-7-methoxyquinazoline, 4-[(3-ethynylphenyl)amino]-6-(1-methylpiperidin-4-yloxy)-7-methoxyquinazoline, 4-[(3-ethynylphenyl)amino]-6-(1-methanesulfonylpiperidin-4-yloxy)-7-methoxyquinazoline, 4-[(3-chloro-4-fluorophenyl)amino]-6-(1-methylpiperidin-4-yloxy)-7(2-methoxyethoxy)quinazoline, 4-[(3-chloro-4-fluorophenyl)amino]-6-(1-isopropyloxycarbonylpiperidin-4-yloxy)-7-methoxyquinazoline, 4-[(3-chloro-4-fluorophenyl)amino]-6-(cis-4-methylaminocyclohexan-1-yloxy)-7-methoxyquinazoline, 4-[(3-chloro-4-fluorophenyl)amino]-6-{cis-4-[N-(2-methoxy acetyl)-N-methylamino]cyclohexan-1-yloxy}-7-methoxyquinazoline, 4-[(3-ethynylphenyl)amino]-6-(piperidin-4-yloxy)-7-methoxyquinazoline, 4-[(3-ethynylphenyl)amino]-6-[1-(2-methoxyacetyl)piperidin-4-yloxy]-7-methoxyquinazoline, 4-[(3-s ethynylphenyl)amino]-6-{1-[(morpholin-4-yl)carbonyl]piperidin-4-yloxy}-7-methoxyquinazoline, 4-[(3-chloro-4-fluorophenyl)amino]-6-{1-[(cis-2,6-dimethylmorpholin-4-yl)carbonyl]piperidin-4-yloxy}-7-methoxyquinazoline, 4-[(3-chloro-4-fluorophenyl)amino]-6-{1-[(2-methylmorpholin-4-yl)carbonyl]piperidin-4-yloxy}-7-methoxyquinazoline, 4-[(3-chloro-4-fluorophenyl)amino]-6-{1-[(S,S)-(2-oxa-5-azabicyclo[2,2,1]hept-5-yl)carbonyl]piperidin-4-yloxy}-7-methoxyquinazoline, 4-[(3-chloro-4-fluorophenyl)amino]-6-{1-[(N-methyl-N-2-methoxyethylamino)carbonyl]piperidin-4-yloxy}-7-methoxyquinazoline, 4-[(3-chloro-4-fluorophenyl)amino]-6-(1-ethylpiperidin-4-yloxy)-7-methoxyquinazoline, 4-[(3-chloro-4-fluorophenyl)amino]-6-{1-[(2-methoxyethyl)carbonyl]piperidin-4-yloxy}-7-methoxyquinazoline, 4-[(3-chloro-4-fluorophenyl)amino]-6-{1-[(3-methoxypropylamino)carbonyl]piperidin-4-yloxy}-7-methoxyquinazoline, 4-[(3-chloro-4-fluorophenyl)amino]-6-[cis-4-(N-methanesulfonyl-N-methylamino)cyclohexan-1-yloxy]-7-methoxyquinazoline, 4-[(3-chloro-4-fluorophenyl)amino]-6-[cis-4-(N-acetyl-N-methylamino)cyclohexan-1-yloxy]-7-methoxyquinazoline, 4-[(3-chloro-4-fluorophenyl)amino]-6-(trans-4-methylaminocyclohexan-1-yloxy)-7-methoxyquinazoline, 4-[(3-chloro-4-fluorophenyl)amino]-6-[trans-4-(N-methanesulfonyl-N-methylamino)cyclohexan-1-yloxy]-7-methoxyquinazoline, 4-[(3-chloro-4-fluorophenyl)amino]-6-(trans-4-dimethylaminocyclohexan-1-yloxy)-7-methoxyquinazoline, 4-[(3-chloro-4-fluorophenyl)amino]-6-(trans-4-{N-[(morpholin-4-yl)carbonyl]-N-methylamino}cyclohexan-1-yloxy)-7-methoxyquinazoline, 4-[(3-chloro-4-fluorophenyl)amino]-6-[2-(2,2-dimethyl-6-oxomorpholin-4-yl)ethoxy]-7-[(S)-(tetrahydrofuran-2-yl)methoxy]quinazoline, 4-[(3-chloro-4-fluorophenyl)amino]-6-(1-methanesulfonylpiperidin-4-yloxy)-7-methoxyquinazoline, 4-[(3-chloro-4-fluorophenyl)amino]-6-(1-cyanopiperidin-4-yloxy)-7-methoxyquinazoline, cetuximab, trastuzumab, ABX-EGF, and Mab ICR-62, optionally in the form of the racemates, enantiomers, or diastereomers thereof, optionally in the form of the pharmacologically acceptable acid addition salts thereof, the solvates, and/or hydrates thereof.

Preferred EGFR-inhibitors are selected from among 4-[(3-chloro-4-fluorophenyl)amino]-6-{4-(morpholin-4-yl)-1-oxo-2-buten-1-yl]amino}-7-cyclopropylmethoxyquinazoline, 4-[(3-chloro-4-fluorophenyl)amino]-6-{[4-(N,N-diethylamino)-1-oxo-2-buten-1-yl]amino}-7-cyclopropylmethoxyquinazoline, 4-[(3-chloro-4-fluorophenyl)amino]-6-{[4-(N,N-dimethylamino)-1-oxo-2-buten-1-yl]amino}-7-cyclopropylmethoxyquinazoline, 4-[(R)-(1-phenylethyl)amino]-6-{[4-(morpholin-4-yl)-1-oxo-2-buten-1-yl]amino}-7-cyclopentyloxyquinazoline, 4-[(3-chloro-4-fluorophenyl)amino]-6-{[4-((R)-6-methyl-2-oxomorpholin-4-yl)-1-oxo-2-buten-1-yl]amino}-7-cyclopropylmethoxyquinazoline, 4-[(3-chloro-4-fluorophenyl)amino]-6-{[4-((R)-6-methyl-2-oxomorpholin-4-yl)-1-oxo-2-buten-1-yl]amino}-7-[(S)-(tetrahydrofuran-3-yl)oxy]quinazoline, 4-[(3-chloro-4-fluorophenyl)amino]-6-{[4-

((R)-2-methoxymethyl-6-oxomorpholin-4-yl)-1-oxo-2-buten-1-yl]amino}-7-cyclopropylmethoxyquinazoline, 4-[(3-chloro-4-fluorophenyl)amino]-6-[2-((S)-6-methyl-2-oxomorpholin-4-yl)ethoxy]-7-methoxyquinazoline, 4-[(3-chloro-4-fluorophenyl)amino]-6-({4-[N-(2-methoxyethyl)-N-methylamino]-1-oxo-2-buten-1-yl}amino)-7-cyclopropylmethoxyquinazoline, 4-[(3-chloro-4-fluorophenyl)amino]-6-{[4-(N,N-dimethylamino)-1-oxo-2-buten-1-yl]amino}-7-cyclopentyloxyquinazoline, 4-[(R)-(1-phenylethyl)amino]-6-{[4-(N,N-bis-(2-methoxyethyl)amino)-1-oxo-2-buten-1-yl]amino}-7-cyclopropylmethoxyquinazoline, 4-[(R)-(1-phenylethyl)amino]-6-({4-[N-(2-methoxyethyl)-N-ethylamino]-1-oxo-2-buten-1-yl}amino)-7-cyclopropylmethoxyquinazoline, 4-[(R)-(1-phenylethyl)amino]-6-({4-[N-(2-methoxyethyl)-N-methylamino]-1-oxo-2-buten-1-yl}amino)-7-cyclopropylmethoxyquinazoline, 4-[(R)-(1-phenylethyl)amino]-6-({4-[N-(tetrahydropyran-4-yl)-N-methylamino]-1-oxo-2-buten-1-yl}amino)-7-cyclopropylmethoxyquinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)quinazoline, 4-[(3-chloro-4-fluorophenyl)amino]-6-({4-[N-(2-methoxyethyl)-N-methylamino]-1-oxo-2-buten-1-yl}amino)-7-cyclopentyloxyquinazoline, 4-[(3-chloro-4-fluorophenyl)amino]-6-{[4-(N-cyclopropyl-N-methylamino)-1-oxo-2-buten-1-yl]amino}-7-cyclopentyloxyquinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]quinazoline, 4-[(3-ethynylphenyl)amino]-6,7-bis-(2-methoxyethoxy)quinazoline, 4-[(3-chloro-4-fluorophenyl)amino]-7-[3-(morpholin-4-yl)propyloxy]-6-[(vinylcarbonyl)amino]quinazoline, 4-[(R)-(1-phenylethyl)amino]-6-(4-hydroxyphenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxyquinoline, 4-{[3-chloro-4-(3-fluorobenzyloxy)phenyl]amino}-6-(5-{[(2-methanesulfonylethyl)amino]methyl}furan-2-yl)quinazoline, 4-[(R)-(1-phenylethyl)amino]-6-{[4-((R)-6-methyl-2-oxomorpholin-4-yl)-1-oxo-2-buten-1-yl]amino}-7-methoxyquinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]quinazoline, 4-[(3-chloro-4-fluorophenyl)amino]-6-({4-[N,N-bis-(2-methoxyethyl)amino]-1-oxo-2-buten-1-yl}amino)-7-[(tetrahydrofuran-2-yl)methoxy]quinazoline, 4-[(3-ethynylphenyl)amino]-6-{[4-(5,5-dimethyl-2-oxomorpholin-4-yl)-1-oxo-2-buten-1-yl]amino}quinazoline, 4-[(3-chloro-4-fluorophenyl)amino]-6-[2-(2,2-dimethyl-6-oxomorpholin-4-yl)ethoxy]-7-methoxyquinazoline, 4-[(3-chloro-4-fluorophenyl)amino]-6-[2-(2,2-dimethyl-6-oxomorpholin-4-yl)ethoxy]-7-[(R)-(tetrahydrofuran-2-yl)methoxy]quinazoline, 4-[(3-chloro-4-fluorophenyl)amino]-7-[2-(2,2-dimethyl-6-oxomorpholin-4-yl)ethoxy]-6-[(S)-(tetrahydrofuran-2-yl)methoxy]quinazoline, 4-[(3-chloro-4-fluorophenyl)amino]-6-{2-[4-(2-oxomorpholin-4-yl)piperidin-1-yl]ethoxy}-7-methoxyquinazoline, 4-[(3-chloro-4-fluorophenyl)amino]-6-[1-(tert-butyloxycarbonyl)piperidin-4-yloxy]-7-methoxyquinazoline, 4-[(3-chloro-4-fluorophenyl)amino]-6-(trans-4-aminocyclohexan-1-yloxy)-7-methoxyquinazoline, 4-[(3-chloro-4-fluorophenyl)amino]-6-(trans-4-methanesulfonylaminocyclohexan-1-yloxy)-7-methoxyquinazoline, 4-[(3-chloro-4-fluorophenyl)amino]-6-(tetrahydropyran-3-yloxy)-7-methoxyquinazoline, 4-[(3-chloro-4-fluorophenyl)amino]-6-(1-methylpiperidin-4-yloxy)-7-methoxyquinazoline, 4-[(3-chloro-4-fluorophenyl)amino]-6-{1-[(morpholin-4-yl)carbonyl]piperidin-4-yloxy}-7-methoxyquinazoline, 4-[(3-chloro-4-fluorophenyl)amino]-6-{1-[(methoxymethyl)carbonyl]piperidin-4-yloxy}-7-methoxyquinazoline, 4-[(3-chloro-4-fluorophenyl)amino]-6-(piperidin-3-yloxy)-7-methoxyquinazoline, 4-[(3-chloro-4-fluorophenyl)amino]-6-[1-(2-acetylaminoethyl)piperidin-4-yloxy]-7-methoxyquinazoline, 4-[(3-chloro-4-fluorophenyl)amino]-6-(tetrahydropyran-4-yloxy)-7-ethoxyquinazoline, 4-[(3-chloro-4-fluorophenyl)amino]-6-((S)-tetrahydrofuran-3-yloxy)-7-hydroxyquinazoline, 4-[(3-chloro-4-fluorophenyl)amino]-6-(tetrahydropyran-4-yloxy)-7-(2-methoxyethoxy)quinazoline, 4-[(3-chloro-4-fluorophenyl)amino]-6-{trans-4-[(dimethylamino)sulfonylamino]cyclohexan-1-yloxy}-7-methoxyquinazoline, 4-[(3-chloro-4-fluorophenyl)amino]-6-{trans-4-[(morpholin-4-yl)carbonylamino]cyclohexan-1-yloxy}-7-methoxyquinazoline, 4-[(3-chloro-4-fluorophenyl)amino]-6-{trans-4-[(morpholin-4-yl)sulfonylamino]cyclohexan-1-yloxy}-7-methoxyquinazoline, 4-[(3-chloro-4-fluorophenyl)amino]-6-(tetrahydropyran-4-yloxy)-7-(2-acetylaminoethoxy)quinazoline, 4-[(3-chloro-4-fluorophenyl)amino]-6-(tetrahydropyran-4-yloxy)-7-(2-methanesulfonylaminoethoxy)quinazoline, 4-[(3-chloro-4-fluorophenyl)amino]-6-{1-[(piperidin-1-yl)carbonyl]piperidin-4-yloxy}-7-methoxyquinazoline, 4-[(3-chloro-4-fluorophenyl)amino]-6-(1-aminocarbonylmethylpiperidin-4-yloxy)-7-methoxyquinazoline, 4-[(3-chloro-4-fluorophenyl)amino]-6-(cis-4-{N-[(tetrahydropyran-4-yl)carbonyl]-N-methylamino}cyclohexan-1-yloxy)-7-methoxyquinazoline, 4-[(3-chloro-4-fluorophenyl)amino]-6-(cis-4-{N-[(morpholin-4-yl)carbonyl]-N-methylamino}cyclohexan-1-yloxy)-7-methoxyquinazoline, 4-[(3-chloro-4-fluorophenyl)amino]-6-(cis-4-{N-[(morpholin-4-yl)sulfonyl]-N-methylamino}cyclohexan-1-yloxy)-7-methoxyquinazoline, 4-[(3-chloro-4-fluorophenyl)amino]-6-(trans-4-ethansulfonylaminocyclohexan-1-yloxy)-7-methoxyquinazoline, 4-[(3-chloro-4-fluorophenyl)amino]-6-(1-methanesulfonylpiperidin-4-yloxy)-7-ethoxyquinazoline, 4-[(3-chloro-4-fluorophenyl)amino]-6-(1-methanesulfonylpiperidin-4-yloxy)-7-(2-methoxyethoxy)quinazoline, 4-[(3-chloro-4-fluorophenyl)amino]-6-[1-(2-methoxyacetyl)piperidin-4-yloxy]-7-(2-methoxyethoxy)quinazoline, 4-[(3-chloro-4-fluorophenyl)amino]-6-(cis-4-acetylaminocyclohexan-1-yloxy)-7-methoxyquinazoline, 4-[(3-ethynylphenyl)amino]-6-[1-(tert-butyloxycarbonyl)piperidin-4-yloxy]-7-methoxyquinazoline, 4-[(3-ethynylphenyl)amino]-6-(tetrahydropyran-4-yloxy]-7-methoxyquinazoline, 4-[(3-chloro-4-fluorophenyl)amino]-6-(cis-4-{N-[(piperidin-1-yl)carbonyl]-N-methylamino}cyclohexan-1-yloxy)-7-methoxyquinazoline, 4-[(3-chloro-4-fluorophenyl)amino]-6-(cis-4-{N-[(4-methylpiperazin-1-yl)carbonyl]-N-methylamino}cyclohexan-1-yloxy)-7-methoxyquinazoline, 4-[(3-chloro-4-fluorophenyl)amino]-6-{cis-4-[(morpholin-4-yl)carbonylamino]cyclohexan-1-yloxy}-7-methoxyquinazoline, 4-[(3-chloro-4-fluorophenyl)amino]-6-{1-[2-(2-oxopyrrolidin-1-yl)ethyl]piperidin-4-yloxy}-7-methoxyquinazoline, 4-[(3-chloro-4-fluorophenyl)amino]-6-{1-[(morpholin-4-yl)carbonyl]piperidin-4-yloxy}-7-(2-methoxyethoxy)quinazoline, 4-[(3-ethynylphenyl)amino]-6-(1-acetylpiperidin-4-yloxy)-7-methoxyquinazoline, 4-[(3- ethynylphenyl)amino]-6-(1-methylpiperidin-4-yloxy)-7-methoxyquinazoline, 4-[(3-ethynylphenyl)amino]-6-(1-methanesulfonylpiperidin-4-yloxy)-7-methoxyquinazoline, 4-[(3-chloro-4-fluorophenyl)amino]-6-(1-methylpiperidin-4-yloxy)-7 (2-methoxyethoxy)quinazoline, 4-[(3-chloro-4-fluorophenyl)amino]-6-(1-isopropyloxycarbonylpiperidin-4-yloxy)-7-methoxyquinazoline, 4-[(3-chloro-4-fluorophenyl)amino]-6-(cis-4-methylaminocyclohexan-1-yloxy)-7-methoxyquinazoline, 4-[(3-chloro-4-fluorophenyl)amino]-6-{cis-4-[N-(2-methoxyacetyl)-N-methylamino]cyclohexan-1-yloxy}-7-methoxyquinazoline, 4-[(3-ethynylphenyl)amino]-6-(piperidin-4-yloxy)-7-methoxyquinazoline, 4-[(3-ethynylphenyl)amino]-6-[1-(2-methoxyacetyl)piperidin-4-yloxy]-7-methoxyquinazoline, 4-[(3-ethynylphenyl)amino]-6-{1-[(morpholin-4-yl)carbonyl]piperidin-4-yloxy}-7-methoxyquinazoline, 4-[(3-chloro-4-fluorophenyl)amino]-6-{1-[(cis-2,6-dimethylmorpholin-4-yl)carbonyl]piperidin-4-yloxy}-7-methoxyquinazoline, 4-[(3-chloro-4-fluorophenyl)amino]-6-{1-[(2-methylmorpholin-4-yl)carbonyl]piperidin-4-yloxy}-7-methoxyquinazoline, 4-[(3-chloro-4-fluorophenyl)amino]-6-{1-[(S,S)-(2-oxa-5-azabicyclo[2,2,1]hept-5-yl)carbonyl]piperidin-4-yloxy}-7-methoxyquinazoline, 4-[(3-chloro-4-fluorophenyl)amino]-6-{1-[(N-methyl-N-2-methoxyethylamino)carbonyl]piperidin-4-yloxy}-7-methoxyquinazoline, 4-[(3-chloro-4-fluorophenyl)amino]-6-(1-ethylpiperidin-4-yloxy)-7-methoxyquinazoline, 4-[(3-chloro-4-fluorophenyl)amino]-6-{1-[(2-methoxyethyl)carbonyl]piperidin-4-yloxy}-7-methoxyquinazoline, 4-[(3-chloro-4-fluorophenyl)amino]-6-{1-[(3-methoxypropylamino)carbonyl]piperidin-4-yloxy}-7-methoxyquinazoline, 4-[(3-chloro-4-fluorophenyl)amino]-6-[cis-4-(N-methanesulfonyl-N-methylamino)cyclohexan-1-yloxy]-7-methoxyquinazoline, 4-[(3-chloro-4-fluorophenyl)amino]-6-[cis-4-(N-acetyl-N-methylamino)cyclohexan-1-yloxy]-7-methoxyquinazoline, 4-[(3-chloro-4-fluorophenyl)amino]-6-(trans-4-methylaminocyclohexan-1-yloxy)-7-methoxyquinazoline, 4-[(3-chloro-4-fluorophenyl)amino]-6-[trans-4-(N-methanesulfonyl-N-methylamino)cyclohexan-1-yloxy]-7-methoxyquinazoline, 4-[(3-chloro-4-fluorophenyl)amino]-6-(trans-4-dimethylaminocyclohexan-1-yloxy)-7-methoxyquinazoline, 4-[(3-chloro-4-fluorophenyl)amino]-6-(trans-4-{N-[(morpholin-4-yl)carbonyl]-N-methylamino}cyclohexan-1-yloxy)-7-methoxyquinazoline, 4-[(3-chloro-4-fluorophenyl)amino]-6-[2-(2,2-dimethyl-6-oxomorpholin-4-yl)ethoxy]-7-[(S)-(tetrahydrofuran-2-yl)methoxy]quinazoline, 4-[(3-chloro-4-fluorophenyl)amino]-6-(1-methanesulfonylpiperidin-4-yloxy)-7-methoxyquinazoline, 4-[(3-chloro-4-fluorophenyl)amino]-6-(1-cyanopiperidin-4-yloxy)-7-methoxyquinazoline, and cetuximab, optionally in the form of the racemates, enantiomers, or diastereomers thereof, optionally in the form of the pharmacologically acceptable acid addition salts thereof, the solvates, and/or hydrates thereof.

It is particularly preferable within the scope of the present invention to use those EGFR-inhibitors which are selected from among 4-[(3-chloro-4-fluorophenyl)amino]-6-{[4-(morpholin-4-yl)-1-oxo-2-buten-1-yl]amino}-7-cyclopropylmethoxyquinazoline, 4-[(R)-(1-phenylethyl)amino]-6-{[4-(morpholin-4-yl)-1-oxo-2-buten-1-yl]amino}-7-cyclopentyloxyquinazoline, 4-[(3-chloro-4-fluorophenyl)amino]-6-{[4-((R)-6-methyl-2-oxomorpholin-4-yl)-1-oxo-2-buten-1-yl]amino}-7-[(S)-(tetrahydrofuran-3-yl)oxy]quinazoline, 4-[(3-chloro-4-fluorophenyl)amino]-6-[2-((S)-6-methyl-2-oxomorpholin-4-yl)ethoxy]-7-methoxyquinazoline, 4-[(3-chloro-4-fluorophenyl)amino]-6-({4-[N-(2-methoxyethyl)-N-methylamino]-1-oxo-2-buten-1-yl}amino)-7-cyclopropylmethoxyquinazoline, 4-[(R)-(1-phenylethyl)amino]-6-({4-[N-(tetrahydropyran-4-yl)-N-methylamino]-1-oxo-2-buten-1-yl}amino)-7-cyclopropylmethoxyquinazoline, 4-[(3-chloro-4-fluorophenyl)amino]-6-({4-[N-(2-methoxyethyl)-N-methylamino]-1-oxo-2-buten-1-yl}amino)-7-cyclopentyloxyquinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]quinazoline, 4-[(3-ethynylphenyl)amino]-6,7-bis-(2-methoxyethoxy)quinazoline, 4-[(R)-(1-phenylethyl)amino]-6-(4-hydroxyphenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxyquinoline, 4-[(R)-(1-phenylethyl)amino]-6-{[4-((R)-6-methyl-2-oxomorpholin-4-yl)-1-oxo-2-buten-1-yl]amino}-7-methoxyquinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]quinazoline, 4-[(3-ethynylphenyl)amino]-6-{[4-(5,5-dimethyl-2-oxomorpholin-4-yl)-1-oxo-2-buten-1-yl]amino}quinazoline, 4-[(3-chloro-4-fluorophenyl)amino]-6-{2-[4-(2-oxomorpholin-4-yl)piperidin-1-yl]ethoxy}-7-methoxyquinazoline, 4-[(3-chloro-4-fluorophenyl)amino]-6-(trans-4-aminocyclohexan-1-yloxy)-7-methoxyquinazoline, 4-[(3-chloro-4-fluorophenyl)amino]-6-(trans-4-methane sulfonylaminocyclohexan-1-yloxy)-7-methoxyquinazoline, 4-[(3-chloro-4-fluorophenyl)amino]-6-(tetrahydropyran-3-yloxy)-7-methoxyquinazoline, 4-[(3-chloro-4-fluorophenyl)amino]-6-{1-[(morpholin-4-yl)carbonyl]piperidin-4-yloxy}-7-methoxyquinazoline, 4-[(3-chloro-4-fluorophenyl)amino]-6-(piperidin-3-yloxy)-7-methoxyquinazoline, 4-[(3-chloro-4-fluorophenyl)amino]-6-[1-(2-acetylaminoethyl)piperidin-4-yloxy]-7-methoxyquinazoline, 4-[(3-chloro-4-fluorophenyl)amino]-6-(tetrahydropyran-4-yloxy)-7-ethoxyquinazoline, 4-[(3-chloro-4-fluorophenyl)amino]-6-{trans-4-[(morpholin-4-yl)carbonylamino]cyclohexan-1-yloxy}-7-methoxyquinazoline, 4-[(3-chloro-4-fluorophenyl)amino]-6-{1-[(piperidin-1-yl)carbonyl]piperidin-4-yloxy}-7-methoxyquinazoline, 4-[(3-chloro-4-fluorophenyl)amino]-6-(cis-4-{N-[(morpholin-4-yl)carbonyl]-N-methylamino}cyclohexan-1-yloxy)-7-methoxyquinazoline, 4-[(3-chloro-4-fluorophenyl)amino]-6-(trans-4-ethansulfonylaminocyclohexan-1-yloxy)-7-methoxyquinazoline, 4-[(3-chloro-4-fluorophenyl)amino]-6-(1-methanesulfonylpiperidin-4-yloxy)-7-(2-methoxyethoxy)quinazoline, 4-[(3-chloro-4-fluorophenyl)amino]-6-[1-(2-methoxyacetyl)piperidin-4-yloxy]-7-(2-methoxyethoxy)quinazoline, 4-[(3-ethynylphenyl)amino]-6-(tetrahydropyran-4-yloxy)-7-methoxyquinazoline, 4-[(3-chloro-4-fluorophenyl)amino]-6-(cis-4-{N-[(piperidin-1-yl)carbonyl]-N-methylamino}cyclohexan-1-yloxy)-7-methoxyquinazoline, 4-[(3-chloro-4-fluorophenyl)amino]-6-{cis-4-[(morpholin-4-yl)carbonylamino]cyclohexan-1-yloxy}-7-methoxyquinazoline, 4-[(3-chloro-4-fluorophenyl)amino]-6-{1-[2-(2-oxopyrrolidin-1-yl)ethyl]piperidin-4-yloxy}-7-methoxyquinazoline, 4-[(3-ethynylphenyl)amino]-6-(1-acetylpiperidin-4-yloxy)-7-methoxyquinazoline, 4-[(3-ethynylphenyl)amino]-6-(1-methylpiperidin-4-yloxy)-7-methoxyquinazoline, 4-[(3-ethynylphenyl)amino]-6-(1-methanesulfonylpiperidin-4-yloxy)-7-methoxyquinazoline, 4-[(3-chloro-4-fluorophenyl)amino]-6-(1-methylpiperidin-4-yloxy)-7 (2-methoxyethoxy)quinazoline, 4-[(3-ethynylphenyl)amino]-6-{1-[(morpholin-4-yl)carbonyl]piperidin-4-yloxy}-7-methoxyquinazoline, 4-[(3-chloro-4-fluorophenyl)amino]-6-{1-[(N-methyl-N-2- methoxyethylamino)carbonyl]piperidin-4-yloxy}-7-methoxyquinazoline, 4-[(3-chloro-4-fluorophenyl)amino]-6-(1-ethylpiperidin-4-yloxy)-7-methoxyquinazoline, 4-[(3-chloro-4-fluorophenyl)amino]-6-[cis-4-(N-methanesulfonyl-N-methylamino)cyclohexan-1-yloxy]-7-methoxyquinazoline, 4-[(3-chloro-4-fluorophenyl)amino]-6-[cis-4-(N-acetyl-N-methylamino)cyclohexan-1-yloxy]-7-methoxyquinazoline, 4-[(3-chloro-4-fluorophenyl)amino]-6-(trans-4-methylaminocyclohexan-1-yloxy)-7-methoxyquinazoline, 4-[(3-chloro-4-fluorophenyl)amino]-6-[trans-4-(N-methanesulfonyl-N-methylamino)cyclohexan-1-yloxy]-7-methoxyquinazoline, 4-[(3-chloro-4-fluorophenyl)amino]-6-(trans-4-dimethylaminocyclohexan-1-yloxy)-7-methoxyquinazoline, 4-[(3-chloro-4-fluorophenyl)amino]-6-(trans-4-{N-[(morpholin-4-yl)carbonyl]-N-methylamino}cyclohexan-1-yloxy)-7-methoxyquinazoline, 4-[(3-chloro-4-fluorophenyl)amino]-6-[2-(2,2-dimethyl-6-oxomorpholin-4-yl)ethoxy]-7-[(S)-(tetrahydrofuran-2-yl)methoxy]quinazoline, 4-[(3-chloro-4-fluorophenyl)amino]-6-(1-methanesulfonylpiperidin-4-yloxy)-7-methoxyquinazoline, 4-[(3-chloro-4-fluorophenyl)amino]-6-(1-cyanopiperidin-4-yloxy)-7-methoxyquinazoline, and 4-[(3-chloro-4-fluorophenyl)amino]-6-{1-[(2-methoxyethyl)carbonyl]piperidin-4-yloxy}-7-methoxyquinazoline, optionally in the form of the racemates, enantiomers, or diastereomers thereof, optionally in the form of the pharmacologically acceptable acid addition salts thereof, the solvates, and/or hydrates thereof.

Particularly preferred EGFR-inhibitors according to the invention are the compounds selected from among 4-[(3-chloro-4-fluorophenyl)amino]-6-{[4-(morpholin-4-yl)-1-oxo-2-buten-1-yl]-amino}-7-cyclopropylmethoxyquinazoline, 4-[(3-chloro-4-fluorophenyl)amino]-6-{[4-((R)-6-methyl-2-oxomorpholin-4-yl)-1-oxo-2-buten-1-yl]amino}-7-[(S)-(tetrahydrofuran-3-yl)oxy]quinazoline, 4-[(3-chloro-4-fluorophenyl)amino]-6-[2-((S)-6-methyl-2-oxomorpholin-4-yl)ethoxy]-7-methoxyquinazoline, 4-[(3-chloro-4-fluorophenyl)amino]-6-({4-[N-(2-methoxyethyl)-N-methylamino]-1-oxo-2-buten-1-yl}amino)-7-cyclopropylmethoxyquinazoline, 4-[(3-ethynylphenyl)amino]-6,7-bis-(2-methoxyethoxy)quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]quinazoline, 4-[(3-ethynylphenyl)amino]-6-{[4-(5,5-dimethyl-2-oxomorpholin-4-yl)-1-oxo-2-buten-1-yl]amino}quinazoline, 4-[(3-chloro-4-fluorophenyl)amino]-6-(trans-4-methanesulfonylaminocyclohexan-1-yloxy)-7-methoxyquinazoline, 4-[(3-chloro-4-fluorophenyl)amino]-6-(tetrahydropyran-3-yloxy)-7-methoxyquinazoline, 4-[(3-chloro-4-fluorophenyl)amino]-6-{1-[(morpholin-4-yl)carbonyl]piperidin-4-yloxy}-7-methoxyquinazoline, 4-[(3-chloro-4-fluorophenyl)amino]-6-{1-[2-(2-oxopyrrolidin-1-yl)ethyl]piperidin-4-yloxy}-7-methoxyquinazoline, 4-[(3-ethynylphenyl)amino]-6-(1-acetylpiperidin-4-yloxy)-7-methoxyquinazoline, 4-[(3-ethynylphenyl)amino]-6-(1-methylpiperidin-4-yloxy)-7-methoxyquinazoline, 4-[(3-ethynylphenyl)amino]-6-(1-methane sulfonylpiperidin-4-yloxy)-7-methoxyquinazoline, 4-[(3-ethynylphenyl)amino]-6-{1-[(morpholin-4-yl)carbonyl]piperidin-4-yloxy}-7-methoxyquinazoline, 4-[(3-chloro-4-fluorophenyl)amino]-6-{1-[(2-methoxyethyl)carbonyl]piperidin-4-yloxy}-7-methoxyquinazoline, 4-[(3-chloro-4-fluorophenyl)amino]-6-[cis-4-(N-methanesulfonyl-N-methylamino)cyclohexan-1-yloxy]-7-methoxyquinazoline, 4-[(3-chloro-4-fluorophenyl)amino]-6-[cis-4-(N-acetyl-N-methylamino)cyclohexan-1-yloxy]-7-methoxyquinazoline, 4-[(3-chloro-4-fluorophenyl)amino]-6-(trans-4-methylaminocyclohexan-1-yloxy)-7-methoxyquinazoline, 4-[(3-chloro-4-fluorophenyl)amino]-6-[trans-4-(N-methane sulfonyl-N-methylamino)cyclohexan-1-yloxy]-7-methoxyquinazoline, 4-[(3-chloro-4-fluorophenyl)amino]-6-(trans-4-dimethylaminocyclohexan-1-yloxy)-7-methoxyquinazoline, 4-[(3-chloro-4-fluorophenyl)amino]-6-(trans-4-{N-[(morpholin-4-yl)carbonyl]-N-methylamino}cyclohexan-1-yloxy)-7-methoxyquinazoline, 4-[(3-chloro-4-fluorophenyl)amino]-6-[2-(2,2-dimethyl-6-oxomorpholin-4-yl)ethoxy]-7-[(S)-(tetrahydrofuran-2-yl)methoxy]quinazoline, 4-[(3-chloro-4-fluorophenyl)amino]-6-(1-methane sulfonylpiperidin-4-yloxy)-7-methoxyquinazoline, and 4-[(3-chloro-4-fluorophenyl)amino]-6-(1-cyanopiperidin-4-yloxy)-7-methoxyquinazoline, optionally in the form of the racemates, enantiomers, or diastereomers thereof, optionally in the form of the pharmacologically acceptable acid addition salts thereof, the solvates, and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulfate, hydrophosphate, hydromethanesulfonate, hydronitrate, hydromaleate, hydroacetate, hydrobenzoate, hydrocitrate, hydrofumarate, hydrotartrate, hydroxalate, hydrosuccinate, hydrobenzoate, and hydro-p-toluenesulfonate, preferably hydrochloride, hydrobromide, hydrosulfate, hydrophosphate, hydrofumarate, and hydromethanesulfonate.

Examples of dopamine agonists which may be used preferably include compounds selected from among bromocriptine, cabergoline, alpha-dihydroergocryptine, lisuride, pergolide, pramipexole, roxindole, ropinirole, talipexole, terguride, and viozan. Any reference to the abovementioned dopamine agonists within the scope of the present invention includes a reference to any pharmacologically acceptable acid addition salts and optionally hydrates thereof which may exist. By the physiologically acceptable acid addition salts which may be formed by the abovementioned dopamine agonists are meant, for example, pharmaceutically acceptable salts which are selected from the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid.

Examples of H1-antihistamines preferably include compounds selected from among epinastine, cetirizine, azelastine, fexofenadine, levocabastine, loratadine, mizolastine, ketotifen, emedastine, dimethindene, clemastine, bamipine, dexchlorpheniramine, pheniramine, doxylamine, chlorphenoxamine, dimenhydrinate, diphenhydramine, promethazine, ebastine, desloratidine, and meclizine. Any reference to the above-mentioned H1-antihistamines within the scope of the present invention includes a reference to any pharmacologically acceptable acid addition salts which may exist.

Examples of PAF-antagonists preferably include compounds selected from 4-(2-chlorophenyl)-9-methyl-2-[3(4-morpholinyl)-3-propanon-1-yl]-6H-thieno-[3,2-f]-[1,2,4]triazolo[4,3-a][1,4]diazepines, and 6-(2-chlorophenyl)-8,9-dihydro-1-methyl-8-[(4-morpholinyl)carbonyl]-4H,7H-cyclopenta-[4,5]thieno-[3,2-f][1,2,4]triazolo[4,3-a][1,4]diazepines.

MRP4-inhibitors used are preferably compounds selected from among N-acetyldinitrophenylcysteine, cGMP, cholate, diclofenac, dehydroepiandrosterone 3-glucuronide, dehydroepiandrosterone 3-sulfate, dilazep, dinitrophenyl-5-glutathione, estradiol 17-β-glucuronide, estradiol 3,17-disulfate, estradiol 3-glucuronide, estradiol 3-sulfate, estrone 3-sulfate, flurbiprofen, folate, $N^5$-formyltetrahydrofolate, glycocholate, clycolithocholic acid sulfate, ibuprofen, indomethacin, indoprofen, ketoprofen, lithocholic acid sulfate, methotrexate, MK571 ((E)-3-[[[3-[2-(7-chloro-2-quinolinyl)ethenyl]phenyl]-[[3-dimethylamino)-3-oxopropyl]thio]methyl]thio]propanoic acid), α-naphthyl-β-D-glucuronide, nitrobenzyl mercaptopurine riboside, probenecid, PSC833, sildenafil, sulfinpyrazone, taurochenodeoxycholate, taurocholate, taurodeoxycholate, taurolithocholate, taurolithocholic acid sulfate, topotecan, trequinsin, and zaprinast, dipyridamole, optionally in the form of the racemates, enantiomers, diastereomers, and the pharmacologically acceptable acid addition salts and hydrates thereof.

Preferably the invention relates to the use of MRP4-inhibitors for preparing a pharmaceutical composition for the treatment of respiratory complaints, containing the PDE4B-inhibitors and MRP4-inhibitors, the MRP4-inhibitors preferably being selected from among N-acetyldinitrophenylcysteine, dehydroepiandrosterone 3-sulfate, dilazep, dinitrophenyl-S-glutathione, estradiol 3,17-disulfate, flurbiprofen, glycocholate, glycolithocholic acid sulfate, ibuprofen, indomethacin, indoprofen, lithocholic acid sulfate, MK571, PSC833, sildenafil, taurochenodeoxycholate, taurocholate, taurolithocholate, taurolithocholic acid sulfate, trequinsin, and zaprinast, dipyridamole, optionally in the form of the racemates, enantiomers, diastereomers, and the pharmacologically acceptable acid addition salts and hydrates thereof.

The invention relates more preferably to the use of MRP4-inhibitors for preparing a pharmaceutical composition for treating respiratory complaints, containing the PDE4B-inhibitors and MRP4-inhibitors according to the invention, the MRP4-inhibitors preferably being selected from among dehydroepiandrosterone 3-sulfate, estradiol 3,17-disulfate, flurbiprofen, indomethacin, indoprofen, MK571, taurocholate, optionally in the form of the racemates, enantiomers, diastereomers, and the pharmacologically acceptable acid addition salts and hydrates thereof. The separation of enantiomers from the racemates can be carried out using methods known from the art (e.g., chromatography on chiral phases, etc.).

By acid addition salts with pharmacologically acceptable acids are meant, for example, salts selected from among the hydrochlorides, hydrobromides, hydroiodides, hydrosulfates, hydrophosphates, hydromethanesulfonates, hydronitrates, hydromaleates, hydroacetates, hydrobenzoates, hydrocitrates, hydrofumarates, hydrotartrates, hydroxalates, hydrosuccinates, hydrobenzoates, and hydro-p-toluenesulfonates, preferably the hydrochlorides, hydrobromides, hydrosulfates, hydrophosphates, hydrofumarates, and hydromethanesulfonates.

The invention further relates to pharmaceutical preparations which contain a triple combination of the PDE4B-inhibitors, MRP4-inhibitors, and another active substance according to the invention, such as, for example, an anticholinergic, a steroid, an LTD4-antagonist, or a betamimetic, and the preparation thereof, and the use thereof for treating respiratory complaints.

Formulations

Suitable forms for administration are, for example, tablets, capsules, solutions, syrups, emulsions, or inhalable powders or aerosols. The content of the pharmaceutically effective compound(s) in each case should be in the range from 0.1 to 90 wt. %, preferably 0.5 to 50 wt. % of the total composition, i.e., in amounts which are sufficient to achieve the dosage range specified hereinafter.

The preparations may be administered orally in the form of a tablet, as a powder, as a powder in a capsule (e.g., a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterized by the content of one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example, inert diluents such as calcium carbonate, calcium phosphate, or lactose, disintegrants such as corn starch or alginic acid, binders such as starch or gelatine, lubricants such as magnesium stearate or talc, and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example, collidone or shellac, gum arabic, talc, titanium dioxide, or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol, or sugar, and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may, for example, be prepared by mixing the active substances with inert carriers such as lactose or sorbitol and packing them into gelatine capsules.

Suitable suppositories may be made, for example, by mixing with carriers provided for this purpose, such as neutral fats or polyethyleneglycol or the derivatives thereof.

Excipients which may be used include, for example, water, pharmaceutically acceptable organic solvents such as paraffins (e.g., petroleum fractions), vegetable oils (e.g., groundnut or sesame oil), mono- or polyfunctional alcohols (e.g., ethanol or glycerol), carriers such as, e.g., natural mineral powders (e.g., kaolins, clays, talc, chalk), synthetic mineral powders (e.g., highly dispersed silicic acid and silicates), sugars (e.g., cane sugar, lactose, and glucose), emulsifiers (e.g., lignin, spent sulfite liquors, methylcellulose, starch, and polyvinylpyrrolidone), and lubricants (e.g., magnesium stearate, talc, stearic acid, and sodium lauryl sulfate).

For oral administration the tablets may, of course, contain, apart from the above-mentioned carriers, additives such as sodium citrate, calcium carbonate, and dicalcium phosphate together with various additives such as starch, preferably potato starch, gelatine, and the like. Moreover, lubricants such as magnesium stearate, sodium lauryl sulfate, and talc may be used at the same time for the tabletting process. In the case of aqueous suspensions the active substances may be combined with various flavor enhancers or colorings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g., glucose or arabinose), disaccharides (e.g., lactose, saccharose, maltose), oligo- and polysaccharides (e.g., dextran), polyalcohols (e.g., sorbitol, mannitol, xylitol), salts (e.g., sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronizing and by finally mixing the components together are known from the prior art.

Propellant-Containing Inhalable Aerosols

The propellant-containing inhalable aerosols which may be used according to the invention may contain 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane, or isobutane, and halohydrocarbons such as preferably fluorinated derivatives of methane, ethane, propane, butane, cyclopropane, or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane), and mixtures thereof. The propellant-driven inhalation aerosols used within the scope of the use according to the invention may also contain other ingredients such as co-solvents, stabilizers, surfactants, antioxidants, lubricants, and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulfuric acid, and/or phosphoric acid. Examples of particularly suitable organic acids include ascorbic acid, citric acid, malic acid, tartaric acid, maleic acid, succinic acid, fumaric acid, acetic acid, formic acid, and/or propionic acid, etc. Preferred inorganic acids are hydrochloric and sulfuric acids. It is also possible to use the acids which have already formed an acid addition salt with one of the active substances. Of the organic acids, ascorbic acid, fumaric acid, and citric acid are preferred. If desired, mixtures of the above acids may also be used, particularly in the case of acids which have other properties in addition to their acidifying qualities, e.g., as flavorings, antioxidants, or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g., alcohols—particularly isopropyl alcohol, glycols—particularly propyleneglycol, polyethyleneglycol, polypropylene glycol, glycol ether, glycerol, polyoxyethylene alcohols, and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants, and/or preservatives which guarantee or prolong the shelf life of the finished pharmaceutical formulation, flavorings, vitamins, and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols, and similar vitamins or provitamins occurring in the human body. Preservatives may be used to protect the formulation from contamination with pathogens. Suitable preservatives are those which are known in the art, particularly cetyl pyridinium chloride, benzalkonium chloride, or benzoic acid or benzoates such as sodium benzoate in the concentration known from the prior art.

For the treatment forms described above, ready-to-use packs of a medicament for the treatment of respiratory complaints are provided, containing an enclosed description including, for example, the words respiratory disease, COPD, or asthma, a pteridine and one or more combination partners selected from those described above.

We claim:

1. A method for treating COPD, chronic bronchitis, chronic sinusitis, asthma, Crohn's disease or ulcerative colitis in a patient which comprises administering to the patient in need thereof a therapeutically acceptable amount of a compound of formula 1

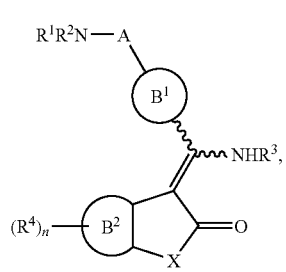

wherein:
A is CO, C=NH, $C_{1-6}$-alkylene, or $C_{3-8}$-cycloalkylene;
$B^1$ is phenyl;

$B^2$ is phenyl;
X is O;
n is 0, 1, 2, or 3;
$R^1$ is H, $C_{1-6}$-haloalkyl, $COR^{1.1}$, $COOR^{1.1}$, or $CH_2COOR^{1.1}$, wherein $R^{1.1}$ is H or $C_{1-6}$-alkyl;
$R^2$ is H, $C_{1-6}$-alkyl, or $C_{1-6}$-haloalkyl; or
$R^1$ and $R^2$ together with the nitrogen form a non-aromatic heterocycle optionally containing one, two, or three heteroatoms selected from oxygen and nitrogen; or
$R^2$, N, A, and $B^1$ together form a bicyclic group of formula (i)

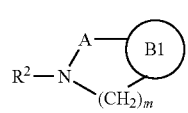

wherein: A is CO, C=NH, or $C_{1-3}$-alkyl, and m is 1, 2, or 3;
$R^3$ is H or a group selected from OH, $C_{1-6}$-haloalkyl, a $C_{6-10}$-aryl, a $C_{5-10}$-heteroaryl, and a $C_{3-10}$-heterocycle, wherein the $C_{3-10}$-heterocycle and the $C_{5-10}$-heteroaryl contain one, two, or three heteroatoms selected from oxygen, sulfur, and nitrogen, optionally substituted by one or more groups selected from $C_{1-6}$-alkyl, $C_{6-10}$-aryl, optionally bridged $C_{3-8}$-cycloalkyl and $C_{1-6}$-haloalkyl, each optionally substituted by a group selected from $C_{1-6}$-alkyl, $C_{1-6}$-haloalkyl, OH, halogen, and $C_{6-10}$-aryl,
$R^3$ is $C_{1-6}$-alkyl optionally substituted by one or more groups selected from halogen, OH, CN, $CONH_2$, CONH—$C_{1-6}$-alkyl, CON($C_{1-6}$-alkyl)$_2$, COOH, COO—$C_{1-6}$-alkyl, COH, CO—$C_{1-6}$ alkyl, CO—$C_{6-10}$-aryl, OH, O—$C_{1-6}$-alkyl, O—$C_{1-6}$-haloalkyl, halogen, SH, $SO_2$—$C_{1-6}$-alkanol, $SO_2$—$C_{1-6}$-alkyl, $SO_2$—$C_{1-6}$-haloalkyl, $SO_2$—$NH_2$, $SO_2$—NH—$C_{1-6}$-alkyl, $SO_2$—N($C_{1-6}$-alkyl)$_2$, $NO_2$, $NH_2$, NH—$C_{1-6}$-alkyl, and N($C_{1-6}$-alkyl)$_2$,
$R^3$ is a group selected from $C_{3-8}$-cycloalkyl, $C_{5-8}$-cycloalkenyl, $C_{1-6}$-alkyl, and $C_{1-6}$-alkanol, each optionally substituted by one or more groups selected from $C_{6-10}$-aryl, $C_{3-8}$-cycloalkyl, a $C_{5-10}$-heteroaryl, and a $C_{3-10}$-heterocycle, each optionally substituted by one or more groups selected from $C_{1-6}$-alkyl, $C_{2-6}$-alkenyl, $C_{2-6}$-alkynyl, $C_{1-6}$-haloalkyl, CN, $CONH_2$, CONH—$C_{1-6}$-alkyl, CON($C_{1-6}$-alkyl)$_2$, COOH, COO—$C_{1-6}$-alkyl, COH, CO—$C_{1-6}$-alkyl, COaryl, OH, O—$C_{1-6}$-alkyl, O—$C_{1-6}$-haloalkyl, halogen, SH, S—$C_{1-6}$-alkyl, S—$C_{1-6}$-haloalkyl, $SO_2$—$C_{1-6}$-alkanol, $SO_2$—$C_{1-6}$-alkyl, $SO_2$—$C_{1-6}$-haloalkyl, $SO_2$—$NH_2$, $SO_2$—NH—$C_{1-6}$-alkyl, $SO_2$—N($C_{1-6}$-alkyl)$_2$, $NO_2$, $NH_2$, NH—$C_{1-6}$-alkyl, N($C_{1-6}$-alkyl)$_2$, a $C_{5-10}$-heteroaryl, and a $C_{3-10}$-heterocycle, wherein the $C_{5-10}$-heteroaryl and the $C_{3-10}$-heterocycle are each optionally substituted by a group selected from oxo, hydroxyl, halogen, $C_{1-6}$-alkyl, and $C_{1-6}$-haloalkyl,
$R^3$ is a group selected from $C_{6-10}$-aryl, a $C_{6-10}$-heteroaryl, and a $C_{3-10}$-heterocycle, each optionally substituted by one or more groups selected from aryl, $C_{1-6}$-alkyl, $C_{2-6}$-alkenyl, $C_{2-6}$-alkynyl, $C_{1-6}$-haloalkyl, $CONH_2$, CONH—$C_{1-6}$-alkyl, CON($C_{1-6}$-alkyl)$_2$, COOH, COO—$C_{1-6}$-alkyl, COH, CO—$C_{1-6}$-alkyl, CO—$C_{6-10}$-aryl, OH, O—$C_{1-6}$-alkyl, O—$C_{1-6}$-haloalkyl, halogen, SH, S—$C_{1-6}$-alkyl, S—$C_{1-6}$-haloalkyl, $SO_2$—$C_{1-6}$-alkyl, $SO_2$—$C_{1-6}$-alkanol, $SO_2$—$C_{1-6}$-haloalkyl, $SO_2$—$NH_2$, $SO_2$—NH—$C_{1-6}$-alkyl, $SO_2$—N($C_{1-6}$-alkyl)$_2$, $NO_2$, $NH_2$, NH—$C_{1-6}$-alkyl, N($C_{1-6}$-alkyl)$_2$, and N—($SO_2$—$C_{1-4}$-alkyl)($R^{3.4}$),
$R^3$ is a group selected from $C_{1-6}$-alkyl, $C_{6-10}$-aryl-$C_{1-6}$-alkylene, $C_{5-10}$-heteroaryl-$C_{1-6}$-alkylene, $C_{3-7}$-cycloalkyl, $C_{6-10}$-aryl, a $C_{5-10}$-heteroaryl, and a $C_{3-10}$-heterocycle, each optionally substituted by one or more groups selected from B, halogen, OH, $C_{1-6}$-alkyl, and oxo, wherein B is a group of formula 2

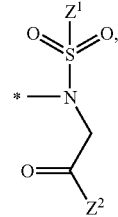

wherein:
$Z^1$ is H, OH, halogen, $C_{1-6}$-alkyl, $C_{1-6}$-alkanol, O($C_{1-6}$-alkyl), $C_{6-10}$-aryl, O—$C_{6-10}$-aryl, $NH_2$, NH($C_{1-6}$-alkyl), N($C_{1-6}$-alkyl)$_2$, or $C_{3-7}$-cycloalkyl, and
$Z^2$ is OH, $NH_2$, NH($C_{1-6}$-alkyl), N($C_{1-6}$-alkyl)$_2$, O($C_{1-6}$-alkyl), mono- or bicyclic $C_{3-7}$-cycloalkyl, mono- or bicyclic $C_{3-10}$-heterocycle, mono- or bicyclic $C_{5-10}$-heteroaryl, or $C_{6-10}$-aryl,
$R^3$ is a group selected from $C_{6-10}$-aryl and a $C_{5-10}$-heteroaryl, each optionally substituted by $C_{1-6}$-alkyl optionally substituted by a group selected from $COOR^{3.3}$, $NR^{3.3}R^{3.4}$, $NHCOR^{3.3}$, $NHCOOR^{3.3}$, and phenyl optionally substituted by a group selected from $C_{1-6}$-alkyl, $C_{2-6}$-alkenyl, $C_{2-6}$-alkynyl, CN, $C_{1-6}$-haloalkyl, $CONH_2$, CONH—$C_{1-6}$-alkyl, CON($C_{1-6}$-alkyl)$_2$, COOH, COO—$C_{1-6}$-alkyl, COH, CO—$C_{1-6}$-alkyl, OH, O—$C_{1-6}$-alkyl, O—$C_{1-6}$-haloalkyl, halogen, SH, S—$C_{1-6}$-alkyl, S—$C_{1-6}$-haloalkyl, $SO_2$—$C_{1-6}$-alkyl, $SO_2$—$C_{1-6}$-haloalkyl, $SO_2$—$NH_2$, $SO_2$—NH—$C_{1-6}$-alkyl, $SO_2$—N($C_{1-6}$-alkyl)$_2$, $NO_2$, $NH_2$, NH—

$C_{1-6}$-alkyl, and $N(C_{1-6}$-alkyl$)_2$, a $C_{3-10}$-heterocycle, and a $C_{5-10}$-heteroaryl, wherein the $C_{3-10}$-heterocycle and the $C_{5-10}$-heteroaryl are each optionally substituted by an oxo group or a methyl group, wherein:
$R^{3.3}$ is H or $C_{1-6}$-alkyl, and
$R^{3.4}$ is H, $C_{1-6}$-alkyl, or $C_{7-11}$-aralkyl, $C_{1-6}$-alkylene, or $C_{5-10}$-heteroaryl-$C_{1-6}$-alkylene,
$R^3$ is a group selected from $C_{6-10}$-aryl and a $C_{5-10}$-heteroaryl, each optionally substituted by $NR^{1.1}R^{3.2}$, wherein:
  $R^{3.1}$ is H, $C_{1-6}$-alkyl, $C_{3-6}$-cycloalkyl, $C_{1-6}$-haloalkyl, $COR^{3.1.1}$, $COOR^{3.1.1}$, $CONR^{3.1.1}R^{3.1.2}$, or $SO_2$—$R^{3.1.1}$, wherein $R^{3.1.1}$ is H, $C_{1-6}$-alkyl, $C_{1-6}$-haloalkyl, $C_{3-6}$-cycloalkyl, or $C_{6-10}$-aryl, and $R^{3.1.2}$ is H, $C_{1-6}$-alkyl, $C_{1-6}$-haloalkyl, $C_{3-6}$-cycloalkyl, or $C_{6-10}$-aryl, and
  $R^{3.2}$ is H or a group selected from $C_{1-6}$-alkyl, $C_{3-6}$-cycloalkyl, and $C_{1-6}$-haloalkyl, each optionally substituted by one or more groups selected from $NH_2$, $NH(C_{1-6}$-alkyl), $N(C_{1-6}$-alkyl$)_2$, oxo, and a non-aromatic $C_{3-10}$-heterocycle containing one or two heteroatoms selected from nitrogen, oxygen, and sulfur, wherein the non-aromatic $C_{3-10}$-heterocycle is optionally substituted by $C_{1-4}$-alkyl, or
$R^3$ is a group selected from $C_{6-10}$-aryl and a $C_{5-10}$-heteroaryl, each optionally substituted by a $C_{3-10}$-heterocycle optionally substituted by one or more groups selected from $C_{6-10}$-aryl, $C_{1-6}$-alkyl, $C_{3-6}$-cycloalkyl, CN, $C_{1-6}$-haloalkyl, $CONH_2$, CONH—$C_{1-6}$-alkyl, CON($C_{1-6}$-alkyl$)_2$, COOH, COO—$C_{1-6}$-alkyl, COH, CO—$C_{1-6}$-alkyl, oxo, OH, O—$C_{1-6}$-alkyl, halogen, SH, S—$C_{1-6}$-alkyl, $NH_2$, NH—$C_{1-6}$-alkyl, and $N(C_{1-6}$-alkyl$)_2$, or
$R^3$ is benzimidazolyl optionally substituted by a group selected from $C_{1-6}$-alkyl, $C_{1-6}$-haloalkyl, and $C_{3-6}$-cycloalkyl; and
$R^4$ is $C_{1-6}$ alkyl, $C_{3-8}$-cycloalkyl, $C_{1-6}$-haloalkyl, $OR^{4.1}$, $NR^{4.1}R^{4.2}$, CN, or halogen, wherein: $R^{4.1}$ is H, $C_{1-6}$-alkyl, $C_{3-8}$-cycloalkyl, or $C_{1-6}$-haloalkyl, and $R^{4.2}$ is H, $C_{1-6}$-alkyl, $C_{3-8}$-cycloalkyl, or $C_{1-6}$-haloalkyl;
or a pharmacologically acceptable salt, enantiomer or hydrate thereof.

2. The method of claim 1, wherein in the compound of formula 1:
$B^1$ is phenyl;
$B^2$ is phenyl;
X is O;
n is 0, 1, 2, or 3;
$R^1$ is H, $C_{1-4}$-alkyl, or $C_{1-4}$-haloalkyl;
$R^2$ is H, $C_{1-4}$-alkyl, or $C_{1-4}$-haloalkyl; or
$R^1$ and $R^2$ together with the nitrogen form a non-aromatic heterocycle containing one or two nitrogen atoms;
$R^3$ is H, OH, $C_{1-6}$-haloalkyl, or a group selected from $C_{6-10}$-aryl, a $C_{5-10}$-heteroaryl, and a $C_{3-10}$-heterocycle, each optionally substituted by a methyl group, oxo, or OH,
$R^3$ is $C_{1-6}$-alkyl optionally substituted by one or more groups selected from halogen, OH, CN, $CONH_2$, CONH—$C_{1-6}$-alkyl, CON($C_{1-6}$-alkyl$)_2$, COOH, COO—$C_{1-6}$-alkyl, COH, CO—$C_{1-6}$-alkyl, COaryl, OH, O—$C_{1-6}$-alkyl, O—$C_{1-6}$-haloalkyl, halogen, SH, S—$C_{1-6}$-alkyl, S—$C_{1-6}$-haloalkyl, $SO_2$—$C_{1-6}$-alkanol, $SO_2$—$C_{1-6}$-alkyl, $SO_2$—$C_{1-6}$-haloalkyl, $SO_2$—$NH_2$, $SO_2$—NH—$C_{1-6}$-alkyl, $SO_2$—$N(C_{1-6}$-alkyl$)_2$, $NO_2$, $NH_2$, NH—$C_{1-6}$-alkyl, and $N(C_{1-6}$-alkyl$)_2$,
$R^3$ is a group selected from $C_{3-8}$-cycloalkyl, a $C_{3-8}$-cycloalkyl bridged by $C_{1-3}$-alkylene, $C_{5-8}$-cycloalkenyl, $C_{1-6}$-alkyl, and $C_{1-6}$-alkanol, each optionally substituted by one or more groups selected from $C_{6-10}$-aryl, $C_{3-8}$-cycloalkyl, $C_{5-10}$-heteroaryl, and a $C_{3-10}$-heterocycle, each optionally substituted by one or more groups selected from $C_{1-6}$-alkyl, $C_{1-6}$-haloalkyl, CN, OH, O—$C_{1-6}$-alkyl, O—$C_{1-6}$-haloalkyl, halogen, S—$C_{1-6}$-alkyl, S—$C_{1-6}$-haloalkyl, $NO_2$, $NH_2$, NH—$C_{1-6}$-alkyl, $N(C_{1-6}$-alkyl$)_2$, a $C_{5-10}$-heteroaryl, and a $C_{3-10}$-heterocycle, wherein the $C_{5-10}$-heteroaryl and the $C_{3-10}$-heterocycle are each optionally substituted by a group selected from oxo, hydroxyl, halogen, $C_{1-6}$-alkyl, and $C_{1-6}$-haloalkyl,
$R^3$ is a group selected from $C_{1-6}$-alkyl, $C_{6-10}$-aryl-$C_{1-6}$-alkylene, $C_{5-10}$-heteroaryl-$C_{1-6}$-alkylene, $C_{3-7}$-cycloalkyl, $C_{6-10}$-aryl, $C_{5-10}$-heteroaryl, and a $C_{3-10}$-heterocycle, each substituted one or more groups selected from B, halogen, OH, $C_{1-6}$-alkyl, oxo, wherein B is a group of formula 2

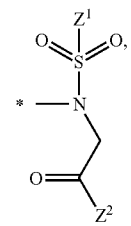

wherein:
$Z^1$ is H, OH, halogen, $C_{1-6}$-alkyl, $C_{1-6}$-alkanol, $O(C_{1-6}$-alkyl), $C_{6-10}$-aryl, O—$C_{6-10}$-aryl, $NH_2$, $NH(C_{1-6}$-alkyl), $N(C_{1-6}$-alkyl$)_2$, or $C_{3-7}$-cycloalkyl, and
$Z^2$ is OH, $NH_2$, $NH(C_{1-6}$-alkyl), $N(C_{1-6}$-alkyl$)_2$, O($C_{1-6}$-alkyl), mono- or bicyclic $C_{3-7}$-cycloalkyl, a mono- or bicyclic $C_{3-10}$-heterocycle, a mono- or bicyclic $C_{5-10}$-heteroaryl, or $C_{6-10}$-aryl,
$R^3$ is phenyl optionally substituted by one or more groups selected from $C_{6-10}$-aryl, $C_{2-6}$-alkenyl, $C_{2-6}$-alkynyl, $C_{1-6}$-haloalkyl, $CONH_2$, CONH—$C_{1-6}$-alkyl, CON($C_{1-6}$-alkyl$)_2$, COOH, COO—$C_{1-6}$-alkyl, COH, CO—$C_{1-6}$-alkyl, COaryl, OH, O—$C_{1-6}$-alkyl, O—$C_{1-4}$-haloalkyl, halogen, SH, S—$C_{1-6}$-alkyl, S—$C_{1-4}$-haloalkyl, $SO_2$—$C_{1-6}$-alkyl, $SO_2$—$C_{1-4}$-haloalkyl, $SO_2$—$NH_2$, $SO_2$—NH—$C_{1-6}$-alkyl, $SO_2$—$N(C_{1-6}$-alkyl$)_2$, $NO_2$, $NO_2$, $NH_2$, NH—$C_{1-6}$-alkyl, and $N(C_{1-6}$-alkyl$)_2$,
$R^3$ is phenyl substituted by $C_{1-4}$-alkyl optionally substituted by a group selected from $COOR^{3.3}$, $NR^{3.3}R^{3.4}$, $NHCOR^{3.3}$, $NHCOOR^{3.3}$, and phenyl, each optionally substituted by one or more groups selected from methyl, tert-butyl, F, Cl, Br, CN, OH, and a heterocycle containing one, two, or three heteroatoms selected from oxygen and nitrogen, wherein the heterocycle is optionally substituted by an oxo group or a methyl group, wherein:
$R^{3.3}$ is H or $C_{1-6}$-alkyl, and
$R^{3.4}$ is H, $C_{1-6}$-alkyl, $C_{6-10}$-aryl-$C_{1-6}$-alkylene, or $C_{5-10}$-heteroaryl-$C_{1-6}$-alkylene,
$R^3$ is phenyl substituted with $NR^{3.1}R^{3.2}$, wherein:
  $R^{3.1}$ is H, $C_{1-4}$-alkyl, $C_{1-4}$-haloalkyl, $COR^{3.1.1}$, $COOR^{3.1.1}$, $CONR^{3.1.1}R^{3.1.2}$, or $SO_2$—$R^{3.1.1}$, wherein $R^{3.1.1}$ is H, $C_{1-4}$-alkyl, $C_{1-4}$-haloalkyl, $C_{3-6}$-cycloalkyl, or $C_{6-10}$-aryl, and $R^{3.1.2}$ is H, $C_{1-4}$-alkyl, $C_{1-4}$-haloalkyl, $C_{3-6}$-cycloalkyl, or $C_{6-10}$-aryl, and
  $R^{3.2}$ is H or $C_{1-4}$-alkyl optionally substituted by one or more groups selected from $NH_2$, $NH(C_{1-4}$-alkyl), N($C_{1-4}$-alkyl)$_2$, oxo, or a non-aromatic $C_{3-10}$-heterocycle optionally containing one or two nitrogen atoms and optionally substituted by a methyl group, $R^3$ is $C_{6-10}$-aryl optionally substituted by a $C_{5-10}$-heteroaryl containing one, two, or three heteroatoms selected from oxygen, sulfur, and nitrogen, and optionally substituted by one or more groups selected from $C_{6-10}$-aryl, $C_{1-4}$-alkyl, $C_{3-6}$-cycloalkyl, CN, $C_{1-4}$-haloalkyl, CONH$_2$, CONH—$C_{1-4}$-alkyl, CON($C_{1-4}$-alkyl)$_2$, COOH, COO—$C_{1-4}$-alkyl, COH, CO—$C_{1-4}$-alkyl, OH, O—$C_{1-4}$-alkyl, halogen, SH, S—$C_{1-4}$-alkyl, NH$_2$, NH—$C_{1-4}$-alkyl, and N($C_{1-4}$-alkyl)$_2$, $R^3$ is $C_{6-10}$-aryl optionally substituted by a non-aromatic $C_{3-10}$-heterocycle optionally containing one or two heteroatoms selected from oxygen, sulfur, and nitrogen, wherein the $C_{3-10}$-heterocycle is optionally substituted by one or more groups selected from $C_{1-4}$-alkyl and oxo, or $R^3$ is benzimidazolyl optionally substituted by one or more groups selected from $C_{1-4}$-alkyl, $C_{1-4}$-haloalkyl, and $C_{3-6}$-cycloalkyl;

$R^4$ is $C_{1-4}$-alkyl, $C_{3-6}$-cycloalkyl, $C_{1-4}$-haloalkyl, OR$^{4.1}$, NR$^{4.1}$R$^{4.2}$, CN, or halogen, wherein:

$R^{4.1}$ is H, $C_{1-4}$-alkyl, $C_{3-6}$-cycloalkyl, or $C_{1-4}$-haloalkyl, and $R^{4.2}$ is H, $C_{1-4}$-alkyl, $C_{3-6}$-cycloalkyl, or $C_{1-4}$-haloalkyl;

or a pharmacologically acceptable salt, enantiomer or hydrate thereof.

3. The method of claim 1, wherein in the compound of formula 1:

$R^3$ is $C_{1-6}$-alkyl optionally substituted by one or more groups selected from halogen, OH, CN, CONH$_2$, CONH—$C_{1-6}$-alkyl, CON($C_{1-6}$-alkyl)$_2$, COOH, COO—$C_{1-6}$-alkyl, COH, CO—$C_{1-6}$-alkyl, COaryl, OH, O—$C_{1-6}$-alkyl, O—$C_{1-6}$-haloalkyl, halogen, SH, S—$C_{1-6}$-alkyl, S—$C_{1-6}$-haloalkyl, SO$_2$—$C_{1-6}$-alkanol, SO$_2$—$C_{1-6}$-alkyl, SO$_2$—$C_{1-6}$-haloalkyl, SO$_2$—NH$_2$, SO$_2$—NH—$C_{1-6}$-alkyl, SO$_2$—N($C_{1-6}$-alkyl)$_2$, NO$_2$, NH$_2$, NH—$C_{1-6}$-alkyl, and N($C_{1-6}$-alkyl)$_2$, $R^3$ is a group selected from $C_{3-8}$-cycloalkyl, a $C_{3-8}$-cycloalkyl bridged with $C_{1-3}$-alkylene, a $C_{5-8}$-cycloalkenyl, $C_{1-6}$-alkyl, and $C_{1-6}$-alkanol, each optionally substituted by one or more groups selected from $C_{6-10}$-aryl, $C_{3-8}$-cycloalkyl, a $C_{5-10}$-heteroaryl, and a $C_{3-10}$-heterocycle, each optionally substituted by one or more groups selected from $C_{1-6}$-alkyl, $C_{2-6}$-alkenyl, $C_{2-6}$-alkynyl, $C_{1-6}$-haloalkyl, CN, CONH$_2$, CONH—$C_{1-6}$-alkyl, CON($C_{1-6}$-alkyl)$_2$, COOH, COO—$C_{1-6}$-alkyl, COH, CO—$C_{1-6}$-alkyl, CO—$C_{6-10}$-aryl, OH, O—$C_{1-6}$-alkyl, O—$C_{1-6}$-haloalkyl, halogen, SH, S—$C_{1-6}$-alkyl, S—$C_{1-6}$-haloalkyl, SO$_2$—$C_{1-6}$-alkanol, SO$_2$—$C_{1-6}$-alkyl, SO$_2$—$C_{1-6}$-haloalkyl, SO$_2$—NH$_2$, SO$_2$—NH—$C_{1-6}$-alkyl, SO$_2$—N($C_{1-6}$-alkyl)$_2$, NO$_2$, NH$_2$, NH—$C_{1-6}$-alkyl, N($C_{1-6}$-alkyl)$_2$, $C_{5-10}$-heteroaryl, and a $C_{3-10}$-heterocycle, each optionally substituted by one or more groups selected from oxo, hydroxyl, halogen, or $C_{1-6}$-alkyl, and $C_{1-6}$-haloalkyl, $R^3$ is a group selected from $C_{6-10}$-aryl, $C_{5-10}$-heteroaryl, and a $C_{3-10}$-heterocycle, each optionally substituted by one or more groups selected from $C_{6-10}$-aryl, $C_{1-6}$-alkyl, $C_{2-6}$-alkenyl, $C_{2-6}$-alkynyl, $C_{1-6}$-haloalkyl, CONH$_2$, CONH—$C_{1-6}$-alkyl, CON($C_{1-6}$-alkyl)$_2$, COOH, COO—$C_{1-6}$-alkyl, COH, CO—$C_{1-6}$-alkyl, CO—$C_{6-10}$-aryl, OH, O—$C_{1-6}$-alkyl, O—$C_{1-6}$-haloalkyl, halogen, SH, S—$C_{1-6}$-alkyl, S—$C_{1-6}$-haloalkyl, SO$_2$—$C_{1-6}$-alkyl, SO$_2$—$C_{1-6}$-alkanol, SO$_2$—$C_{1-6}$-haloalkyl, SO$_2$—NH$_2$, SO$_2$—NH—$C_{1-6}$-alkyl, SO$_2$—N($C_{1-6}$-alkyl)$_2$, NO$_2$, NH$_2$, NH $C_{1-6}$ alkyl, N($C_{1-6}$-alkyl)$_2$, and N—(SO$_2$—$C_{1-4}$-alkyl)(R$^{3.4}$), or $R^3$ is a group selected from $C_{1-6}$-alkyl, $C_{6-10}$-aryl-$C_{1-6}$-alkylene, $C_{5-10}$-heteroaryl-$C_{1-6}$-alkylene, $C_{3-7}$-cycloalkyl, $C_{6-10}$-aryl, $C_{5-10}$-heteroaryl, and a $C_{3-10}$-heterocycle, each optionally substituted by one or more groups selected from B, halogen, OH, $C_{1-6}$-alkyl, and oxo, wherein B is a group of formula 2

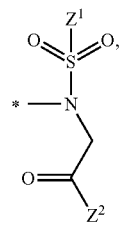

wherein:

$Z^1$ is H, OH, halogen, $C_{1-6}$-alkyl, $C_{1-6}$-alkanol, O($C_{1-6}$-alkyl), $C_{6-10}$-aryl, O—$C_{6-10}$-aryl, NH$_2$, NH($C_{1-6}$-alkyl), N($C_{1-6}$-alkyl)$_2$, or $C_{3-7}$-cycloalkyl, and $Z^2$ is OH, NH$_2$, NH($C_{1-6}$-alkyl), N($C_{1-6}$-alkyl)$_2$, O($C_{1-6}$-alkyl), mono- or bicyclic $C_{3-7}$-cycloalkyl, mono- or bicyclic $C_{5-10}$-heteroaryl, mono- or bicyclic $C_{3-10}$-heterocycle, or $C_{6-10}$-aryl, or a pharmacologically acceptable salt, enantiomer or hydrate thereof.

4. The method of claim 3, wherein in the compound of formula 1:

A is CH$_2$, CD$_2$, C=NH, CHMe, CMe$_2$, 1,1'-cyclopropylene, or 1,1'-cyclobutylidene;

B$^1$ and B$^2$ are each phenyl;

X is O and $R^1$ and $R^2$ are each H, or a pharmacologically acceptable salt, enantiomer or hydrate thereof.

5. The method of claim 4, wherein in the compound of formula 1:

$R^3$ is $C_{1-6}$-alkyl optionally substituted by one or more groups selected from halogen, OH, CN, CONH$_2$, CONH—$C_{1-6}$-alkyl, CON($C_{1-6}$-alkyl)$_2$, COOH, COO—$C_{1-6}$-alkyl, COH, CO—$C_{1-6}$-alkyl, CO—$C_{6-10}$-aryl, OH, O—$C_{1-6}$-alkyl, SO$_2$—$C_{1-6}$-alkanol, SO$_2$—$C_{1-6}$-alkyl, SO$_2$—$C_{1-6}$-haloalkyl, SO$_2$—NH$_2$, SO$_2$—NH—$C_{1-6}$-alkyl, SO$_2$—N($C_{1-6}$-alkyl)$_2$, NO$_2$, NH$_2$, NH—$C_{1-6}$-alkyl, and N($C_{1-6}$-alkyl)$_2$, $R^3$ is a group selected from $C_{3-8}$-cycloalkyl, a $C_{3-8}$-cycloalkyl bridged by $C_{1-3}$-alkylene, and $C_{1-6}$-alkyl, each optionally substituted by one or more groups selected from $C_{6-10}$-aryl, $C_{3-8}$-cycloalkyl, a $C_{5-10}$-heteroaryl, and a $C_{3-10}$-heterocycle, each optionally substituted by one or more groups selected from $C_{1-6}$-alkyl, $C_{2-6}$-alkenyl, $C_{2-6}$-alkynyl, $C_{1-6}$-haloalkyl, CN, CONH$_2$, CONH—$C_{1-6}$-alkyl, CON($C_{1-6}$-alkyl)$_2$, COOH, COO—$C_{1-6}$-alkyl, COH, CO—$C_{1-6}$-alkyl, CO—$C_{6-10}$-aryl, OH, O—$C_{1-6}$-alkyl, O—$C_{1-6}$-haloalkyl, halogen, SH, S—$C_{1-6}$-alkyl, S—$C_{1-6}$-haloalkyl, SO$_2$—$C_{1-6}$-alkanol, SO$_2$—$C_{1-6}$-alkyl, SO$_2$—$C_{1-6}$-haloalkyl, SO$_2$—NH$_2$, SO$_2$—NH—$C_{1-6}$-alkyl, SO$_2$—N($C_{1-6}$-alkyl)$_2$, NO$_2$, NH$_2$, NH—$C_{1-6}$-alkyl, N($C_{1-6}$-alkyl)$_2$, $C_{5-10}$-heteroaryl, and a $C_{3-10}$-heterocycle, each optionally substituted by one or more groups selected from oxo, hydroxyl, halogen, or $C_{1-6}$-alkyl, and $C_{1-6}$-haloalkyl, $R^3$ is a group selected from $C_{6-10}$-aryl, a $C_{3-8}$-heterocycle with 1 to 4 heteroatoms selected from N, O, and S, and a $C_{5-10}$-heteroaryl with 1 to 2 heteroatoms selected from N, O, and S, each optionally substituted by one or more groups selected from $C_{6-10}$-aryl, $C_{1-6}$-alkyl, $C_{1-6}$-haloalkyl, $CONH_2$, $CONH$—$C_{1-6}$-alkyl, $CON(C_{1-6}$-alkyl$)_2$, COOH, COO—$C_{1-6}$-alkyl, COH, CO—$C_{1-6}$-alkyl, CO—$C_{6-10}$-aryl, OH, O—$C_{1-6}$-alkyl, O—$C_{1-6}$-haloalkyl, halogen, $SO_2$—$C_{1-6}$-alkyl, $SO_2$—$C_{1-6}$-alkanol, $SO_2$—$C_{1-6}$-haloalkyl, $SO_2$—$NH_2$, $SO_2$—NH—$C_{1-6}$-alkyl, $SO_2$—$N(C_{1-6}$-alkyl$)_2$, $NO_2$, $NH_2$, NH—$C_{1-6}$-alkyl, $N(C_{1-6}$-alkyl$)_2$, and N—$(SO_2$—$C_{1-4}$-alkyl)$(R^{3.4})$, wherein $R^{3.4}$ is a $C_{5-10}$-heteroaryl-$C_{1-6}$-alkylene, or $R^3$ is a group selected from $C_{1-6}$-alkyl, $C_{6-10}$-aryl-$C_{1-6}$-alkylene, $C_{5-10}$-heteroaryl-$C_{1-6}$-alkylene, $C_{3-7}$-cycloalkyl, $C_{6-10}$-aryl, $C_{3-8}$-heterocycle with 1 to 4 heteroatoms selected from N, O, and S, and a $C_{5-10}$-heteroaryl with 1 to 2 heteroatoms selected from N, O, and S, each optionally substituted by one or more groups selected from B, halogen, OH, $C_{1-6}$-alkyl, and oxo, wherein B is a group of formula 2

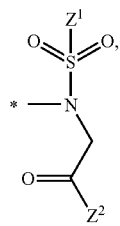

2 wherein:
$Z^1$ is H, OH, halogen, $C_{1-6}$-alkyl, $C_{1-6}$-alkanol, or O($C_{1-6}$-alkyl), and
$Z^2$ is OH, $NH_2$, $NH(C_{1-6}$-alkyl), $N(C_{1-6}$-alkyl$)_2$, O($C_{1-6}$-alkyl), mono- or bicyclic $C_{3-7}$-cycloalkyl, mono- or bicyclic $C_{5-10}$-heteroaryl, mono- or bicyclic $C_{3-10}$-heterocycle, or $C_{6-10}$-aryl; and
$R^4$ is H, F, or Cl,
or a pharmacologically acceptable salt, enantiomer or hydrate thereof.

6. The method of claim 1, wherein in the compound of formula 1:
A is CO, C=NH, $C_{1-4}$-alkylene, $C_{3-6}$-cycloalkylene, $C_{1-6}$-alkylene, or $C_{3-8}$-cycloalkylene;
$B^1$ is phenyl;
$B^2$ is phenyl;
X is O;
n is 0, 1, 2, or 3;
$R^1$ is H, methyl, ethyl, or propyl;
$R^2$ is H, methyl, ethyl, or propyl;
$R^3$ is H, OH, $C_{1-6}$-haloalkyl, or $C_{6-10}$-aryl, or a group selected from a $C_{5-10}$-heteroaryl and a $C_{3-10}$-cycloalkyl, each containing one, two, or three nitrogen atoms and optionally substituted by a methyl group,
$R^3$ is a group selected from cyclopentyl, cyclohexyl, cyclopentenyl, cyclohexenyl, methyl, ethyl, propyl, and butyl, each optionally substituted by one or more groups selected from $C_{6-10}$-aryl and a $C_{5-10}$-heterocycle, each optionally substituted by one or more groups selected from $C_{1-6}$-alkyl, $C_{1-6}$-haloalkyl, CN, OH, O—$C_{1-6}$-alkyl, O—$C_{1-6}$-haloalkyl, halogen, $NO_2$, $NH_2$, NH—$C_{1-6}$-alkyl, and $N(C_{1-6}$-alkyl$)_2$, $R^3$ is phenyl optionally substituted by one or more groups selected from $C_{6-10}$-aryl, $C_{2-4}$-alkenyl, $C_{2-4}$-alkynyl, $C_{1-4}$-haloalkyl, $CONH_2$, CONH—$C_{1-4}$-alkyl, CON($C_{1-4}$-alkyl$)_2$, COOH, COO—$C_{1-4}$-alkyl, COH, CO—$C_{1-4}$-alkyl, CO—$C_{6-10}$-aryl, OH, O—$C_{1-4}$-alkyl, O—$C_{1-4}$-haloalkyl, halogen, SH, S—$C_{1-4}$-haloalkyl, $SO_2$—$C_{1-4}$-alkyl, $SO_2$—$C_{1-4}$-haloalkyl, $SO_2$—$NH_2$, $SO_2$—NH—$C_{1-4}$-alkyl, $SO_2$—$N(C_{1-4}$-alkyl$)_2$, $NO_2$, $NO_2$, $NH_2$, NH—$C_{1-4}$-alkyl, and $N(C_{1-4}$-alkyl$)_2$, $R^3$ is phenyl optionally substituted by $C_{1-4}$-alkyl optionally substituted by a group selected from $COOR^{3.3}$, $NR^{3.3}R^{3.4}$, $NHCOR^{3.3}$, $NHCOOR^{3.3}$, p-fluorophenyl, and a heterocycle containing one, two, or three heteroatoms selected from oxygen and nitrogen and optionally substituted by an oxo group, wherein:
$R^{3.3}$ is H or $C_{1-4}$-alkyl, and
$R^{3.4}$ is H, $C_{1-4}$-alkyl, $C_{6-10}$-aryl-$C_{1-6}$-alkylene, or $C_{5-10}$-heteroaryl-$C_{1-6}$-alkylene, $R^3$ is phenyl optionally substituted by $NR^{3.1}R^{3.2}$, wherein:
$R^{3.1}$ is H, $C_{1-4}$-alkyl, $COR^{3.1.1}$, $COOR^{3.1.1}$, $CONR^{3.1.1}R^{3.1.2}$, or $SO_2$—$R^{3.1.1}$, wherein $R^{3.1.1}$ is H, $C_{1-4}$-alkyl, or $C_{6-10}$-aryl, and $R^{3.1.2}$ is H, $C_{1-4}$-alkyl, or $C_{6-10}$-aryl, and
$R^{3.2}$ is H or $C_{1-4}$-alkyl optionally substituted by one or more groups selected from $NH_2$, $NH(C_{1-4}$-alkyl), $N(C_{1-4}$-alkyl$)_2$, oxo, or a $C_{3-10}$-heterocycle containing one or two nitrogen atoms and optionally substituted by a methyl group, $R^3$ is phenyl optionally substituted by a $C_{5-10}$-heteroaryl containing one, two, or three heteroatoms selected from oxygen, sulfur, and nitrogen, wherein the $C_{5-10}$-heteroaryl is optionally substituted by one or more groups selected from $C_{6-10}$-aryl, $C_{1-4}$-alkyl, $C_{1-4}$-haloalkyl, $C_{3-6}$-cycloalkyl, CN, $CONH_2$, CONH—$C_{1-4}$-alkyl, CON($C_{1-4}$-alkyl$)_2$, COOH, COO—$C_{1-4}$-alkyl, COH, CO—$C_{1-4}$-alkyl, OH, O—$C_{1-4}$-alkyl, halogen, $NH_2$, and $N(C_{1-4}$-alkyl$)_2$, $R^3$ is phenyl optionally substituted by a $C_{5-10}$-heteroaryl containing one, two, or three heteroatoms selected from oxygen, sulfur, and nitrogen, wherein the $C_{5-10}$-heteroaryl is optionally substituted by one or more groups selected from $C_{1-4}$-alkyl and oxo, or
$R^3$ is benzimidazolyl optionally substituted by one or more groups selected from methyl, ethyl, propyl, $CF_3$, $CH_2CF_3$, cyclopropyl, cyclopentyl, and cyclohexyl;
$R^4$ is $C_{1-4}$-alkyl, $C_{1-4}$-haloalkyl, or halogen;
or a pharmacologically acceptable salt, enantiomer or hydrate thereof.

7. The method of claim 1, wherein the compound of formula 1 is of the formula 1a:

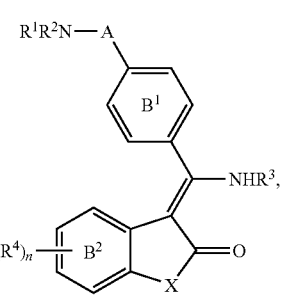

1a wherein A, X, n, R$^1$, R$^2$, R$^3$, and R$^4$ are as defined in claim 1, or a pharmacologically acceptable salt, enantiomer or hydrate thereof.

8. The method of claim 1, wherein in the compound of formula 1:
A is CH$_2$, CHMe, CMe$_2$, C=NH, 1,1'-cyclopropylene, or 1,1'-cyclobutylidene;
X is O;
n is 0, 1, or 2;
R$^1$ is H, methyl, or ethyl;
R$^2$ is H, methyl, or ethyl;
R$^3$ is H, cyclopropyl, cyclobutyl, N-methylpiperidinyl, pyridinyl, phenyl, or 4-phenylcyclohexane,
R$^3$ is phenyl optionally substituted by one or more groups selected from phenyl, methyl, ethyl, propyl, butyl, CF$_3$, CONH$_2$, CONHMe, CONMe$_2$, COOH, COOMe, COOEt, COH, COMe, OH, OMe, OEt, F, Cl, Br, SH, SO$_2$Me, SONH$_2$, SONMe$_2$, NO$_2$, NH$_2$, NHMe, and NMe$_2$,
R$^3$ is phenyl optionally substituted by a group selected from methyl and ethyl, each optionally substituted by one or more groups selected from COOH, COOMe, NH$_2$, NMe$_2$, NHCOMe, NHCOO-tert-butyl, NMe(benzyl), p-fluorophenyl, pyrrolidinyl, piperidinyl, morpholinyl, pyrrolidin-2-onyl, imidazolyl, and triazolyl,
R$^3$ is phenyl substituted by NR$^{3.1}$R$^{3.2}$, wherein R$^{3.1}$ is H, methyl, COH, COMe, COOMe, CONH$_2$, CONMe$_2$, SO$_2$Me, SO$_2$CF$_3$, or SO$_2$-phenyl, and R$^{3.2}$ is H or a group selected from methyl and ethyl, each optionally substituted by one or more groups selected from NH$_2$, NHMe, NMe$_2$, N-piperidinyl, N-morpholinyl, and N-methylpiperazinyl, wherein the N-piperidinyl, N-morpholinyl, and the N-methylpiperazinyl are each optionally substituted by a further oxo,
R$^3$ is phenyl optionally substituted by a C$_{5-10}$-heteroaryl containing one, two, or three heteroatoms selected from oxygen, sulfur, and nitrogen, wherein the C$_{5-10}$-heteroaryl is optionally substituted by one or more groups selected from phenyl, methyl, ethyl, propyl, butyl, cyclopropyl, cyclobutyl, CF$_3$, CN, CONH$_2$, CONMe$_2$, CONEt$_2$, COOH, COOMe, COOEt, COH, COMe, OH, OMe, OEt, F, Cl, Br, NH$_2$, NMe$_2$, NEt$_2$, and NPr$_2$,
R$^3$ is phenyl substituted by a C$_{3-10}$-heterocycle containing one or two heteroatoms selected from oxygen and nitrogen, wherein the C$_{3-10}$-heterocycle is optionally substituted by one or more groups selected from C$_{1-4}$-alkyl and oxo, or
R$^3$ is benzimidazolyl optionally substituted by one or more groups selected from methyl, propyl, CF$_3$, CH$_2$CF$_3$, cyclopropyl, and cyclohexyl;
R$^4$ is methyl, ethyl, propyl, butyl, CF$_3$, CH$_2$CF$_3$, F, Cl, or Br; and
or a pharmacologically acceptable salt, enantiomer or hydrate thereof.

9. The method of claim 1, wherein in the compound of formula 1:
A is CH$_2$, CHMe, CMe$_2$, 1,1'-cyclopropylene, or 1,1'-cyclobutylidene;
X is O;
n is 0 or 1;
R$^1$ and R$^2$ are each H;
R$^3$ is H or 4-phenylcyclohexanyl,
R$^3$ is phenyl optionally substituted by NR$^{3.1}$R$^{3.2}$, wherein R$^{3.1}$ is H, methyl, SO$_2$Me, SO$_2$CF$_3$, or SO$_2$-phenyl, and R$^{3.2}$ is H or a group selected from methyl and ethyl, each optionally substituted by one or more groups selected from NH$_2$, NHMe, NMe$_2$, oxo, N-piperidinyl, N-morpholinyl, and N-methylpiperazinyl,
R$^3$ is phenyl substituted by a C$_{5-10}$-heteroaryl containing one, two, or three heteroatoms selected from oxygen, sulfur, and nitrogen, wherein the C$_{5-10}$-heteroaryl is optionally substituted by one or more groups selected from phenyl, methyl, ethyl, propyl, butyl, cyclopropyl, cyclobutyl, CF$_3$, CN, CONH$_2$, CONMe$_2$, CONEt$_2$, COOH, COOMe, COOEt, COH, COMe, OH, OMe, OEt, F, Cl, Br, SO$_2$Me, SONH$_2$, SONMe$_2$, NO$_2$, NH$_2$, NMe$_2$, NEt$_2$, and NPr$_2$, or
R$^3$ is phenyl optionally substituted by a C$_{3-10}$-heterocycle containing one or two heteroatoms selected from oxygen and nitrogen, wherein the C$_{3-10}$-heterocycle is optionally substituted by one or more groups selected from C$_{1-4}$-alkyl and oxo;
R$^4$ is H, F, or Cl; and
or a pharmacologically acceptable salt, enantiomer or hydrate thereof.

10. The method of claim 1, wherein the method is for treating COPD, chronic bronchitis or asthma.

11. A method of claim 1, wherein the compound of formula 1 is administered in the form of a pharmaceutical composition together with one or more pharmaceutically acceptable excipients.

12. A method of claim 2, wherein the compound of formula 1 is administered in the form of a pharmaceutical composition together with one or more pharmaceutically acceptable excipients.

13. A method of claim 3, wherein the compound of formula 1 is administered in the form of a pharmaceutical composition together with one or more pharmaceutically acceptable excipients.

14. A method of claim 4, wherein the compound of formula 1 is administered in the form of a pharmaceutical composition together with one or more pharmaceutically acceptable excipients.

15. A method of claim 5, wherein the compound of formula 1 is administered in the form of a pharmaceutical composition together with one or more pharmaceutically acceptable excipients.

16. A method of claim 6, wherein the compound of formula 1 is administered in the form of a pharmaceutical composition together with one or more pharmaceutically acceptable excipients.

17. A method of claim 7, wherein the compound of formula 1 is administered in the form of a pharmaceutical composition together with one or more pharmaceutically acceptable excipients.

18. A method of claim 8, wherein the compound of formula 1 is administered in the form of a pharmaceutical composition together with one or more pharmaceutically acceptable excipients.

19. A method of claim 9, wherein the compound of formula 1 is administered in the form of a pharmaceutical composition together with one or more pharmaceutically acceptable excipients.

20. A method of claim 10, wherein the compound of formula 1 is administered in the form of a pharmaceutical composition together with one or more pharmaceutically acceptable excipients.

* * * * *